(12) United States Patent
Schrader et al.

(10) Patent No.: US 8,481,494 B2
(45) Date of Patent: Jul. 9, 2013

(54) COMPOUNDS FOR THE TREATMENT OF DISEASES RELATED TO PROTEIN MISFOLDING

(76) Inventors: Thomas Schrader, Mettmann (DE);
Katrin Hochdörffer, Freiburg (DE);
Julia März-Berberich, Essen (DE);
Luitgard Nagel-Steger, Langenfeld (DE); Gal Bitan, Los Angeles, CA (US);
Sharmistha Sinha, Ames, IA (US)

(\*) Notice: Subject to any disclaimer, the term of this patent is extended or adjusted under 35 U.S.C. 154(b) by 0 days.

(21) Appl. No.: 13/504,325

(22) PCT Filed: Jan. 26, 2010

(86) PCT No.: PCT/EP2010/000437
§ 371 (c)(1),
(2), (4) Date: Jul. 12, 2012

(87) PCT Pub. No.: WO2011/050864
PCT Pub. Date: May 5, 2011

(65) Prior Publication Data
US 2012/0270795 A1  Oct. 25, 2012

(30) Foreign Application Priority Data
Oct. 26, 2009  (WO) ............... PCT/EP2009/007627

(51) Int. Cl.
*A61K 38/00* (2006.01)
*A61K 38/04* (2006.01)
*A61K 38/08* (2006.01)
*A61K 38/10* (2006.01)
*A61K 31/4155* (2006.01)
*C07K 5/00* (2006.01)
*C07K 7/00* (2006.01)
*C07D 403/14* (2006.01)

(52) U.S. Cl.
USPC ........ 514/17.8; 514/21.4; 514/21.5; 514/21.6; 514/21.7; 514/21.8; 514/21.9; 514/21.91; 514/407; 530/326; 530/327; 530/328; 530/329; 530/330; 530/331; 548/365.1

(58) Field of Classification Search
USPC .............. 514/17.8, 21.4, 21.5, 21.6, 21.7, 514/21.8, 21.9, 21.91, 407; 530/326, 327, 530/328, 329, 330, 331; 548/365.1
See application file for complete search history.

(56) References Cited

FOREIGN PATENT DOCUMENTS
WO  WO 2007112922  \* 10/2007 .............. 548/365.1

\* cited by examiner

*Primary Examiner* — Samantha Shterengarts
(74) *Attorney, Agent, or Firm* — Brannon Sowers & Cracraft PC

(57) ABSTRACT

The present invention relates to the field of protein misfolding diseases and thus to diseases which are associated with or induced by abnormal or pathogenic three-dimensional folding of proteins and/or peptides or which are linked to pathogenic conformational changes of proteins and/or peptides, such as Alzheimer's disease. Particularly, the present invention provides novel trimeric pyrazole compounds, which exhibit a therapeutic effectiveness in regard to the aforementioned protein misfolding diseases, and refers to their use for the treatment of such protein misfolding diseases, especially neurodegenerative diseases as well as to medicaments or pharmaceutical compositions comprising these compounds.

18 Claims, 20 Drawing Sheets

COMPOUNDS FOR THE TREATMENT OF DISEASES RELATED TO PROTEIN MISFOLDING

CROSS-REFERENCES TO RELATED APPLICATIONS

This application is a National Stage filing of International Application PCT/EP 2010/000437 filed Jan. 26, 2010, entitled "NEW COMPOUNDS FOR THE TREATMENT OF DISEASES RELATED TO PROTEIN MISFOLDING" claiming priority to PCT/EP2009/007627 filed Oct. 26, 2009. The subject application claims priority to PCT/EP 2010/000437 and to PCT/EP2009/007627, and incorporates all by reference herein, in their entirety.

BACKGROUND OF THE INVENTION

The present invention relates to the field of protein misfolding diseases and thus to diseases which are associated with or induced by abnormal or pathogenic three-dimensional folding of proteins and/or peptides or which are linked to pathogenic conformational changes of proteins and/or peptides. Especially, the present invention refers to neurodegenerative diseases which are related to or caused by protein misfolding like Alzheimer's disease and the like.

Especially, the present invention refers to novel specific trimeric pyrazole compounds which exhibit a therapeutic effectiveness in regard to the aforementioned protein misfolding diseases, especially in so far as they are able to suppress or at least to reduce the misfolding of proteins and/or the aggregation of misfolded proteins to layered aggregates, like amyloid plaques. Furthermore, the specific trimeric pyrazole compounds according to the present invention are additionally capable to disassemble already existing misfolded proteins and/or aggregates of misfolded proteins.

The present invention also relates to novel specific trimeric pyrazole compounds for the prophylactic and/or therapeutic (i.e. curative) treatment of protein misfolding diseases, especially neurodegenerative diseases.

Furthermore, the present invention refers to the use of at least one trimeric pyrazole compound of the invention for the prophylactic and/or therapeutic (i.e. curative) treatment of protein misfolding diseases, especially neurodegenerative diseases.

Further, the present invention relates to the use of trimeric pyrazole compounds of the invention for producing a medicament or a pharmaceutical for the prophylactic and/or therapeutic (i.e. curative) treatment of protein misfolding diseases, especially neurodegenerative diseases.

In addition, the present invention also refers to a medicament and/or pharmaceutic composition comprising at least one trimeric pyrazole compound of the invention for the prophylactic and/or therapeutic (i.e. curative) treatment of protein misfolding diseases, especially neurodegenerative diseases.

Moreover, the present invention also provides a kit for the inventive uses and treatment methods as described herein, the kit comprising at least one trimeric pyrazole compound of the invention, preferably in a suitable application form.

Furthermore, the present invention also refers to a method of treatment of protein misfolding diseases, especially neurodegenerative diseases, wherein at least one trimeric pyrazole compound is used and preferably applied to a human or animal suffering from a protein misfolding disease, especially a neurodegenerative disease.

Finally, the present invention also refers to methods for synthesizing (producing) and/or for the providing of the specific trimeric pyrazole compounds of the invention.

In physiology, one of the most important processes can be seen in the folding of the translated linear strand of amino acids into a fully functional three-dimensional protein, which represents one of the most complex challenges facing the cellular protein factory. A large amount of physiological tools reveal a tightly regulated assembly line and multiple factors guide nascent proteins to select the correct shape and/or conformation from an almost infinite array of possibilities. Furthermore, in biological systems, specific control mechanisms exist which ensure that misfolded products are targeted for degradation before they cause harm. However, a failure or malfunction of these control systems or the excessive occurrence of protein misfolding, also especially after protein biosynthesis (i.e. the conversion of normally folded protein into pathogenic forms) can result in a huge variety of diseases, which are commonly designated as protein misfolding diseases or diseases related to protein misfolding.

Among the protein misfolding diseases, Alzheimer's disease, Bovine Spongiforme Encephalopathy (BSE), Creutzfeldt-Jacob's disease (CJD), Huntington's disease, Lewy Body dementia, Parkinson's disease, Diabetes mellitus of type II and Alzheimer's disease (AD) can be mentioned exemplarily.

With respect to Creutzfeldt-Jacob's disease or CJD, which is the most common among the types of transmissible spongiforme encephalopathies found in humans, this protein misfolding disease is caused by prions and is thus sometimes also designated as a prion disease. The prion that is believed to cause CJD exhibits at least two stable conformations. The native state is water-soluble and present in healthy cells. Its biological function is presumably in transmembrane transport or signaling. The other confirmation state is very poorly water-soluble and readily forms protein aggregates. The CJD prion is dangerous because it promotes refolding of native proteins into the diseased state resulting in β-pleated sheets. The number of misfolded protein molecules thus increases exponentially and the process leads to a large quantity of insoluble prions in affected cells. This mass of misfolded proteins disrupts cell function and causes cell death. The misfolding is characterized by a folding of the dominantly α-helica regions into β-pleated sheets of the CJD prion. There is currently no cure for CJD. The disease is invariably fatal.

Diabetes mellitus type II also represents a protein misfolding disease. With respect to this disease, the so-called amyloid polypeptide (IAPP or amylin) is commonly found in pancreatic islets of patients suffering from Diabetes mellitus type II or harbouring an insulinoma. Recent results suggest that IAPP can induce apoptotic cell-death in insulin-producing β-cells. IAPP is capable of forming amyloid fibrils in vitro. Within the fibrillization reaction, the earlier prefibrillar structures are extremely toxic to β-cell and insuline producing cells. A later amyloid fiber structures also seems to have some cytotoxic effect on cell cultures. Therefore, IAPP represents an important pharmacological target for the treatment of Diabetes mellitus II diseases.

Moreover, also Alzheimer's disease has been identified as a protein misfolding disease (proteopathy), caused by accumulation of abnormally folded A-β and tau-proteins in the brain.

Furthermore, so-called synuclein also represents an interesting pharmacological target. The protein α-synuclein has been found to be mutated in several families with autosomal dominant Parkinson's disease. Mutations in α-synuclein are associated with early-onset of especially familiar Parkinson's disease. The protein aggregates abnormally in Parkinson's disease, Alzheimer's disease, Lewy body disease and other neurodegenerative diseases.

Thus, previously unrelated diseases, such as Alzheimer's disease, prion diseases and diabetes, share the pathological feature of aggregated misfolded proteins, which especially occur in the form of large deposits in biological systems (e.g. amyloid plaques in Alzheimer's disease). This common principle suggests that these protein misfolding diseases are linked by common principles, which therefore represents common targets for therapeutic intervention and approaches.

Not at least due to the high impact on the persons concerned, neurodegenerative diseases play an important role among the aforenamed protein misfolding diseases. In general, neurodegenerative diseases can be defined as a condition in which cells of the brain and/or spinal cord are lost, resulting in a decrease of essential functions of the brain, especially with regard to the cognitive and/or motoric function as well as the processing of sensory information. In this context, neurodegenerative diseases are commonly linked with conditions affecting memory and related to dementia but also with conditions causing problems of the control of movements, such as ataxia. Neurodegeneration is often caused by misfolding of proteins, especially in such a way that the misfolded proteins can no longer perform their regular cellular functions and instead trigger equivalent modifications in normal proteins, thus creating a cascade of damage that eventually results in significant neuronal death. Normally, neurodegeneration begins long before the patient experiences any symptoms. It can be months or years before any effect is felt. In general, symptoms are noticed when many cells die or cease to function.

The most common form of dementia is the so-called Alzheimer's disease (AD), which is synonymously also denoted as Alzheimer disease, Senile Dementia of the Alzheimer Type (SDAT) or simply Alzheimer's. Generally, it is diagnosed in people over 65 years of age, although the less-prevalent early-onset of AD can occur much earlier. As of September 2009, this number is reported to be at least 35 million worldwide. The prevalence of AD is estimated to reach approximately 107 million people by 2050.

Although the cause of AD is unique for every individual, there are many common symptoms. The earliest observable symptoms are often mistakenly thought to be age-related concerns or manifestations of stress. In the early stages, the most commonly recognized symptom is memory loss, such as difficulty in remembering recently learned facts. As the disease advances, symptoms include confusion, irritability and aggression, mood swings, language breakdown, long-term memory loss and the general withdrawal of the sufferer as the senses of the person concerned decline. Regularly, body functions are lost, ultimately leading to death. AD develops for an indeterminate period of time before coming fully apparent and it can progress undiagnosed for years. The mean life expectancy following diagnosis is approximately seven years. Fewer than three percent of individuals live more than fourteen years after diagnoses.

Alzheimer's disease is characterized by loss of neurons and synopsis in the cerebral cortex and certain subcortical regions. This loss results in gross atrophy of the affected regions of the brain, including degeneration in the temporal lobe and parietal lobe, and parts of the frontal cortex and cingulat gyrus.

Alzheimer's represents a protein misfolding disease caused by accumulation of abnormally folded A-β and tau-proteins in the brain. Plaques are made up of small peptides, 39 to 43 amino acids in length, called beta-amyloid (also written as A-β or Aβ or ABeta). Beta-amyloid is a fragment from a larger protein called amyloid precurser protein (APP), a transmembrane protein that penetrates through the neuron's membrane. APP is critical to neuron growth, survival and postinjury repair. In Alzheimer's disease, APP is divided into smaller fragments by enzymes through proteolysis. One of these fragments gives rise to fibrils of beta-amyloid, which forms clumps that are deposited outside of neurons in dense formations known as senile plaques or amyloid plaques.

Amyloid beta (A-β, Aβ or ABeta) is a peptide of 39 to 43 amino acids that appears to be the main constituent of amyloid plaques in the brains of persons suffering from protein misfolding diseases, like Alzheimer's disease. Similar plaques appear in some variants of Lewy body dementia. The plaques formed by Aβ are composed of a tangle of regularly ordered fibrillar aggregates called amyloid fibers, a protein fold which is also shared by other peptides such as prions associated with other protein misfolding diseases, like CJD. Aβ is formed after sequential cleavage of the amyloid precursor protein, a transmembrane glycoprotein. Aβ protein is generated by successive action of the so-called β- and γ-secretases. The γ-secretase, which produces the C-terminal end of the Aβ-peptide, cleaves within the transmembrane region of APP and can generate a number of isoforms of 39 to 43 amino acid residues in length. The most common isoforms are $A\beta_{40}$ and $A\beta_{42}$. The shorter $A\beta_{40}$ form is the more common one, wherein $A\beta_{42}$ represents the more fibrillogenic isoform of Aβ. Thus, $A\beta_{42}$ is the most amyloidogenic form of the peptide.

The accumulation of beta-amyloid peptides is discussed as the central event triggering neuron degeneration. Accumulation of aggregated amyloid fibrils, which are believed to be the toxic form of the protein and seem to be responsible for disrupting the cell calcium ion homeostasis, induces programmed cell death (apoptosis). It is also known that Aβ selectively builds up in the mitochondria in the cells of Alzheimer's-affected brains and that it also inhibits certain enzyme functions and the utilization of glucose by neurons.

Alzheimer's disease is also considered as a tauopathy due to abnormal aggregation of the so-called tau-protein. The tau-protein stabilizes the microtubules as a part of the cytoskeleton in the phosphorylated form thereof. Therefore, it is called a microtubule-associated protein. In AD, the tau-protein undergoes chemical changes and becomes hyperphosphorylated. It then begins to pair with other thread, creating neuro-fibrillary tangles and disintegrating the neuron's transport system.

Furthermore, the degeneration of the muscarinergic cholinerg neurons in AD is associated with a chronic deficiency of the neurotransmitter acetylcholine (ACh), resulting in a significantly decreased signal transmission between the affected neurons.

Up to now, there is no cure for Alzheimer's disease. Available treatments offer relatively small symptomatic benefit but remain palliative in nature. Current treatments can be divided into pharmaceutical, psychosocial and caregiving. Four medications are currently approved by regulatory agencies to treat the cognitive manifestations of AD. Three of them can be classified as acetylcholine esterase inhibitors and the remaining one is an NMDA receptor antagonist. However, no drug has an indication for delaying or halting the progression of the disease.

Thus, on the whole, Alzheimer's disease (AD) is a steadily increasing threat, especially for industrialized countries with a growing percentage of old individuals. Research on potential therapies has been going on for several decades now, without producing one single drug which is able to cure Alzheimer's disease. Since AD is accompanied by many diverse symptoms, numerous avenues have been exploited in the search of a therapy. Antiinflammatory, antihypertensive as well as hypolipidemic agents, passive and active immunisation, cholinergic therapies, neuroprotective agents, glutamate receptor antagonists, β- and γ-secretase inhibitors, β-amyloid and tau aggregation inhibitors, metal chelating agents, monoamine oxidase inhibitors, medicinal plants are only a number of the most prominent classes. In recent years passive immunization with Aβ-specific antibodies held most promise for a breakthrough, however, the results of phase II clinical trial revealed only moderate or weak effects with a large percentage of treated patients. As a consequence, the call for small molecules was revived and reinitiated.

A plethora of small molecules has been screened in the past three decades for their antiaggregation potential against the Alzheimer's peptide. Among these, often colored heterocyclic compounds have been identified, which are in general thought to somehow intercalate between the insoluble cross-β-sheet structure of Aβ fibrils (e.g. congo red, rifampicin, melatonin, cucurmin) Zn- and Cu-chelating agents were thought to lower the aggregation tendency of monomeric Aβ strands (clioquinol). Another prevailing class of compounds are peptides, in some cases taken directly from putative nucleation sites within the Aβ molecule, however, only very few of these compounds stem from rational design with a known structural motif in their complexes with Aβ-monomers, oligomers or fibrils. In this context, a β-sheet breaker LPFFD (iAbeta5) retained the high affinity towards the self-complementary KLVFF region of Aβ, but impaired its β-sheet forming propensity by introducing a proline-kink; the D-peptide LVFFV (PPI-1019) essentially interferes with the aggregation of β-amyloid in the brain and may help to promote its clearance. Furthermore, in prior art, hybrid peptides built from KLVFF and a highly charged KKKKK or EEEEE terminus have been synthesized. Aggregation of toxic Aβ oligomers is promoted because of an increased surface tension.

Another prominent class are alternating N-methylated and non-methylated peptide amides or esters. These are able to cap growing β-sheets without the ability of crosslinking because their back is blocked for hydrogen bonding due to the sterically demanding N-methyl groups or ester oxygens. These substances have recently been optimized with respect to the antiaggregatory capacity by introduction of three cyclohexylglycine units and reached nanomolar $IC_{50}$ values. The compound is also thought to accelerate Aβ self-assembly and thereby deplete the level of neurotoxic Aβ-oligomers. Other examples comprise the small molecule homotaurin, which disrupts complexes between Aβ and glucosaminoglycans. Scyllo-inositol appears to bind oligomers of $Aβ_{42}$, preventing them from damaging synapses. Oligomer-specific Aβ antibodies indicated that scyllo-inositol appears to increase the number of monomers and trimers while reducing the amount of larger oligomeric species, such as 40 mers. A recent approach focuses on Aβ binders from D-peptide libraries by phage display methods.

However, little knowledge and information is available on the exact mechanism of action for most Aβ complexing agents, even less on structural details. Furthermore, the effectiveness of the substances is not always sufficient and there are also questions arising with regard to the physiological compatibility of the substances.

Furthermore, a promising approach with regard to the treatment of AD base on the use of aminopyrazoles, which have proven to bind selectively to the backbone of misfolded peptides residing in the β-sheet confirmation.

In prior art, several aminopyrazoles were synthesized with additional side chains for enhanced water solubility. A combination of two consecutive proteinogenic amino acids, flanked by external aminopyrazolecarboxylate was shown to be complementary to an extended β-sheet. Such derivatives were synthesized and also evaluated on the solid phase. Direct interaction of dimeric and trimeric aminopyrazole derivatives with the mouse prion protein as well as with Aβ(1-42) was shown and characterized by SDS-PAGE (Sodium Dodecyl Sulphate Polyacrylamide Gel Electrophoresis), FCS (Fluorescence Correlation Spectroscopy), AUC (Analytical Ultra Centrifugation), density gradient centrifugation as well as HRMS (High Resolution Mass Spectrometry). The β-sheet recognition as well as the individual strength of all hydrogen bonds involved were also studied in prior art by R2PI spectroscopy on a cooled argon jet stream. It is also known that a trimeric aminopyrazole carboxylate trimer is capable to disassemble preformed Aβ-fibrils in a dose- and time-dependant manner. However, all the aforementioned substances only exhibit a moderate effect with regard to the target structure and are neither optimized with respect to an improved effectiveness in view of an improved compatibility and availability at the pharmacological site of action.

WO 03/095429 A1 refers to substances having a donor-acceptor/donor-structure on the basis of heterocyclic compounds being linked to specific residues. The donor/acceptor/donor-pattern corresponds to the β-pleated sheet structure of a misfolded protein. The substances described in this document prevent in some respects the aggregation of misfolded proteins into β-amyloid plaques.

Furthermore, WO 2007/112922 A1 relates to trimeric water-soluble aminopyrazole compounds having a radical at the N-terminal site of the molecule in the form of a straight-chain or branched alkyl group or an amino acid group or a polyamino acid group and having a specific radical at the C-terminal site of the molecule in the form of a NOH, $OR^3$ or $NHR^3$ group, in which $R^3$ is a straight chain or a branched alkyl group or an amino acid group or a polyamino acid group. The molecules described in this document also have a certain effect on the Aβ-protein.

Although the respective substances named in the above documents have a certain effect on Aβ-protein, there still remains a great need and potential for a further improvement of the effectiveness of substances especially interacting with misfolded proteins, like the Aβ-protein. Furthermore, there also still remains a need to improve the bioavailability of these substances, especially at the place and/or site of pharmacological action, in particular taking into consideration the penetration of the blood/brain-barrier.

Thus, especially in view of the seriousness of protein misfolding diseases like Alzheimer's disease and the high incidence of these diseases, there is an urgent need for providing new therapeutic approaches and new therapeutic compounds being effective with respect to the treatment of protein misfolding diseases like Alzheimer's disease.

BRIEF SUMMARY OF THE INVENTION

Therefore, especially in the light of the above-mentioned medical background, it is an object of the present invention to provide a new and effective concept or approach with respect to the prophylactic and/or therapeutic (i.e. curative) treatment of protein misfolding diseases, like Alzheimer's disease, which is to overcome or at least to diminish the aforementioned disadvantages linked to the prior art methods.

Especially, it is an object of the present invention to provide specific pharmacologically active substances or compounds exhibiting a high effectiveness in the field of the treatment of protein misfolding diseases.

Furthermore, it is another object of the present invention to provide specific substances having an improved effectiveness with regard to protein misfolding diseases, like Alzheimer's disease, and which also have reduced side-effects if compared to the prior art substances, thereby at the same time being highly effective at the site of pharmacological action, i.e. having improved properties with respect to the uptake and incorporation into the region of the brain, especially in view of an improved penetration capability through the blood/brain-barrier.

Surprisingly, applicant has found out that the afore-described objects can be solved, inter alia, by the subject-matter described herein; further, especially advantageous embodiments are the subject-matter of the respective claims.

Furthermore, according to another aspect of the present invention, the present invention refers to specific trimeric pyrazole compounds for the prophylactic and/or therapeutic (curative) treatment of a protein misfolding disease described herein. Further, especially advantageous embodiments are the subject-matter of the respective dependent claims.

Moreover, according to further aspects of the present invention, the present invention also refers to the respective uses of the trimeric pyrazole compound of the invention described herein. Further, especially advantageous embodiments are the subject-matter of the respective claims.

Furthermore, according to a further aspect of the present invention, the present invention refers to a medicament or a pharmaceutical composition described herein; further, especially advantageous embodiments are the subject-matter of the respective claims.

The present invention also refers, according to another aspect of the present invention described herein, to a kit, the inventive kit comprising the trimeric pyrazole compounds of the present invention. Further preferably advantageous embodiments are the subject-matter of the respective claims.

Finally, according to another aspect of the present invention, the present invention refers to a method of treating a human or an animal suffering from a protein misfolding disease described herein. Further, especially advantageous embodiments are the subject-matter of the respective method claims.

In the following, it has to be noted that explanations, details, examples etc. given with respect to one aspect of the present invention only shall, of course, also refer to all the other aspects of the present invention, even without explicit mentioning of this fact. Thus, it may well be in the following, that specific aspects, explanations, details etc. are only delineated with respect to one specific embodiment only in order to avoid unnecessary repetitions, but they also apply with respect to all the other aspects of the present invention.

Applicant has now surprisingly found out a new approach for the treatment of protein misfolding diseases thereby using specific trimeric pyrazole compounds.

Especially, applicant has found out that trimeric pyrazole compounds of the present invention having a nitro group —$NO_2$, on its one end (i.e. at the first pyrazole ring), and, on its opposite or other end (i.e. at the third pyrazole ring), specific ligands and/or groups possess outstanding properties with regard to the inhibition or the decrease of protein misfolding, especially with regard to misfolded proteins having beta-sheet structures, like the Aβ-protein, and the respective aggregation thereof.

With respect to the protein misfolding diseases, besides the Aβ-protein, also the aforenamed amylin (IAPP), synuclein proteins and prion molecules especially associated with CJD may represent the pharmacological target for the inventive trimeric pyrazole compounds. In general, the present invention is not limited to the aforenamed proteins. For, the inventive trimeric pyrazole compounds can be in general tailored with regard to the specific pharmacological target, especially in so far as they are related with or cause protein misfolding diseases and exhibit an abnormal and/or pathogenic β-sheet structure. On the whole, the β-sheet structure of the misfolded protein represents a common basic structure, which is targeted by the inventive concept.

With regard to the inventive trimeric pyrazole compounds, one central motif thereof has to be seen in the trimeric combination or condensation or linkage of three single pyrazoles, especially wherein two aminopyrazoles and one nitropyrazole are linked to form the trimeric central motif of the inventive compounds.

For, applicant has shown that the respective inventive aminopyrazoles exhibit a specific donor/acceptor/donor-sequence (DAD-sequence or DAD-structure) which is able to interact with the corresponding sequence of a misfolded protein, especially in the form of a β-sheet. Also for this reason, the inventive trimeric pyrazole compounds act as β-sheet ligands which are able to interact and bind, respectively, with the pharmacological target structure, i.e. the respective misfolded protein structure, especially with the protein in β-pleated form.

Without being bound to this theory, on the basis of the so-called key/lock-mechanism, the respective molecular target exhibits complementary structures with regard to the hydrogen bond donors and acceptors on the basis of the DAD-sequence of the inventive trimeric pyrazole compounds. In this context, without being bound to this theory, the acceptor-motif of the inventive trimeric pyrazole compound is provided by the respective carbonyl groups (C=O-groups) of the molecule, wherein the donor structures are provided by the respective amide groups (NH-groups) of the molecule. With regard to the interaction of the inventive trimeric pyrazole compound and the target molecule, i.e. the respective misfolded protein, the interaction is generally based on hydrogen bonds. However, the interaction is generally not limited to this intermolecular interaction, but also extends to any other interactions forms, which are as such well known to the skilled practitioner as such.

With respect to the inventive trimeric pyrazole compounds, applicant has now surprisingly found out that the use of specific ligands on both end sites of the trimeric pyrazole, i.e. a nitro group —$NO_2$, on its one end (i.e. at the first pyrazole ring), and specific ligands and/or groups on its opposite or other end (i.e. at the third pyrazole ring), results in an outstanding and surprising improvement of the effectiveness with respect to the interaction of the inventive trimeric pyrazole compounds to target structures, i.e. with respect to the misfolded proteins and/or peptides which reside in the so-called β-sheet-conformation. In this context, the inventive compounds—without being bound to that theory—perfectly fit to the backbone of the misfolded peptides. This results in a strong inhibition of the growing of Aβ-ensembles. Furthermore, the inventive compounds also exhibit a strong interaction with regard to preformed Aβ-fibrills which leads to their disassembly.

Due to the specific optimization of the terminal groups of the trimeric pyrazole compounds of the invention, a decisive improvement of the interaction between the trimeric pyrazole compound, on the one hand, and the target protein, on the other hand, is realized, resulting in an outstanding complementary fit and thus improved interaction between the trimeric pyrazole compound and the pharmacological target. Thus, the inventive trimeric pyrazole compounds exhibit a high affinity and specifity with regard to the misfolded proteins residing in the β-sheet conformation.

Thus, on the whole, one central gist of the present invention has to be seen in the fact that on the basis of a specific modification of a pyrazole basic structure with purposefully selected ligands, a significant optimization of the key/lock-mechanism and thus of the specifity and affinity of the trimeric pyrazole compounds of the present invention with regard to the target structure has been realized, resulting in outstanding therapeutic properties of the inventive compounds with regard to diseases basing on protein misfolding, e.g. Alzheimer's disease.

Thus, according to a first aspect of the present invention, there is provided a trimeric pyrazole compound of the general formula (I)

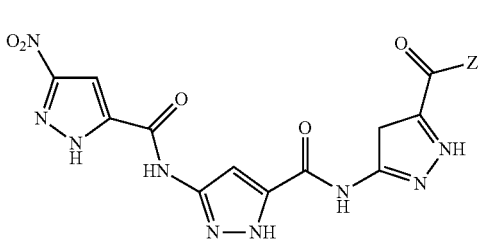

wherein in the general formula (I) the group Z denotes a group X—Y,
wherein X denotes:
(i) a single bond or
(ii) a group of the general formula (II)

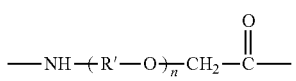

wherein in the general formula (II) the group R' denotes a divalent rest selected from $C_2$-$C_{10}$-alkylene and n is an integer selected in the range of from 1 to 20, especially 2 to 15, preferably 3 to 10;
wherein Y denotes:
(i) a group —O⁻ or a group —OH;
(ii) a carboxylic acid radical or a (poly)amino acid radical or its salts, especially pharmacologically acceptable salts; its esters, especially alkyl or aryl esters; or its amides;
(iii) an amine or diamine radical which is optionally protonated.

Thus, with regard to the generic formula (I) and according to the inventive concept, the trimeric pyrazole compound is provided at its one end (i.e. at the first pyrazole ring; in general also denoted as the N-terminal end or site of the trimeric pyrazole) with a nitro group ($NO_2$-group) as delineated on the left end of the molecule as presented in formula (I). Furthermore, the trimeric pyrazole of the present invention exhibits a deprotonized hydroxy group or a specific radical basing on a molecule comprising or consisting of a specific group Z=X—Y on its opposite or other end (i.e. at the third pyrazole ring; in general also denoted as the C-terminal end or site of the trimeric pyrazole) as delineated on the right end of the molecule as presented in formula (I), wherein X may act as a spacer and Y may act as a further interacting part of the molecule especially with regard to the misfolded protein structure. Due to the specific chemical structure of the trimeric pyrazole compounds of the present invention, a highly complementary structure to target proteins, i.e. misfolded proteins and/or peptides residing in the β-sheet structure, is provided, resulting in an outstanding pharmacological effectiveness.

With regard to the present invention, the trimeric pyrazole motif as given in formula (I) is also abbreviated as "Trimer" and/or "Trim", so that both abbreviations are synonymously used for the trimeric pyrazole basic structure of the inventive compounds, however, with the proviso that the abbreviation "Trimer" and "Trim" refers to the trimeric pyrazole basic structure as given in formula (I) without the group Z. Thus, "Trimer" and/or "Trim" generally refers to the molecular structure on the basis of formula (I), however, without the group Z as such.

It is well understood by the skilled practitioner that the above general formula (I) also comprises and refers to all possible tautomeric structures or forms of the above molecule or formula, respectively, such as e.g. all N—NH-tautomers but also others, especially as exemplified by the following formulae or scheme:

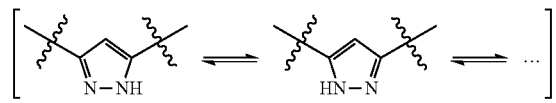

According to a preferred embodiment of the present invention, in the above general formula (I) of the trimeric pyrazole compounds of the present invention as defined above:
X denotes:
(i) a single bond or
(ii) a group of the general formula (II)

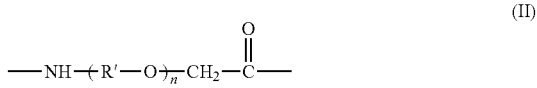

wherein in the general formula (II) the group R' denotes a divalent rest selected from $C_2$-$C_{10}$-alkylene and n is an integer selected in the range of from 1 to 20, especially 2 to 15, preferably 3 to 10;
Y denotes:
(i) a group —O⁻ or a group —OH;
(ii) a (poly)amino acid radical or its salts, especially pharmacologically acceptable salts; its esters, especially alkyl or aryl esters; or its amides;
(iii) an amine or diamine radical which is optionally protonated.

According to another preferred embodiment of the present invention, in the above general formula (I) of the trimeric pyrazole compounds of the present invention as defined above:
X denotes a single bond if Y denotes a group —O⁻ or a group —OH; or
X denotes a single bond or a group of the general formula (II) as defined above if Y denotes (ii) a (poly)amino acid radical or its salts, especially pharmacologically acceptable salts; its esters, especially alkyl or aryl esters; or its amides or (iii) an amine or diamine radical which is optionally protonated.

According to yet another preferred embodiment of the present invention, in the above general formula (I) of the trimeric pyrazole compounds of the present invention as defined above X denotes a single bond or a group of the general formula (II) as defined above and Y denotes (ii) a (poly)amino acid radical or its salts, especially pharmacologically acceptable salts; its esters, especially alkyl or aryl esters; or its amides or (iii) an amine or diamine radical which is optionally protonated.

According to a preferred embodiment, X in the aforementioned formula (I) may denote a group of the general formula (III)

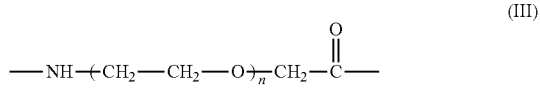

wherein in the general formula (III) n is an integer selected in the range of from 1 to 20, especially 2 to 15, preferably 3 to 10.

According to a further preferred embodiment of the present invention, the group X in the aforementioned formula (I) denotes a group of the general formula (IV)

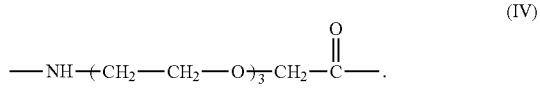

The aforenamed group of the general formula (IV) is also abbreviated, in the following, as "TEG".

With respect to the aforenamed formulae (III) and (IV), this respective molecular structure may act—in a manner of speaking—as a spacer the existence of which further optimizes the effectiveness of the inventive molecule. In this context, applicant has specifically found out that the use of a specific spacer, especially of a TEG-spacer, leads to a further improvement of the suppression of Aβ-fibril formation, especially when combined with further amino acid residues, especially as delineated hereinafter. Without being bound to that specific theory, the TEG-spacer may serve in a dual purpose in so far as it brings recognition units (e.g. the unit Y) close to the U-turn of the fibril and simultaneously protrudes itself into the interior of two parallel Aβ-strands, facilitating further destabilization of the fibrillar structure. The TEG-spacer is in a manner of speaking able to smoothly intercalate between both peptide strands.

According to a further embodiment of the present invention the (poly)amino acid radical may be derived from α- to ω-amino acids, especially α- and/or β-amino acids, preferably α-amino acids.

The designation "α- to ω-amino acids" is well known to the skilled practitioner and refers in general to the positioning of the carboxyl group with respect to the amino group of the amino acid.

According to a further alternative embodiment of the present invention, the (poly)amino acid radical may be derived from proteinogenic or non-proteinogenic amino acids, preferably proteinogenic amino acids.

According to the present invention, the (poly)amino acid radical may be derived from naturally occurring amino acids.

In this context, applicant has surprisingly found out that an especial high effectiveness with respect to the interaction to Aβ can be realized under the proviso that the (poly)amino acid radical is derived from the group consisting of lysine, glycine, cyclohexylglycine, leucine, isoleucine, proline, phenylalanine, aspartic acid, amino butyric acids, especially γ-aminobutyric acid, valine and combinations thereof, preferably lysine.

In this context, especially the use of lysines results in further improved properties of the respective trimeric pyrazole compounds of the invention, especially when combined with a TEG-spacer. In this context, it has been surprisingly found out that the combination of one terminal lysine being bonded to the trimeric pyrazole basic structure via a TEG-spacer results in a very potent compound of the invention with regard to its effectiveness against the respective target structure, especially Aβ. Also multiple lysines result in outstanding properties with regard to the misfolded protein, especially if combined with the TEG-spacer.

With respect to the inventive trimeric pyrazole compound it is preferred according to the present invention that the (poly)amino acid radical is attached or linked via an amide and/or peptide bond.

Furthermore, according to another preferred embodiment of the present invention, the polyamino acid radical may comprise or may be composed of at least two or more amino acids attached or linked to each other via an amide and/or peptide bond each.

The chemical bonding on the basis of amide and/or peptide bonds results in an optimized three-dimensional structure of the inventive compound, further improving the key/lock-mechanism with respect to the interaction with the molecular target structure.

Furthermore, the trimeric pyrazole compound of the present invention is configured such that the polyamino acid radical comprises or is composed of from 2 to 20 amino acids, especially 2 to 10 amino acids, preferably 2 to 6 amino acids, preferably wherein the amino acids are attached or linked to each other via an amide and/or peptide bond each.

Furthermore, according to another preferred embodiment of the present invention, the polyamino acid radical may comprise or may be composed of polylysine units optionally combined with at least one amino acid different from lysine and preferably terminally positioned.

With respect to the abovementioned formula (I) and according to a preferred embodiment of the present invention, the group Z is preferably selected from the group consisting of the following radicals:

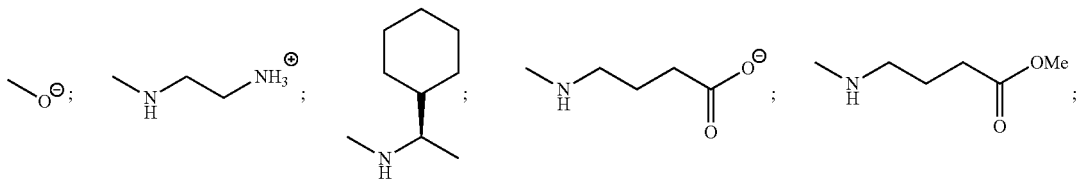

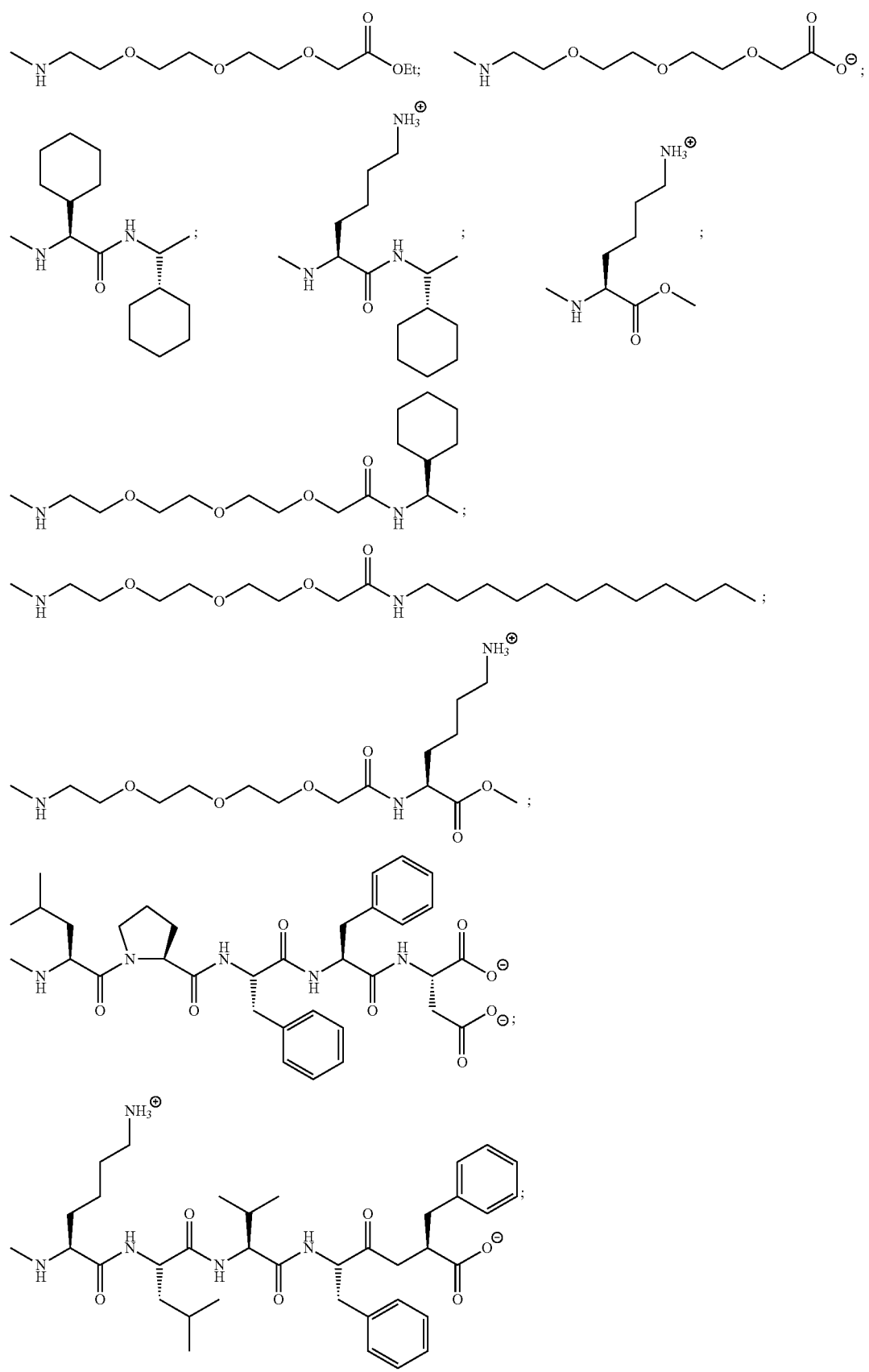

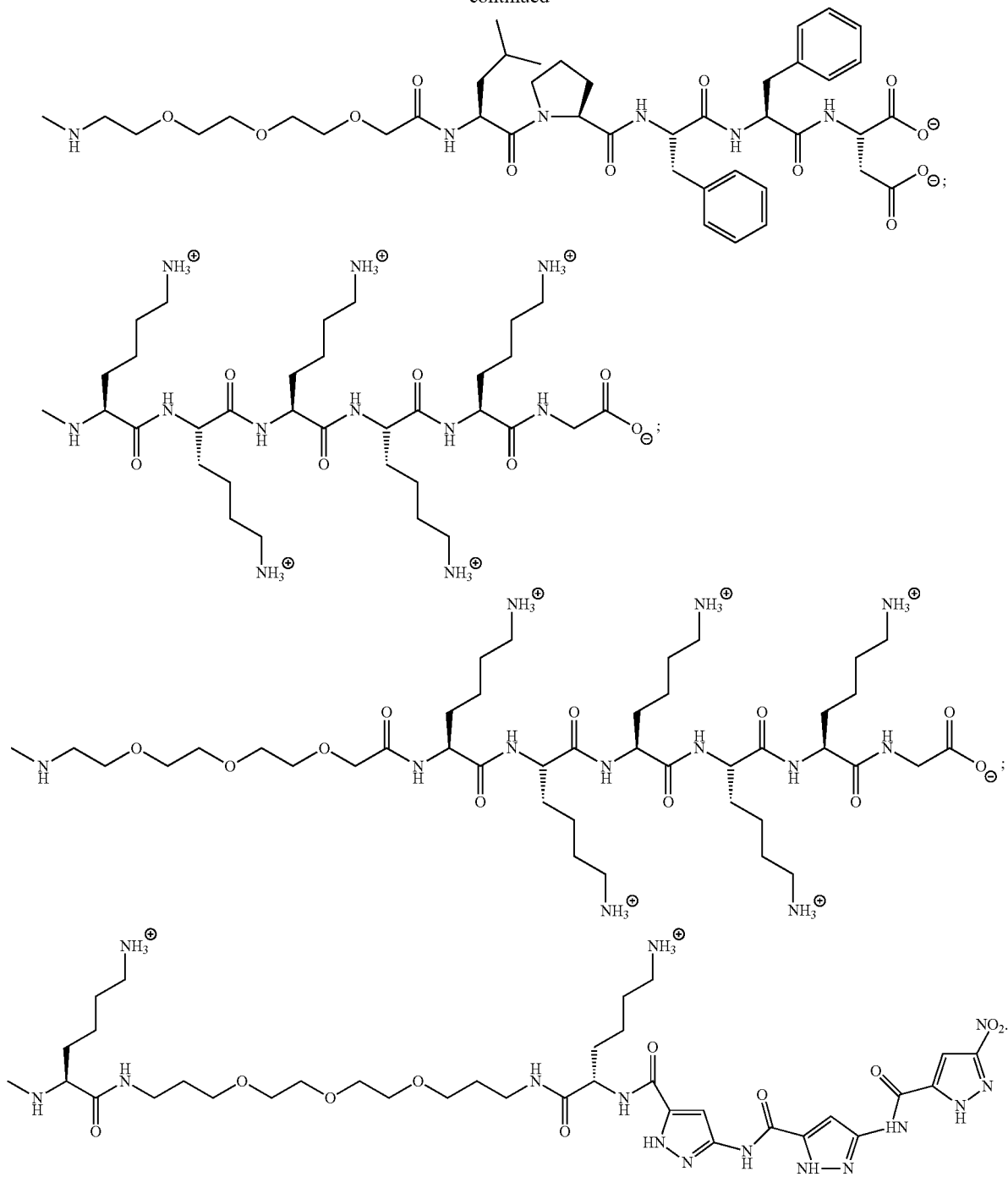
With respect to the abovementioned formula (I) and according to yet another preferred embodiment of the present invention, the group Z is preferably selected from the group consisting of the following radicals:
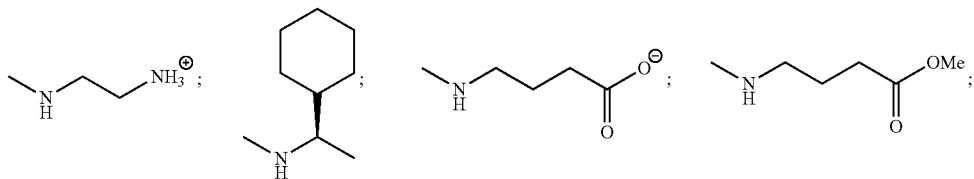

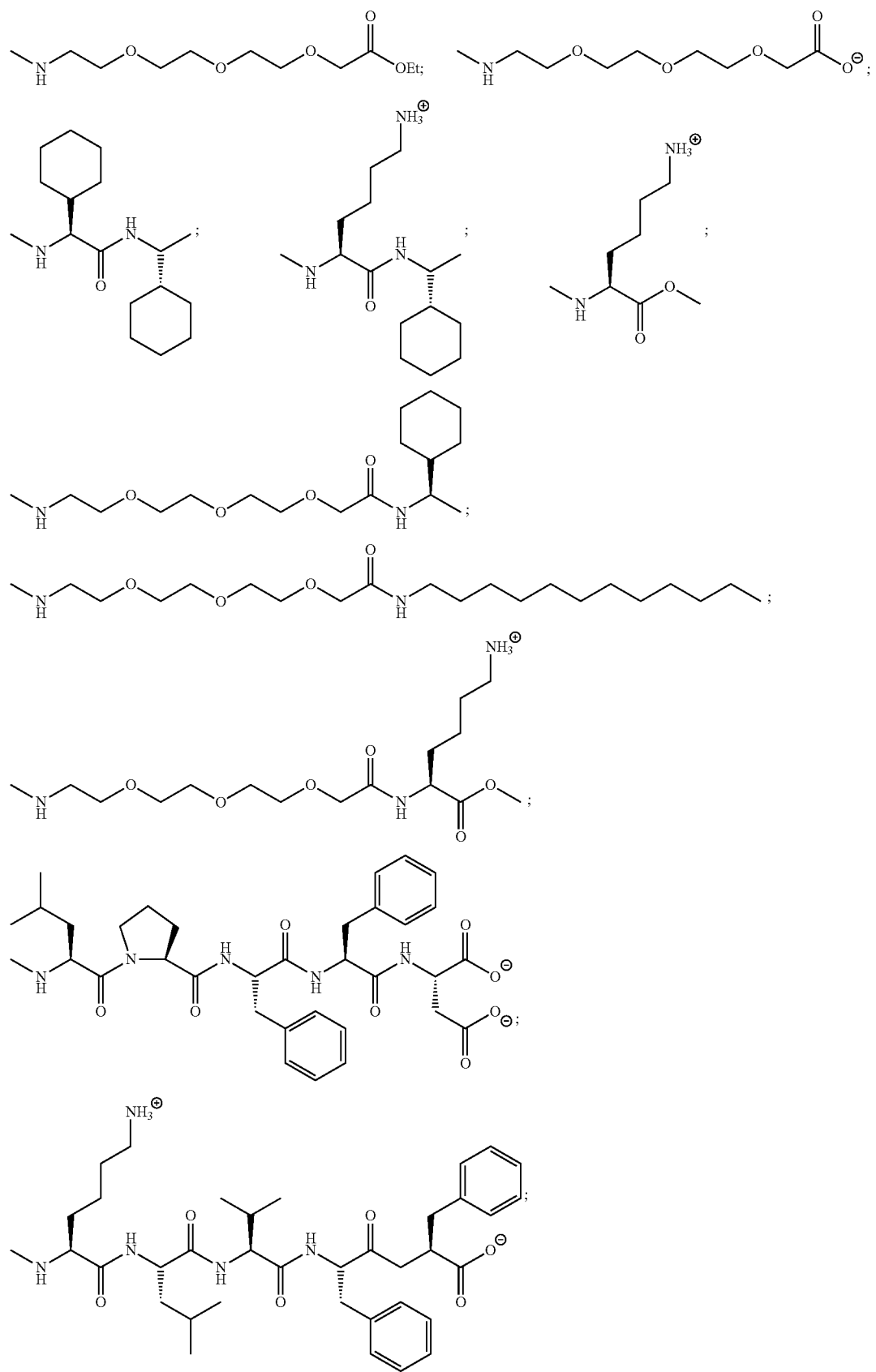

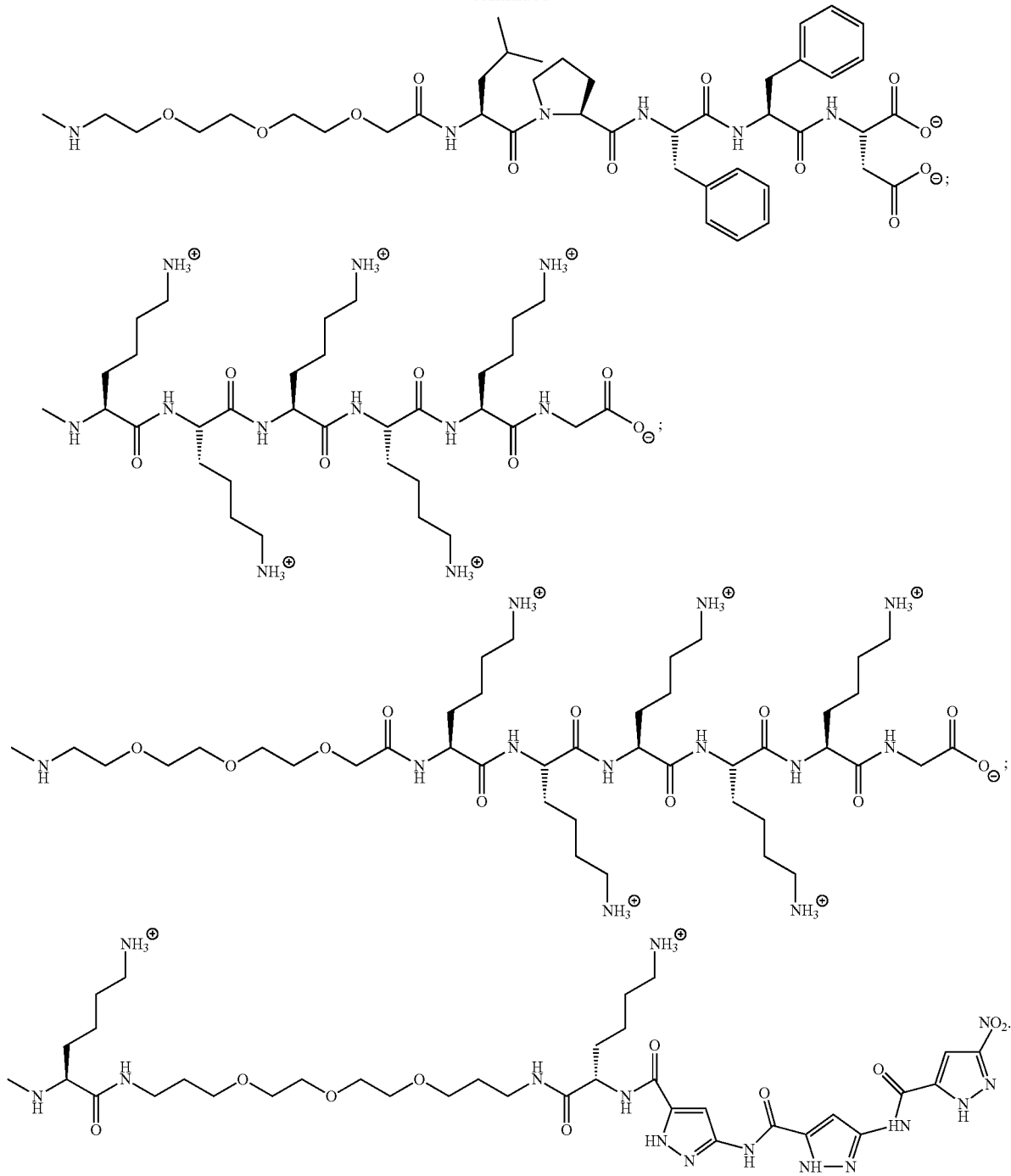

In this context, with regard to the abovementioned specific radicals Z, applicant has surprisingly found out that the specific trimeric pyrazole compounds of the present invention comprising the specific groups have further improved and ameliorated properties with respect to their effectiveness to bind to the respective misfolded proteins or their respective precursors thereof, especially with regard to growing Aβ ensembles and the respective protein aggregates. Furthermore, applicant has surprisingly found out that especially the aforenamed specific trimeric pyrazole compounds of the invention do not only inhibit the growth of the pathogenic protein ensembles, but also leads to the disassembly of already formed or preformed protein aggregates, like preformed Aβ-fibrills. In this context, the aforenamed trimeric pyrazole compounds of the invention exhibit an even more improved and increased effectiveness if compared to the respective compounds of the prior art. This finding is specifically proved by applicant's investigation, as especially presented hereinafter. On the whole, the outstanding performance of the specific trimeric pyrazole compounds of the invention was not at all anticipated and points to their rate impact and potential with regard to the prophylactic and/or therapeutic treatment of the respective protein misfolding diseases, especially Alzheimer's disease (AD). Thus, on the whole, the present invention focuses on the provision of very effective substances on the basis of trimeric pyrazole compounds being able to prevent and inhibit, respectively, the misfolding of proteins, thereby also exhibiting an significant effectiveness with respect to the disassembly of misfolded proteins and/or their respective aggregates. Therefore, the inventive trimeric pyrazole compounds have a decisive impact with regard to neurodegenerative diseases.

According to a second aspect of the present invention, the present invention refers to the abovedefined trimeric pyrazole compound for the prophylactic and/or therapeutic (curative) treatment of a protein misfolding disease.

In this context, according to a preferred embodiment of the present invention, the protein misfolding disease is associated with or caused by misfolding of a protein into an abnormal and/or pathogenic β-sheet, especially in combination with a subsequent protein aggregation.

The protein misfolding disease is preferably selected from the group of neurodegenerative diseases and/or dementia and/or prion diseases, especially Alzheimer's diseases (AD), Parkinson's disease, Creutzfeldt-Jakob disease, Huntington's disease and the like.

However, the present invention is not limited to the above-named diseases. In fact, the inventive concept can be generally applied to any disease being related to or caused by especially conformational changes of proteins from a healthy and/or normal state into an abnormal and/or pathogenic condition. In this context, the inventive trimeric pyrazole compounds can be specifically tailored with regard to the respective target structure, i.e. with regard to the specific protein or protein structure as the molecular target of the inventive trimeric pyrazole compounds.

With regard to the present invention, the protein misfolding disease is preferably Alzheimer's disease (AD).

However, the present invention is not limited to neurodegenerative as such. In this context, the inventive trimeric pyrazole compounds also exhibit an effectiveness with regard to other protein misfolding diseases. In this context, the protein misfolding disease may be Diabetes mellitus, especially Diabetes mellitus type II.

Furthermore, according to a third aspect of the present invention, the present invention also refers to the use of at least one trimeric pyrazole compound as defined above for the prophylactic and/or therapeutic (curative) treatment of a protein misfolding disease.

Furthermore, according to a fourth aspect of the present invention, the present invention also refers to the use of at least one trimeric pyrazole compound as defined above for producing a medicament or a pharmaceutical composition for the prophylactic and/or therapeutic (curative) treatment of a protein misfolding disease.

With respect to the inventive uses according to the third and fourth aspect of claimed invention, the protein misfolding disease may be associated with or caused by misfolding of a protein into an abnormal and/or pathogenic β-sheet, especially in combination with a subsequent protein aggregation.

As delineated above, the protein misfolding disease may be selected from the group of neurodegenerative diseases and/or dementia and/or prion diseases, especially Alzheimer's disease (AD), Parkinson's disease, Creutzfeldt-Jakob disease and Huntington's disease.

According to a preferred embodiment of these aspects of the present invention, the protein misfolding disease is Alzheimer's disease (AD).

Furthermore, it is also possible according to the present invention that the protein misfolding disease is Diabetes mellitus, especially Diabetes mellitus type II.

With regard to the third and fourth aspect of the present invention, the trimeric pyrazole component may be administered in a therapeutically effective amount, i.e. in an amount which provides for an effectiveness with regard to the inhibition and all decrease of the forming of pathogenic protein conformations and/or to provide for an effective disassembly of already formed misfolded proteins or aggregates thereof.

In this context, the amount an/or concentration of the active agent (i.e. of the trimeric pyrazole compound of the invention with regard to its administration can vary widely and will be in general selected by the skilled practitioner in dependence on the activity of the respective trimeric pyrazole compound, body weight of the person concerned, bioavailability and the side of pharmacological action and the like. In this context, according to a typical embodiment, the dosage of the inventive trimeric pyrazole compound may range from 0.0001 to 100 mg/(kg·day), especially from 0.001 to 50 mg/(kg·day), preferably 0.01 mg/(kg·day) to 10 mg/(kg·day), referred to the body weight of a person concerned.

According to the present invention, there is also provided—according to a fifth aspect of the present invention—a medicament or a pharmaceutical composition, especially for the prophylactic and/or therapeutic (curative) treatment of protein misfolding diseases, wherein the medicament and/or pharmaceutical composition comprises at least one trimeric pyrazole compound as defined above. In this context, the medicament or pharmaceutical composition may comprise at least one pharmaceutically acceptable excipient. The respective pharmaceutically acceptable excipients are well-known to the skilled practitioner per se and the skilled practitioner is always able to select the respective excipients with regard to their nature and amounts especially in view of the respective inventive trimeric pyrazole compound to be used in the medicament or pharmaceutical composition.

According to another embodiment of the claimed invention, the medicament or pharmaceutical composition of the invention may be designed as a unit dosage formulation.

In this context, the medicament or pharmaceutical composition may be formulated to be administered and/or applied intravenously, subcutaneously, intraperitoneally, intrathecally, intravesically, topically, orally, rectally, transdermally, subdurally and/or inhalatively.

Especially with regard to a systematically administration and/or application of the inventive trimeric pyrazole compounds, it has to be denoted that the inventive compounds exhibits in general also outstanding characteristics with respect to their ability to penetrate and/or to cross the blood/brain-barrier. In this context, the inventive trimeric pyrazole compounds may exhibit specifically optimized physicochemical properties, especially with regard to their lipophylic properties, which allows them to penetrate in a sufficient manner through blood/brain-barrier in order to be present in an effective amount at the side of pharmacological action, i.e. especially in the region of the neuronal cells in the brain for the case of neurodegenerative diseases.

However, the penetration properties with respect to the blood/brain-barrier may be further enhanced by coadministering the inventive trimeric pyrazole compounds with carrier molecules or the like, which are well-known to the skilled practitioner. For example, the inventive trimeric pyrazole compounds may be administered together with specific peptides, like arginin-rich peptides and/or cationic dendrimers. However, it is also possible to directly administer the inventive trimeric pyrazole compounds to the brain, e.g. via implantation of a specific released system.

The present invention also refers—according to a sixth aspect of the present invention—to a kit, the kit comprising at least one trimeric pyrazole compound as defined above. In this context, with respect to the kit of the present invention, the trimeric pyrazole compound may be deposited in a storage and/or application unit.

Furthermore, the kit of the present invention may comprise instruments for formulating and/or administering the trimeric pyrazole compound of the invention. The inventive kit may also comprise a labeling and/or instructional materials, especially for the administration and/or dosage and/or application of the inventive trimeric pyrazole compound.

Furthermore, with regard to the inventive kit, the kit may also comprise the inventive trimeric pyrazole compound in the form of the medicament or pharmaceutical composition as described above on the basis of the fifth aspect of the present invention.

With regard to the kit of the present invention, it is also possible that the kit may also comprise at least one agent used in the treatment of protein misfolding diseases, especially of diseases which are associated with or caused by misfolding of a protein into an abnormal and/or pathogenic β-sheet, especially in combination with the subsequent protein aggregation, and/or for the prophylactic and/or therapeutic treatment of neurodegenerative diseases, preferably Alzheimer's disease (AD), the agent being different from the trimeric pyrazole compound of the invention. Thus, the inventive trimeric pyrazole compound may be combined with other active agents which are routinely used for the treatment or prevention of a protein misfolding disease.

Moreover, according to a seventh aspect of the present invention, the present invention also refers to a method of treating a human or an animal suffering from a protein misfolding disease. The method comprising administering an efficient amount of at least one trimeric pyrazole compound as defined above.

With regard to the inventive method of treating a human or an animal suffering from a protein misfolding disease, the protein misfolding disease may be associated with or caused by misfolding of a protein into an abnormal and/or pathogenic β-sheet, especially in combination with a subsequent protein aggregation.

As already delineated above, the protein misfolding disease may be selected from the group of neurodegeneration diseases and/or dementia and/or prion diseases, especially Alzheimer's disease (AD), Parkinson's disease, Creutzfeldt-Jakob disease and Huntington's disease.

According to a preferred embodiment, also with respect to the method of the invention, the protein misfolding disease is Alzheimer's disease (AD).

Furthermore, it is also possible according to the inventive concept, that the protein misfolding disease is Diabetes mellitus, especially Diabetes mellitus type II.

According to the present invention, it is preferable that the trimeric pyrazole compound is administered together with at least one pharmaceutically acceptable excipient.

Furthermore, the trimeric pyrazole compound is preferably administered in a pharmaceutically effective amount.

For further explanations, reference is also made to the further aspects of the present invention, which apply accordingly.

Moreover, according to a eighth aspect of the present invention, the present invention also refers to a method of synthesizing and/or producing the trimeric pyrazole compound of the present invention as defined above.

For the case that in the above general formula (I) X denotes a single bond and Y denotes a group of —O⁻ or OH the synthesis is effected by ester cleavage and subsequent deprotection reaction of the compound of general formula (Ia') according to the following reaction scheme:

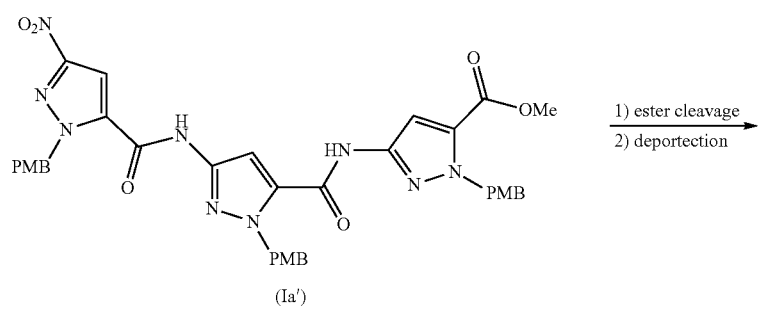

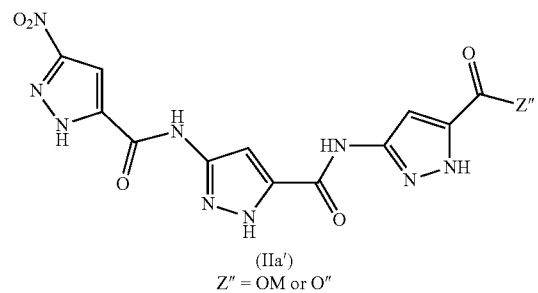

wherein in the general formula (Ia') "PMB" denotes the protective group "para-Methoxybenzyl" and "Me" denotes "methyl" (i.e. CH$_3$) and wherein in the general formula (IIa') "M" denotes hydrogen. The compound of the general formula (Ia') may be obtained according to WO 03/095429 A1, the whole contents of which is hereby incorporated by reference (see especially Example 4, Molecule 12).

For all other cases (i.e. especially if X denotes a single bond or a group of the general formula (II) as defined above and if Y denotes (ii) a (poly)amino acid radical or its salts, especially pharmacologically acceptable salts; its esters, especially alkyl or aryl esters; or its amides or (iii) an amine or diamine radical which is optionally protonated) the reaction is performed according the reaction scheme of FIG. 1C and will be delineated hereinafter. Especially, as it may be derived from FIG. 1C, a compound of the general formula (Ia) comprising protective groups "PMB" as defined above is coupled in the presence of an coupling reagent with a species or molecule H$_2$N—Z' (wherein Z' corresponds to the aforedefined group "Z", however, without the NH-unit, i.e. Z═—NH—Z'), followed by deprotection reaction. The compound of the general formula (Ia) is e.g. obtained by ester cleavage of the aforedefined compound of the general formula (Ia').

Further embodiments, modifications and variations of the present invention are obvious to the skilled practitioner by reading the present specification and/or can be implemented by him without leaving the scope of the present invention.

BRIEF DESCRIPTION OF THE DRAWINGS

FIG. 2A: Aβ (1-40), FIG. 2B: Aβ (1-42).

FIG. 4A shows the inhibition of aggregation and FIG. 4B the disaggregation (10 mM PBS, pH 7.3). For each bar, 6 measurements were averaged.

FIG. 11A; Type B: Trimer-KKKKKG: FIG. 11B; Type C: Trimer-Lys-Che: FIG. 11C).

FIG. 13A shows Aβ lesion control at ~70%, FIG. 13B at ~80% viability.

DETAILED DESCRIPTION OF THE INVENTION

Figure 1A:
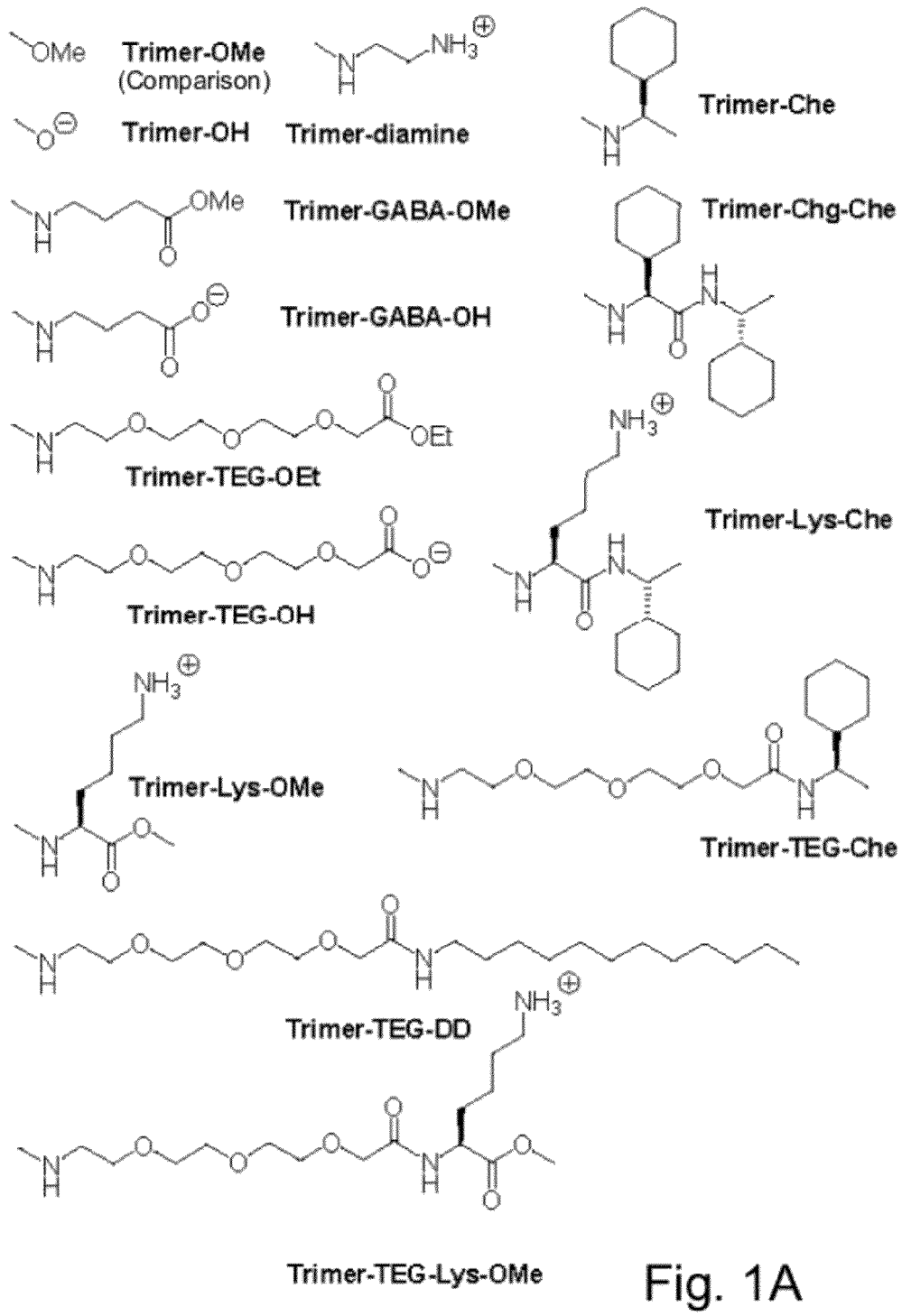
FIGS. 1A and 1B display Lewis structures of unprotected aminopyrazole trimer derivatives with appendices Z. Left: small neutral, anionic and cationic moieties, as well as unpolar and TEG-spacered groups. Right: peptidic attachments.

The present invention is illustrated on the basis of the following detailed explanations and exemplary embodiments as well as experimental data, which, however, do not limit the present invention in any way.

In the following, a detailed description of the inventive concept is given on the basis of applicant's studies and investigations, respectively, comprising experimental data which focus on the specific impact of active agents on the basis of inventive trimeric pyrazole compounds on the misfolding of proteins, especially Aβ and the respective aggregation thereof.

Detailed explanation and exemplification of the present invention:

Introduction and Prior Art.

As delineated before, Alzheimer's disease (AD) is a steadily increasing threat especially for industrialized countries with a growing percentage of old individuals—today an estimated 5.3 million U.S. citizens are suffering from dementia and the number is predicted to quadruple within the next 50 years. Research on potential therapies has been going on for several decades now, without producing one single drug which is able to cure Alzheimer's disease. Since AD is accompanied by many diverse symptoms, numerous avenues have been exploited in the search for a therapy. Antiinflammatory, antihypertensive as well as hypolipidemic agents, passive and active immunization, cholinergic therapies, neuroprotective agents, glutamate receptor antagonists, β- and γ-secretase inhibitors, β-amyloid and Tau aggregation inhibitors, metal chelating agents, monoamine oxidase inhibitors, medicinal plants are only a number of the most prominent classes (Review: Michael S. Wolfe, *Nat. Rev. Drug Disc.* 2002, 1, 859-866). In recent years passive immunization with Aβ-specific antibodies held most promise for a breakthrough; however, the results of phase II clinical trials revealed only moderate to weak effects with a large percentage of treated patients. As a consequence, the call for small molecules was revived/reinitiated.

A plethora of small molecules has been screened in the past 3 decades for their antiaggregation potential against the Alzheimer's peptide (Bisstyrylbenzenes: D. P. Flaherty, S. M. Walsh, T. Kiyota, Y. Dong, T. Ikezu, J. L. Vennerstrom, *J.*

Med. Chem., 2007, 50, 4986-4992). Among these, often colored heterocyclic compounds have been identified, which are in general thought to somehow intercalate between the insoluble cross-β-sheet structure of Aβ fibrils (congo red, rifampicin, melatonin, cucurmin (Yang, F., Lim, G. P., Begum, A. N., Ubeda, O. J., Simmons, M. R., Ambegaokar, S. S., Chen, P. P., Kayed, R., Glabe, C. G., Frautschyj, S. A., and Cole, G. M. (2005) *Curcumin inhibits formation of amyloid oligomers and fibrils, binds plaques, and reduces amyloid in vivo, J. Biol. Chem.* 280, 5892-5901)) (Hydroxyindoles: T. Cohen, A. Frydman-Marom, M. Rechter, E. Gazit, *Biochemistry* 2006, 45, 4727-4735). Zn- and Cu-chelating agents were thought to lower the aggregation tendency of monomeric Aβ strands (clioquinol) (Zn and Cu chelators: Cherny R A, Atwood C S, Xilinas M E, Gray D N, Jones W D, McLean C A, Barnham K J, Volitakis I, Fraser F W, and Kim Y, *Neuron* 2001, 30, 665-676).

Another prevailing class of compounds are peptides, in some cases taken directly from putative nucleation sites within the Aβ molecule (KLVFF derivatives: a) Tjernberg, L. O., Naslund, J., Lindqvist, F., Johansson, J., Karlstrom, A. R., Thyberg, J., Terenius, L., and Nordstedt, C. (1996) *Arrest of β-amyloid fibril formation by a pentapeptide ligand, J. Biol. Chem.* 271, 8545-8548; b) B. M. Austen, K. E. Paleologou, S. A. E. Ali, M. M. Qureshi, D. Allsop, O. M. A. El-Agnaf, *Biochemistry*, 2008, 47, 1984-1992; c) *KLVFF aggregation and gelation*: M. J. Krysmann, V. Castelletto, A. Kelarakis, I. W. Hamley, R. A. Hule, D. J. Pochan, *Biochemistry*, 2008, 47, 4597-4605); however only very few of these compounds stem from rational design with a known structural motif in their complexes with Aβ monomers, oligomers or fibrils. Soto presented the β-sheet breaker LPFFD (iAbeta5) (Soto, C., Sigurdsson, E. M., Morelli, L., Kumar, R. A., Castaño, E. M., and Frangione, B. (1998) *β-Sheet breaker peptides inhibit fibrillogenesis in a rat brain model of amyloidosis: Implications for Alzheimer's therapy, Nat. Med.* 4, 822-826), which retained the high affinity towards the self-complementary LVFFA region, but impaired its β-sheet forming propensity by introducing a proline-kink; the D-peptide MeHN-lvffl-NH$_2$ (PPI-1019) essentially interferes with the aggregation of β-amyloid in the brain and may help promote its clearance (Praecis). Murphy and Kiessling synthesized hybrid peptides built from KLVFF and a highly charged KKKKK or EEEEE terminus (Ghanta, J., Shen, C. L., Kiessling, L. L., and Murphy, R. M. (1996); *A strategy for designing inhibitors of β-amyloid toxicity, J. Biol. Chem.* 271, 29525-29528; T. J. Gibson, R. M. Murphy, *Biochemistry* 2005, 44, 8898-8907). Aggregation of toxic Aβ oligomers is promoted because of increased surface tension.

Another prominent class are alternating N-methylated and nonmethylated peptide amides or esters, presented by Meredith, Hughes and Kapurniotu (Gordon, D. J., and Meredith, S. C. (2003) *Probing the role of backbone hydrogen bonding in β-amyloid fibrils with inhibitor peptides containing ester bonds at alternate positions, Biochemistry* 42, 475-485; Hughes, E., Burke, R. M., and Doig, A. J. (2000) *Inhibition of toxicity in the β-amyloid peptide fragment β-(25-35) using N-methylated derivatives—A general strategy to prevent amyloid formation, J. Biol. Chem.* 275, 25109-25115; Kapurniotu, A., Schmauder, A., and Tenidis, K. (2002) *Structurebased design and study of nonamyloidogenic, double N-methylated IAPP amyloid core sequences as inhibitors of IAPP amyloid formation and cytotoxicity, J. Mol. Biol.* 315, 339-350). These are able to cap growing β-sheets, without the ability of crosslinking because their back is blocked for hydrogen bonding due to the sterically demanding N-methyl groups or ester oxygens. They have recently been optimized with respect to their antiaggregatory capacity by introduction of 3 cyclohexylglycine units and reached nanomolar IC$_{50}$ values. The so far most potent compound is also thought to accelerate Aβ self-assembly and thereby deplete the level of neurotoxic Aβ-oligomers (N. Kokkoni, K. Stott, H. Amijee, J. M. Mason, A. J. Doig, *Biochemistry* 2006, 45, 9906-9918).

Other examples comprise the small molecule homotaurin, which disrupts complexes between Aβ and glucosaminoglycans. Scyllo-inositol appears to bind oligomers of Aβ42, preventing them from damaging synapses. Oligomer-specific Aβ antibodies indicated that scyllo-inositol appears to increase the number of monomers and trimers while reducing the amount of larger oligomeric species, such as 40 mers (a) McLaurin, J., Goloumb, R., Jurewicz, A., Antel, J. P. & Fraser, P. E. *Inositol stereoisomers stabilize an oligomeric aggregate of Alzheimer amyloid beta peptide and inhibit Aβ-induced toxicity. J. Biol. Chem.* 2000, 275, 18495-18502; b) J. McLaurin, M. E. Kierstead, M. E. Brown, C. A. Hawkes, M. H. L. Lambermon, A. L. Phinney, A. A. Darabie, J. E. Cousins, J. E. French, M. F. Lan, F. Chen, S. S. N. Wong, H. T. J. Mount, P. E. Fraser, D. Westaway, P. St. George-Hyslop; *Nat. Med.* 2006, 12, 801-808).

A recent approach comes from Willboldt et al., who selected potent Aβ binders from D-peptide libraries by phage display (*D-peptides by phage display*: K. Wiesehan, K. Buder, R. P. Linke, S. Patt, M. Stoldt, E. Unger, B. Schmitt, E. Bucci, D. Willbold, *Selection of D-amino-acid peptides that bind to Alzheimer's disease amyloid peptide Abeta(1-42) by mirror image phage display, ChemBioChem* 2003, 4, 748-753).

Surprisingly little knowledge/information, however, is available on the exact mechanism of action for most Aβ complexing agents, even less on structural details. To the best of applicant's knowledge, the only case is Sato's concept of β-sheet packing: peptide inhibitors based on a GxFxGxF framework disrupt sheet-to-sheet packing and inhibit the formation of mature Aβ fibrils (Sato, T, Kienlen-Campard, P., Ahmed, M., Liu, W, Li, H. L., Elliott, J. I., Aimoto, S., Constantinescu, S. N., Octave, J. N, and Smith, S. O. (2006) *Inhibitors of amyloid toxicity based on β-sheet packing of Aβ(1-40) and Aβ(1-42), Biochemistry* 45, 5503-5516). This strategy was developed from inspection of solid state NMR structures of amyloid fibrils and confirmed by $^{13}$C NMR spectroscopy for the best candidate peptide in its direct complex with Aβ1-40. In this context, work by Bitan is also interesting, who identified Met-35 as a structural switch in Aβ aggregation (Bitan, G., Tarus, B., Vollers, S. S., Lashuel, H. A., Condron, M. M., Straub, J. E., and Teplow, D. B. (2003) *A molecular switch in amyloid assembly: Met(35) and amyloid β-protein oligomerization, J. Am. Chem. Soc.* 125, 15359-15365). A new aspect comes from recent observations, that many small molecules which form colloids inhibit pathological peptide aggregation (*Colloidal inhibition*: B. Y. Feng, B. H. Toyama, H. Wille, D. W. Colby, S. R. Collins, B. C. H. May, S. B. Prusiner, J. Weissman, B. K. Shoichet, *Nat. Chem. Biol.* 2008, 4, 2-3).

Aminopyrazoles are rationally designed β-sheet ligands with a specific DAD-sequence of hydrogen bond donors and acceptors, complementary to that of a β-sheet (T. Schrader, C. Kirsten, *J. Chem. Soc., Chem. Commun.* 1996, 2089; T. Schrader, C. N. Kirsten, *J. Am. Chem. Soc.* 1997, 119, 12061-12068). Derivatives were synthesized and also evaluated on the solid phase (a) P. Rzepecki, M. Wehner, O. Molt, R. Zadmard, T. Schrader, *Synthesis* 2003, 1815-1826; b) Kateřina Černovskà, Miriam Kemter, Hans-Christoph Gallmeier, Petra Rzepecki, Thomas Schrader and Burkhard König, *Org. Biomol. Chem.* 2004, 2, 1603-1611; c) P. Rzepecki, H. Gallmeier, N. Geib, Katarina Cernovska, B. König, T. Schrader, *J. Org. Chem.* 2004, 69, 5168-5178; d) P. Rzepecki, N. Geib, M. Peifer, F. Biesemeier, T. Schrader, *J. Org. Chem.* 2007, 72, 3614-3624). Direct interaction of dimeric and trimeric aminopyrazole derivatives with the mouse prion protein as well as with Aβ(1-42) was shown and characterized by SDS-PAGE, FCS, AUC, density gradient centrifugation as well as HRMS. β-sheet recognition as well as the individual strength of all hydrogen bonds involved were studied in great detail by R2PI spectroscopy on a cooled argon jet stream (a) P. Rzepecki, L. Nagel-Steger, S. Feuerstein, U. Linne, O. Molt, R. Zadmard, K. Aschermann, M. Wehner, T. Schrader, D. Riesner, *J. Biol. Chem.* 2004, 279, 47479-47505; b) H. Fricke, A. Funk, T. Schrader, M. Gerhards, *J. Am Chem. Soc.* 2008, 130, 4692-4698; c) H. Fricke, A. Gerlach, C. Unterberg, M. Wehner, T. Schrader, M. Gerhards, *Angew. Chem.* 2009, 48, 900-904).

Results and Discussion.

In a misfolded extended peptide strand, amino acid sidechains protrude horizontally (orthogonal to) from the vertical peptidic backbone β-sheet; complexed β-sheet ligands will therefore automatically place their recognition sites close to the typical functional groups found in proteinogenic amino acid residues. It was therefore attempted to match the main classes of amino acids with complementary recognition sites on the complexing aminopyrazole trimers, and to vary sizes and distances from their attachment point. Scheme 1 shows an overview about all synthesized derivatives and their classification:

C-Terminal Appendices to the Trimeric Aminopyrazole.

1. Lysine and arginine binders contain carboxylate anions, at varying distances from the heterocyclic core. 2. Aspartate and Glutamate binders were introduced as ammonium cations, placed remote and close to the aminopyrazoles; the pentavalent derivatives are probes for a potential complexation of the glutamate-22 ladder found in the all solid state NMR structures. 3. Polar residues with XH-groups such as serine and tyrosine are able to form multiple hydrogen bonds with ethyleneglycol moieties; the TEG (triethyleneglycol) unit also serves as a water-soluble linker for remote recognition events. 4. Unpolar residues are matched by flexible branched hydrocarbons as found in cyclohexylglycine, already introduced by the Stott group (N. Kokkoni, K. Stott, H. Amijee, J. M. Mason, A. J. Doig, *Biochemistry* 2006, 45, 9906-9918). 5. Characteristic peptide fragments within the Aβ molecule known for efficient self-recognition were finally introduced as peptidic address labels.

Synthesis.

The trimeric aminopyrazole core structure was elongated with a variety of additional binding sites. To this end, its C-terminal carboxylic acid was connected to the respective amines by way of a peptide bond. Conventional coupling reagents comprised EDC/HOBt, HCTU/Cl—HOBt and Mukaiyama's reagent, which produced the hybrid compounds in high yields. In an economic fashion, all protecting groups of the tether were finally cleaved by TFA together with all PMB-moieties on the aminopyrazole nuclei. Peptidic tethers were first synthesized by manual solid phase peptide synthesis (SPPS) on a Wang resin, followed by covalent attachment at the aminopyrazole trimer (HBTU, DIEA). Final deblocking of all acid-labile protecting groups at 70° C. for ~3 hrs furnished, after precipitation and recrystallization from ether, analytically pure final products 3a-z. All these new trimeric aminopyrazoles are soluble in DMSO, the most polar even in water. They are listed in Table 1, together with absolute yields and their solubilities.

Figure 1B:
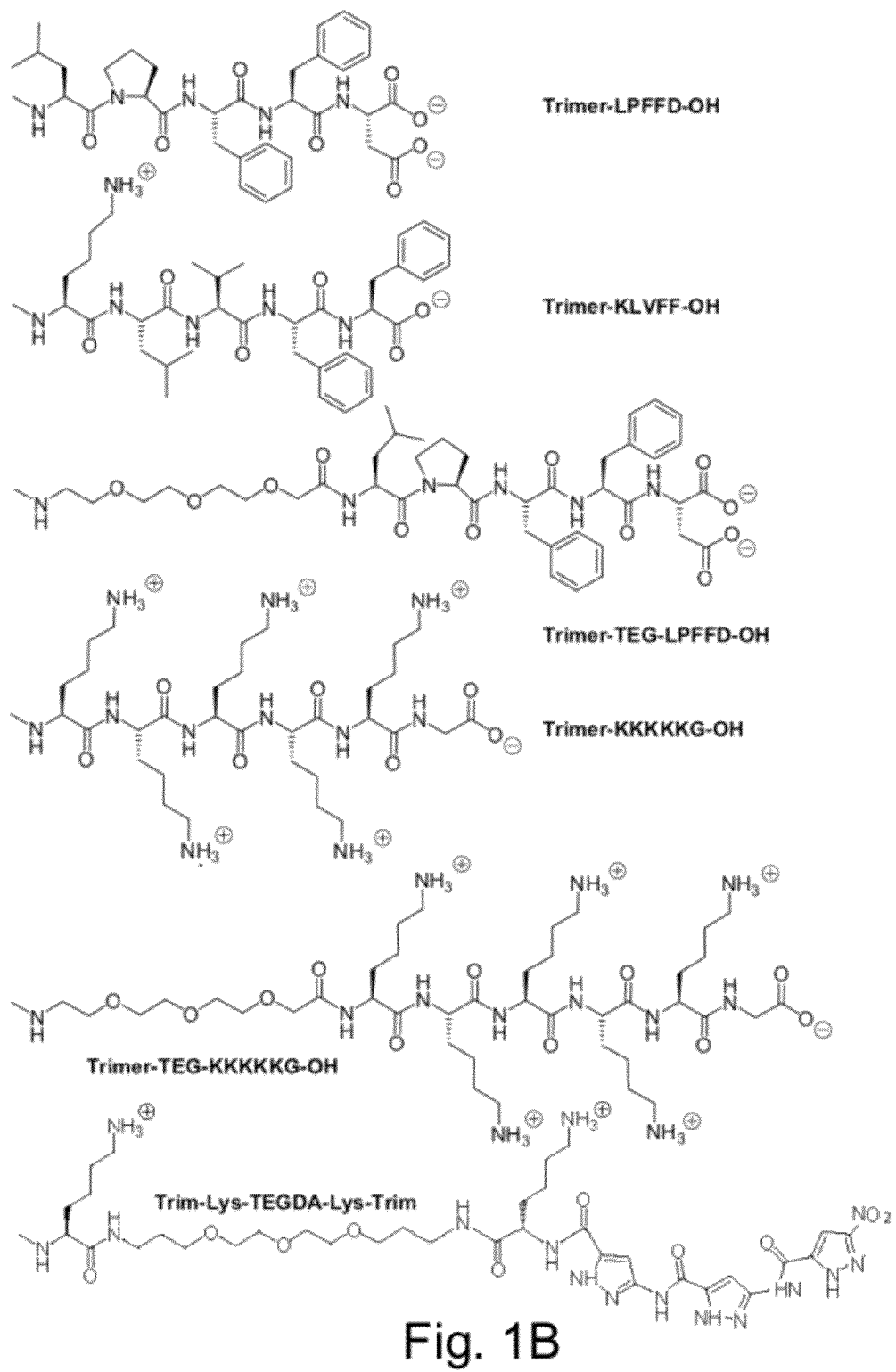

FIGS. 1A and 1B display Lewis structures of unprotected aminopyrazole trimer derivatives with appendices Z. Left: small neutral, anionic and cationic moieties, as well as unpolar and TEG-spacered groups. Right: peptidic attachments.

Figure 1C:
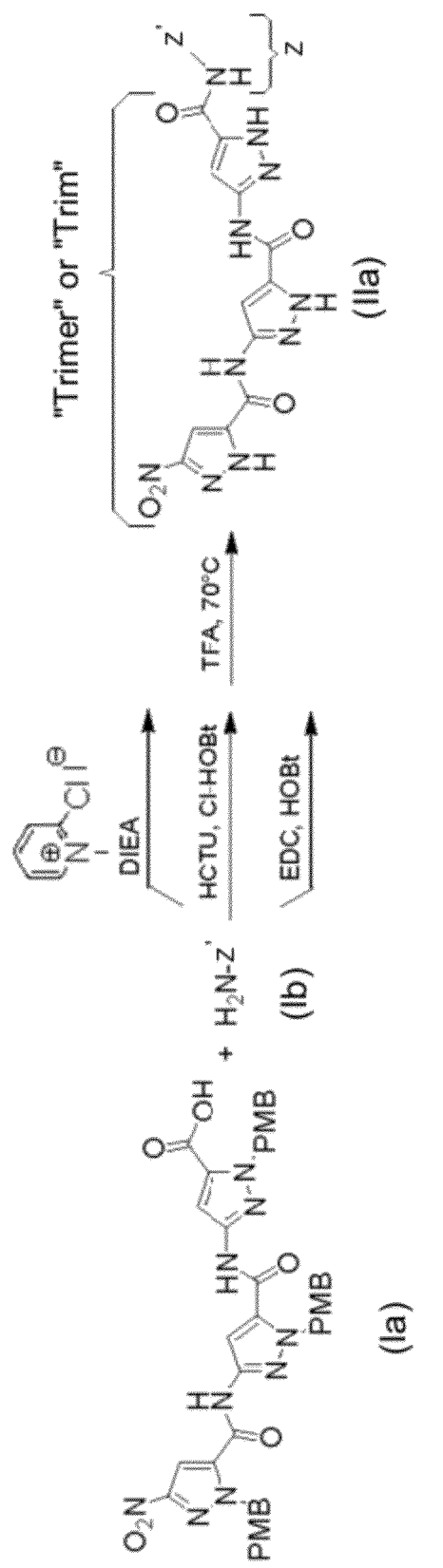
FIG. 1C shows a synthetic access to the new C-terminally modified aminopyrazole trimers via peptide coupling of various amines onto the PMB-protected trimer and final total deprotection.

FIG. 1C shows a synthetic access to the new C-terminally modified aminopyrazole trimers via peptide coupling of various amines onto the PMB-protected trimer and final total deprotection.

TABLE 1

Unprotected aminopyrazole trimers for in-vitro aggregation experiments.

| Entry | Aminopyrazole | Coupling | Deprotection | Solubility[a] | milogP | TPSA |
|---|---|---|---|---|---|---|
| 1 | Trimer-OMe | — | 69% | b | −0.26 | 216.37 |
| 2 | Trimer-OH | — | 93% | b | −0.52 | 227.37 |
| 3 | Trimer-diamine | 82% | 51% | b | −2.09 | 245.19 |
| 4 | Trimer-GABA-OMe | 57% | 76% | b | −0.80 | 245.47 |
| 5 | Trimer-GABA-OH | — | 78% | b | −1.11 | 256.47 |
| 6 | Trimer-Che | 83% | 82% | b | +1.72 | 219.17 |
| 7 | Trimer-Chg-Che | 48% | 89% | b | +3.10 | 248.27 |
| 8 | Trimer-Lys-Che | 88% | 66% | a | +0.66 | 274.30 |
| 9 | Trimer-TEG-OEt | 80% | 98% | b | −1.08 | 273.17 |
| 10 | Trimer-TEG-OH | — | 94% | b | −2.07 | 284.17 |
| 11 | Trimer-Lys-OMe | 63% | 96% | a | −1.20 | 271.50 |
| 12 | Trimer-TEG-Che | 75% | 72% | b | +0.41 | 275.97 |
| 13 | Trimer-TEG-Dodecyl | 75% | 70% | b | +3.27 | 275.97 |
| 14 | Trimer-TEG-Lys-OMe | 82% | 91% | a | −2.51 | 328.30 |
| 15 | Trimer-LPFFD-OH | SPPS[b] | >70%* | b | +0.58 | 389.34 |
| 16 | Trimer-TEG-KLVFF-OH | SPPS | >70%* | b | −1.83 | 455.68 |
| 17 | Trimer-TEG-LPFFD-OH | SPPS | >70%* | b | −3.32 | 441.10 |
| 18 | Trimer-KKKKKG-OH | SPPS | >70%* | a | −5.58 | 532.07 |
| 19 | Trimer-TEG-KKKKKG-OH | SPPS | >70%* | a | −5.82 | 588.87 |
| 20 | Trim-Lys-TEGDA-Lys-Trim | 52% | 97% | a | −4.10 | 576.28 |

[a] a) water (4.95 mM stock solution); b) DMSO (4.95 mM stock solution), dilutable to 200 µM in water/DMSO (90:10);
[b] SPPS: solid phase peptide synthesis;
[c] two steps (mild cleavage from resin followed by PMB deprotection with hot TFA).

Aggregation Studies.

The influence of the new β-sheet ligands, based on the aminopyrazole-trimer, on the Aβ self-assembly process was first studied kinetically. Reference curves were obtained independently for both Aβ (1-40) and Aβ (1-42). In a typical experiment, one third (⅓) equivalent of thioflavine T was added to a solution of monomeric Aβ in PBS buffer, prepared in HFIP. The increase in ThT fluorescence was monitored over time, as a measure of the total amount of accumulating aggregates. As expected Aβ (1-42) commenced immediately after dilution with fibril formation, as opposed to Aβ(1-40), which showed the well-known lag phase of ~24 hrs. Both peptides reached a plateau after ~3 days, which was set as standard time period for all consecutive aggregation assays.

Kinetics of Aggregation Inhibition by Trimeric Aminoypyrazoles.

Care was taken to eliminate fluorescence changes induced by any other events than the aggregation process; thus each ligand was separately shown to be non-fluorescent and not to alter Tht fluorescence in mixtures. Controls with pure Aβ were identical in peptide concentration as well as buffer and solvent composition. Aβ (1-40): Representative kinetic curves are shown in FIG. 2. Interestingly, no ligand changes the 24 h lag phase, but instead proceeds with distinctly different velocity before it reaches the aggregation maximum, the trimer prototype being the slowest. Aβ (1-42): Much more impressive is the inhibitory influence of the trimeric ligands on the aggregation kinetics of the full-length Aβ (1-42). The trimer itself is outperformed in its aggregation decelerating effect by the corresponding derivative with a distant lysine, whereas the related compound with a proximal lysine goes to the other extreme and greatly expedites the Aβ aggregation process. Obviously, the location of a single lysine residue on the aminopyrazole ligand has a profound effect on complex formation with and subsequent misfolding of the Alzheimer's peptide.

Figure 2A:
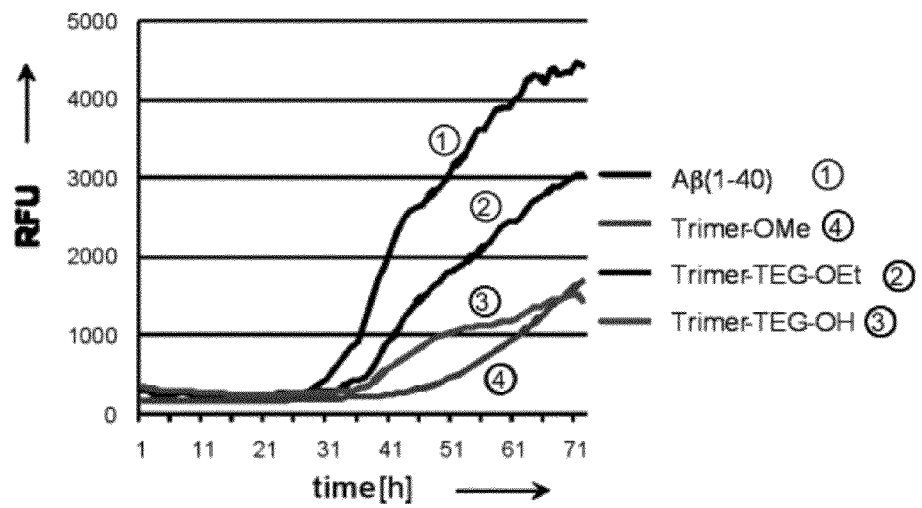
FIGS. 2A and 2B show the kinetics of Aβ aggregation in PBS buffer (pH 7.3) in the absence and presence of selected trimeric pyrazole inhibitors.
Figure 2B:
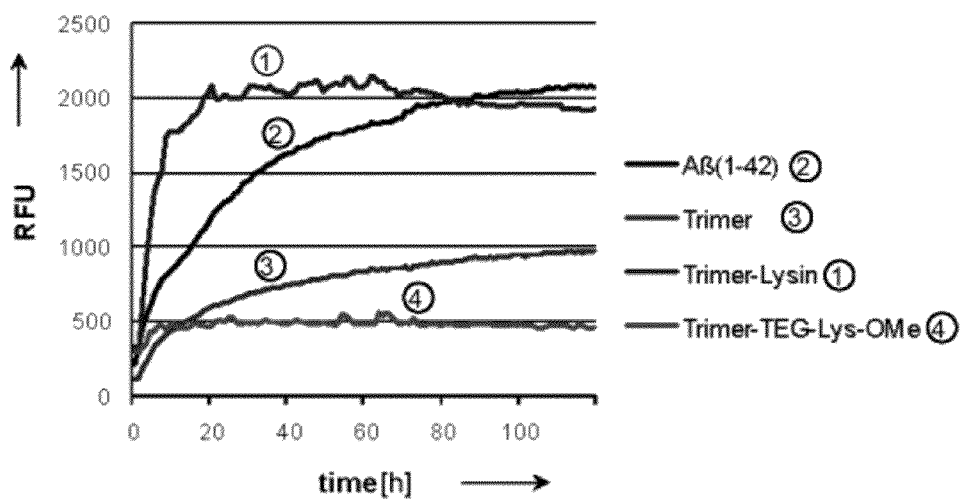

FIGS. 2A and 2B show the kinetics of Aβ aggregation in PBS buffer (pH 7.3) in the absence and presence of selected trimeric pyrazole inhibitors; FIG. 2A: Aβ (1-40), FIG. 2B: Aβ (1-42).

Kinetics of Aβ Disaggregation by Trimeric Aminopyrazoles.

Figure 3:
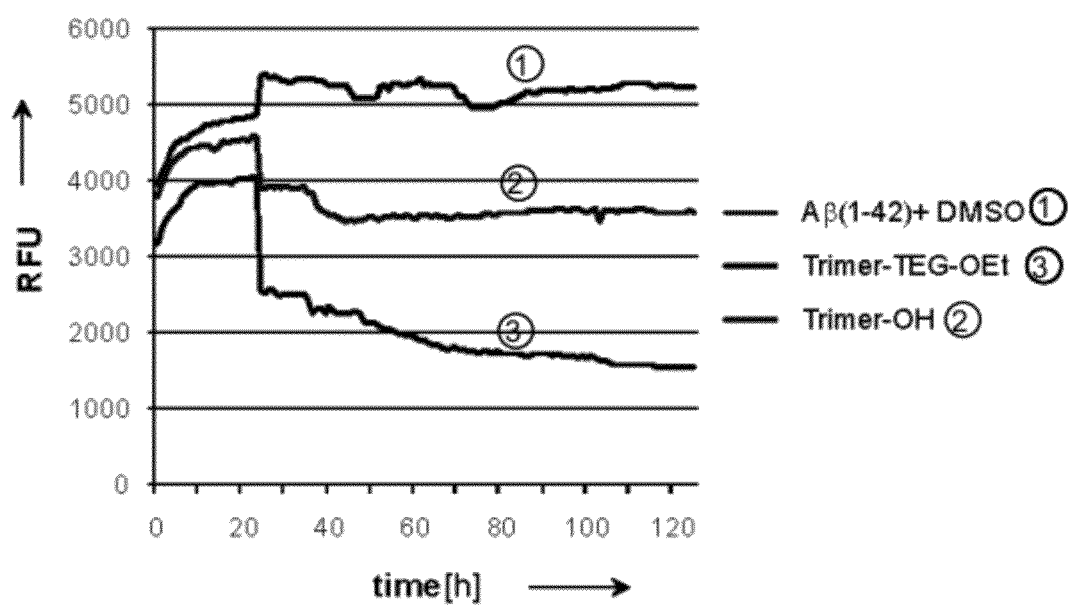
FIG. 3 discloses the kinetics of Aβ disaggregation effected by addition of a 6-fold excess of trimeric aminopyrazole inhibitors to preformed fibrillar aggregates (33 μM in PBS).

Applicant discovered that the parent trimeric aminopyrazole does not only bind to growing Aβ ensembles, but also strongly interacts with preformed Aβ fibrils, and leads to their disassembly. The kinetics of this interesting process reveal a two-phase event, with a rapid disaggregation during the first few minutes, and a slow dissolution within the next 5 days, until the overall equilibrium is reached (FIG. 3). In combination with sedimentation analyses, applicant proposes that the first disaggregation phase involves release of protofibrils from mature fibrils, whereas the second slower disassembly may be characterized by further conformational changes with loss of the well-ordered β-sheets.

FIG. 3 discloses the kinetics of Aβ disaggregation effected by addition of a 6-fold excess of trimeric aminopyrazole inhibitors to preformed fibrillar aggregates (33 μM in PBS).

Equilibrium of Aβ Aggregation Inhibited by Trimeric Aminopyrazoles.

After 72 h, the aggregation process has reached a maximum in the absence or presence of any trimeric ligand, even for the slow Aβ (1-40) peptide. The respective equilibrium concentration is then indicated by the relative fluorescence intensity reached at the end point. The full series of new aminopyrazole trimer derivatives was subjected to ThT inhibition experiments and the final equilibrium was analyzed by comparison of the respective fluorescence intensities of intercalated dye at 482 nm (exc. at 442 nm). FIG. 4 reveals a significant structure-activity relation for Aβ (1-42): structurally related compounds in general display comparable inhibition properties. Two classes of the modified derivatives surpass the original trimer activity: Trimer-CHE/Trimer-Lys-CHE/Trimer-LPFFD with attached extended lipophilic groups and Trimer-TEG-Lys/Trimer-KKKKG with a distant or multiple lysine residues. Their proposed mechanism of action is discussed within the next chapters together with all the other biophysical, biochemical as well as modeling data.

Equilibrium of Aβ Disaggregation by Trimeric Aminopyrazoles.

Starting from preformed fibrils, the disassembly process was also monitored with the full series of modified trimeric aminopyrazoles. Surprisingly, the inhibition pattern (left) looks quite similar to the disaggregation pattern (right), in several cases, that total percentage of ThT rest fluorescence is identical. In other words, little difference is observed between the end points of aggregation assays, in which the ligand inhibits de novo aggregation starting from monomeric Aβ molecules, and those experiments, which require disaggregation of preformed fibrils by externally added ligand. Experimental evidence is thus provided for the fact, that aminopyrazole ligands operate in a fully reversible fashion, and reach an open equilibrium when the thermodynamically most favorable complex is formed.

Figure 4A:
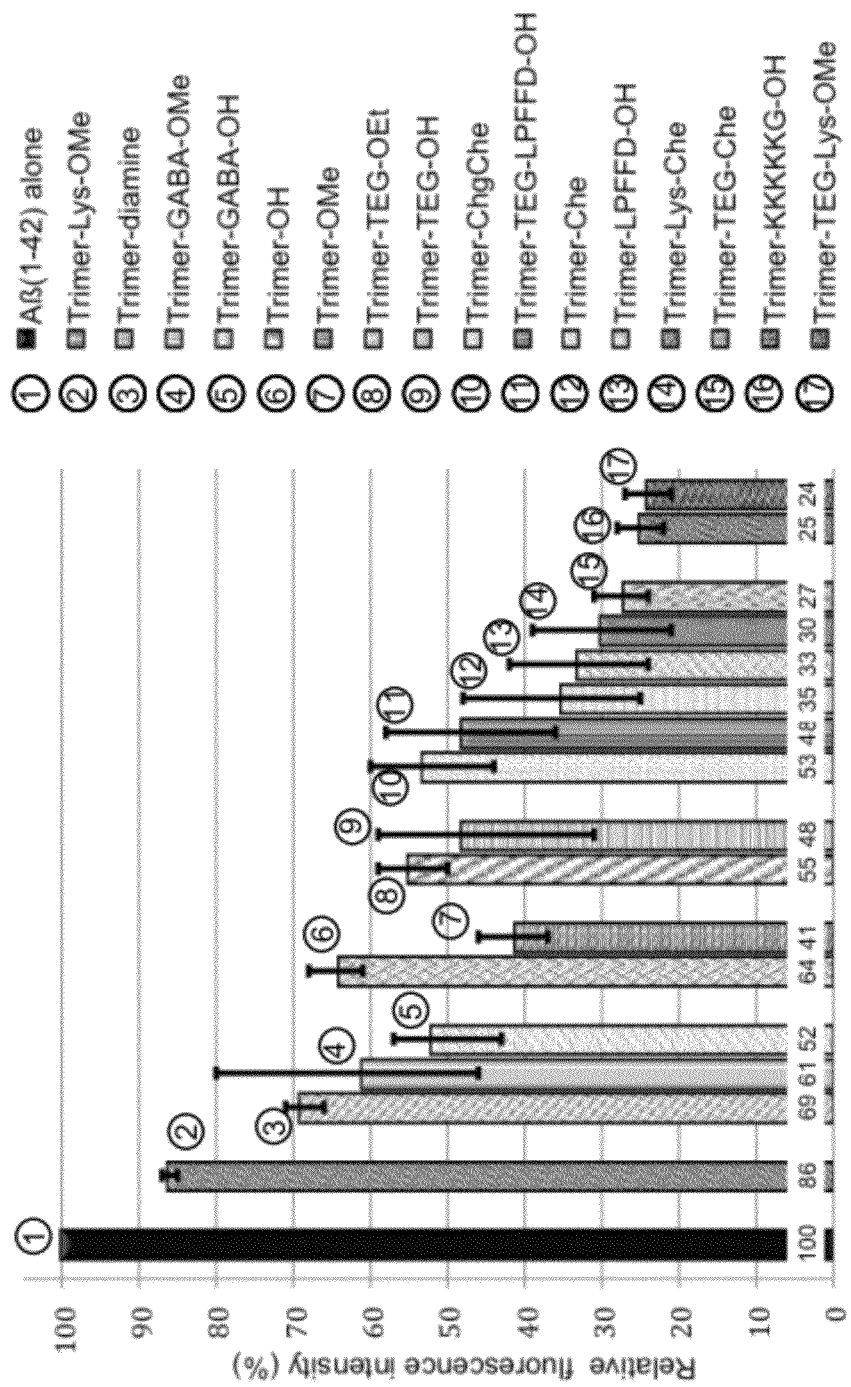
FIGS. 4A and 4B show the equilibrium of 33 μM Aβ42 aggregation (FIG. 4A) vs. disaggregation (FIG. 4B) in the absence or presence of trimeric aminopyrazole inhibitors (each at 198 μM)
Figure 4B:
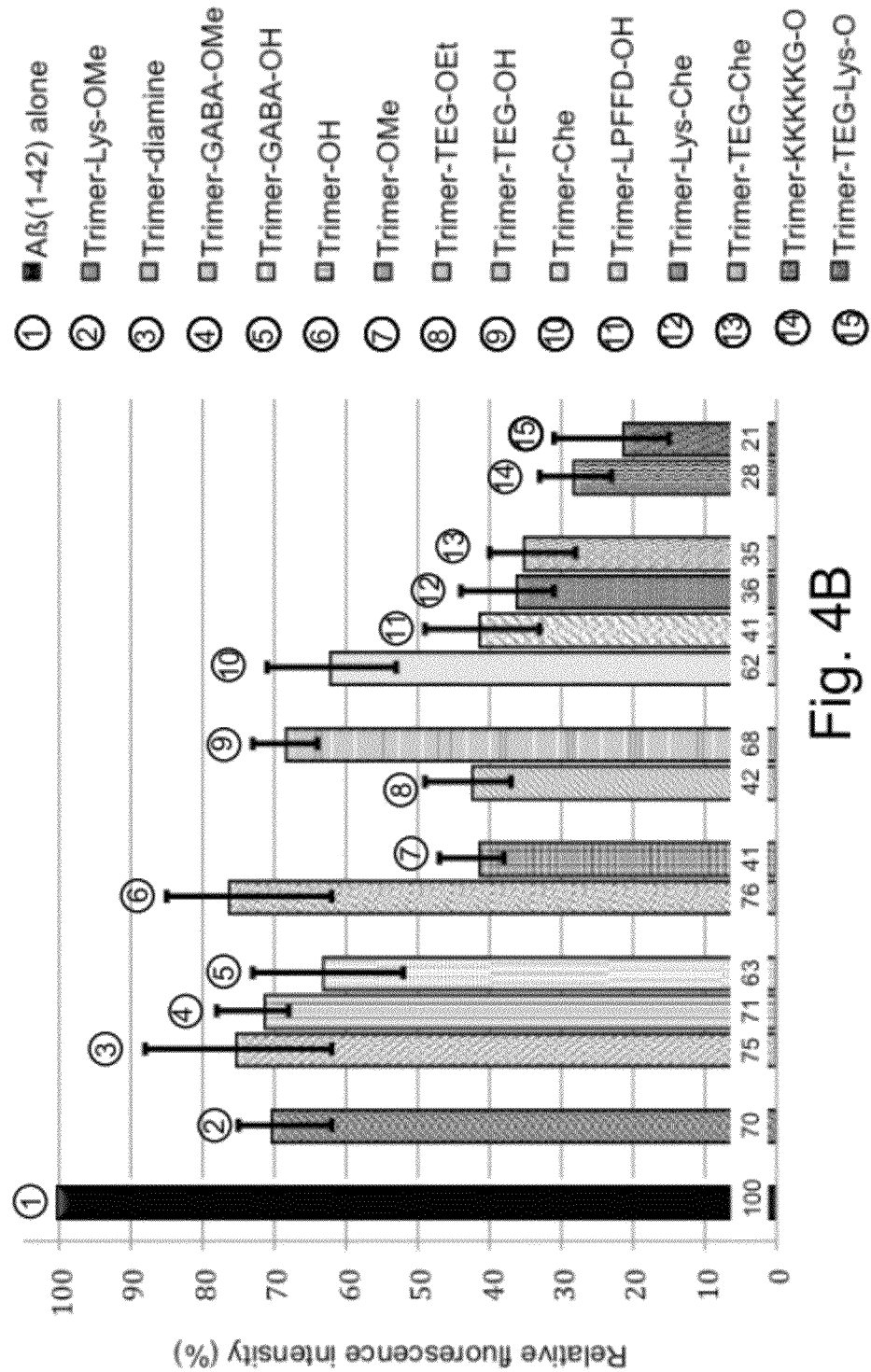

FIGS. 4A and 4B show the equilibrium of 33 μM Aβ42 aggregation (FIG. 4A) vs. disaggregation (FIG. 4B) in the absence or presence of trimeric aminopyrazole inhibitors (each at 198 μM); FIG. 4A shows the inhibition of aggregation and FIG. 4B the disaggregation (10 mM PBS, pH 7.3). For each bar, 6 measurements were averaged.

Anchor Point for Docking Experiments.

In the past, detailed conformational NMR analyses between aminopyrazole ligands and the model peptide KLVFF, a putative nucleation site in Aβ, furnished strong hints for direct hydrogen bonds between ligand and peptidic backbone (P. Rzepecki, T. Schrader, *J. Am. Chem. Soc.* 2005, 127, 3016-3025). In addition, upfield shifts of aromatic protons in both phenylalanines indicated π-stacking interactions. Energy-minimizations and subsequent Monte-Carlo simulations in water converged on a complex structure with two consecutive phenylalanines sandwiching an aminopyrazole nucleus, which effectively shielded it from the aqueous solvent. Recent MD simulations between the trimeric aminopyrazole and an Aβ monomer residing in its folded fibril conformation (solid state structure) demonstrated the KLVFF sequence to be superior over all other complexation sites. It was therefore attempted to correlate altered complexation behavior and influence on aggregation of the above-mentioned new series of modified aminopyrazole trimers with specific additional noncovalent interactions predicted from docking experiments of these β-sheet ligands onto the Aβ fibril. Since KLVFF (residues 16-20) represents the starting point of the well ordered part of the Aβ sequence, covalently attached C-terminal appendices of the aminopyrazole trimer will be able to exploit the maximum contact area of the fibril's top face.

CD measurements of all water-soluble trimeric ligands in 1:1-mixtures with Aβ(1-42) reveal that in most cases, a new CD band evolves at 260-320 nm with a positive maximum at 280 nm, typical for complexes of aromatic moieties (Phe: 260-270 nm; Tyr 270-280 nm; Trp: 290-300 nm). Since at this wavelength aminopyrazole ligands are CD-silent, applicant attributes the new band to tight complex formation between aromatic units in Aβ and ligand, most likely between the two consecutive phenylalanines and the pyrazole nuclei.

This structural motif offers a unique opportunity for docking experiments, which were hence performed on the hydrogen-bonded complex between aggregated Aβ (Lührs structure) and ligand. Both were involved in backbone recognition, starting from the Phe-Phe pair which locks the first aminopyrazole in a sandwich arrangement.

Intriguingly, several additional favorable interactions were found, which were typical for each major class of trimer tethers. They will be discussed along with all biophysical experiments conducted for each group of trimers.

Figure 5:
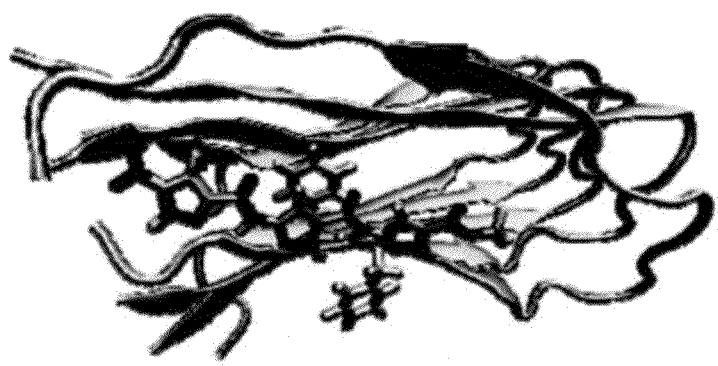
FIG. 5 displays aMD simulation of the complex between Aβ and the parent aminopyrazole trimer (10 ns).

In force-field calculations, the trimer itself forms the characteristic DAD pattern of multiple hydrogen bonds towards the solvent-exposed top face of the KLVFF backbone and simultaneously stacks its pyrazole nuclei with both phenylalanine units in form of a hydrophobic cleft (Trimer-OMe, Trimer-OH, FIG. 5).

FIG. 5 displays aMD simulation of the complex between Aβ and the parent aminopyrazole trimer (10 ns).

The trimeric aminopyrazole skeleton is able to reduce the total amount of Aβ aggregates (30 μM) to ~40% at a 6-fold excess, but to <20% at a 10:1 ratio (inhibition 17%, disaggregation: 25%). This corresponds to an estimated dissociation constant of the complex in the low micromolar range (2 μM $K_d$ in PBS buffer). Interaction of the new trimeric lead structure and monomeric as well as polymeric Aβ was further studied with fluorescence correlation spectroscopy (FCS), sedimentation analysis (SA, based on analytical ultracentrifugation) and Transmission Electron Microscopy (TEM).

Figure 6:
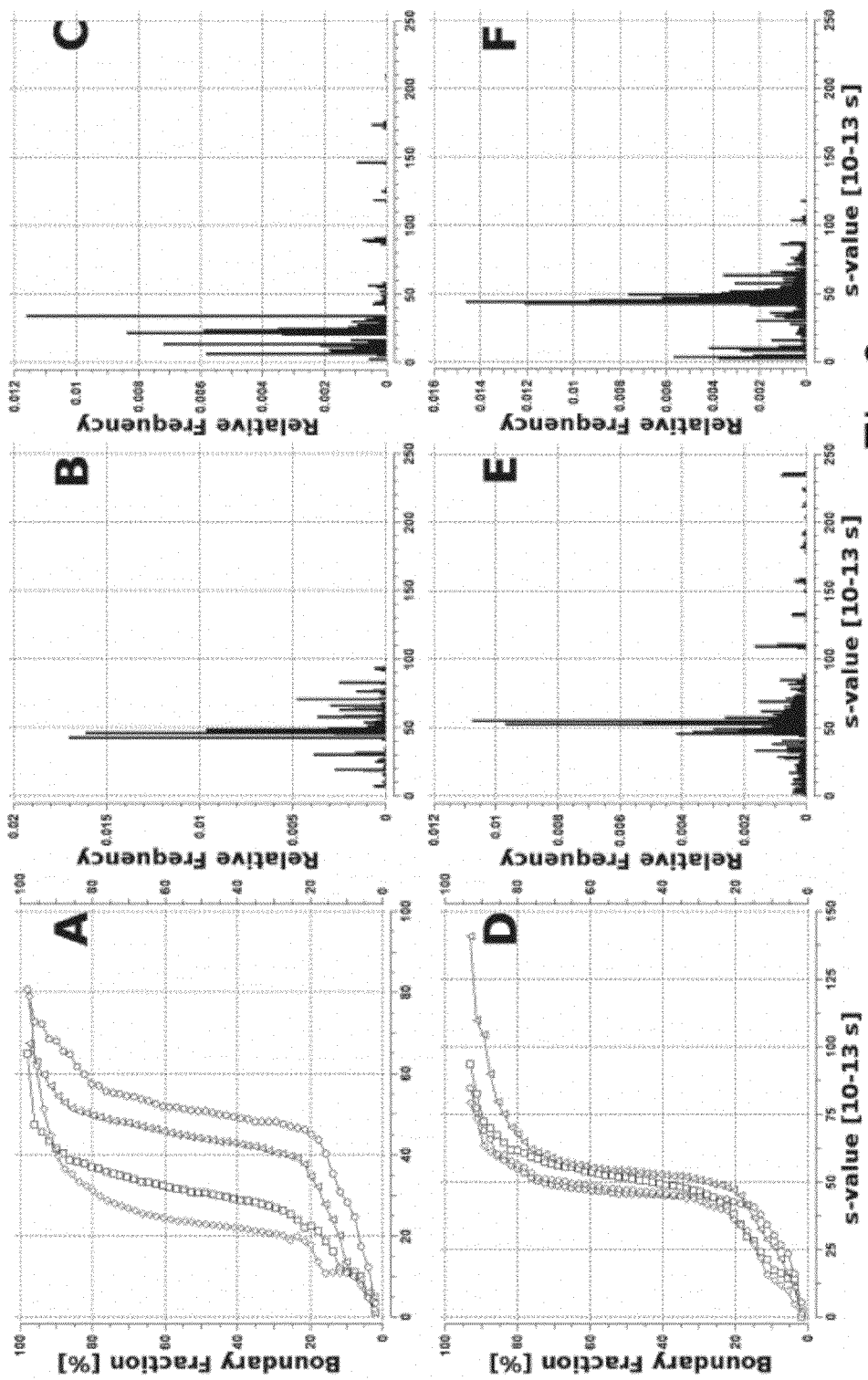
FIG. 6A to 6F show the results of sedimentation velocity centrifugation: s-value-distributions of Aβ samples in the presence of Trimer-OH (FIG. 6A, FIG. 6B, FIG. 6C) vs. Trim-TEG-OEt (FIG. 6D, FIG. 6E, FIG. 6F).

In a standard FCS experiment a 5 nM Oregon-Green-labeled Aβ solution was prepared in PBS buffer with ~3% DMSO. Trimer-OMe was added at 100 nM and reduced the peaks x height value to ~25% of the control. Since the number of peaks remained unchanged, their molecular weight was greatly reduced. Independent confirmation came from sedimentation analyses with Oregon-Green-labeled Aβ: Coefficients for pure Aβ were above 50 S, whereas those for its complex with Trimer-OH continuously decreased in a dose-dependant manner down to 25 S, corresponding to a 50% molecular weight reduction (FIG. 6). It should be noted, that Trimer-OH itself also tends to self-associate; its sharp radial distribution suggests formation of micelles of ~10 S size. This is not surprising, because it comprises a flat arrangement of unpolar aromatics adorned with polar groups for extensive hydrogen bonding. Finally, TEM pictures were obtained from mature Aβ fibrils (>600 nM) as well as globular particles (3-30 nm) grown in the absence of aminopyrazole ligands.

Figure 7:
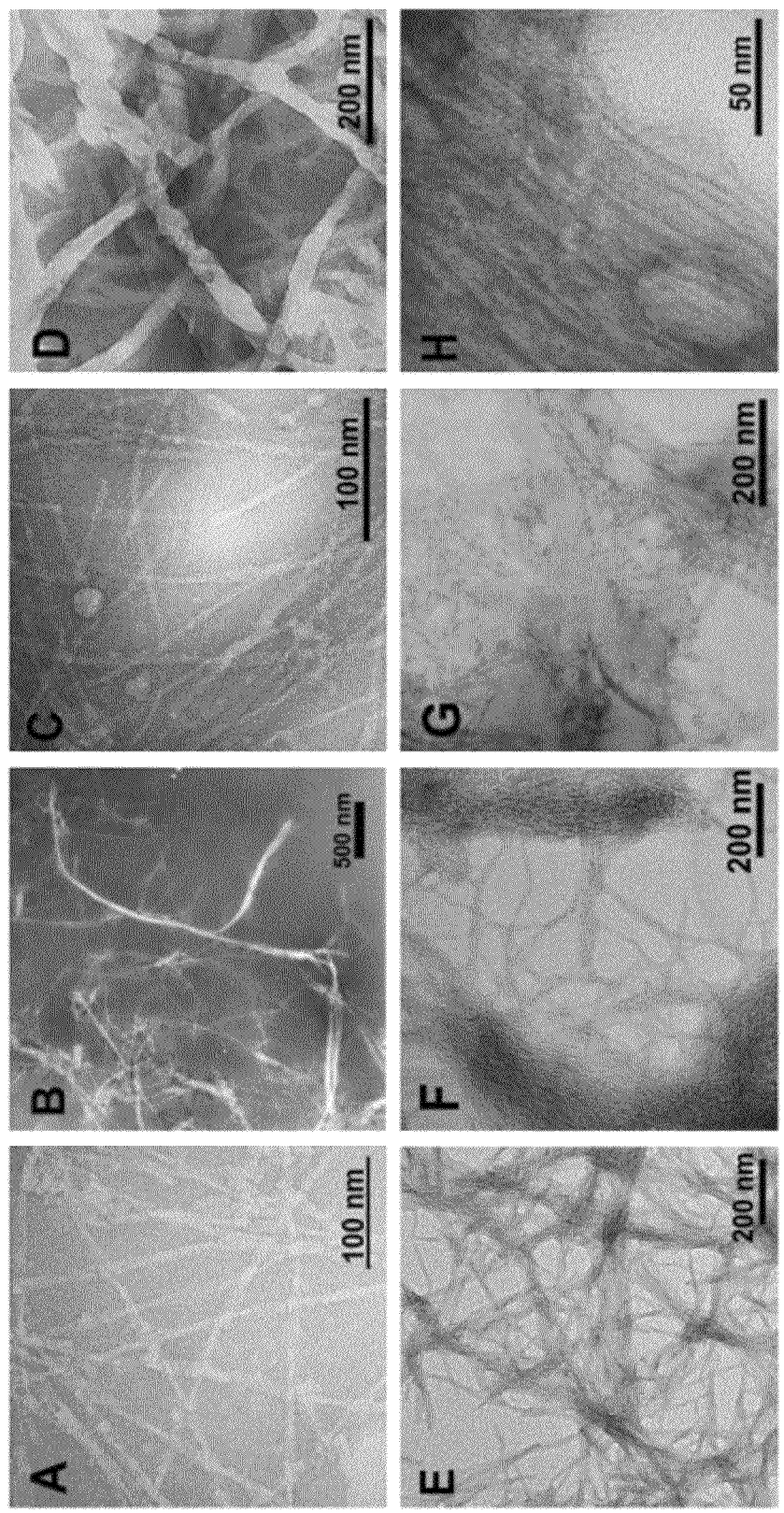
FIG. 7 shows TEM pictures. A: Aβ(1-42) fibrils. B-F: Aβ(1-42) mixtures (20 μM) with aminopyrazole trimer derivatives (100 μM). B: Trim-OMe; C: Trim-OH, D: Trim-Che; E: Trim-Lys-OMe; F: Trim-TEG-Lys-OMe; G: Trim-TEG-OEt; H: Trim-TEG-OH.

While the diameter of the twisted ribbons from pure Aβ corresponds to 10 nm, thin filaments were produced in the presence of the trimeric ligand (5 nm), and the number of mature fibrils was greatly reduced (FIG. 7). Applicant concludes that the trimer seems to break the mature fibrils into protofilaments by a combination of backbone recognition and hydrophobic interactions. In a preliminary cell culture assay with PC-12 cells, inhibition of Aβ(1-42)-induced toxicity was very moderate (<10% viability increase, FIG. 13). Since Trimer-OH/OMe contain only the trimeric aminopyrazole core unit, their interaction profile sets the standard for all other modified derivatives of this investigation.

FIG. 6A to 6F show the results of sedimentation velocity centrifugation: s-value-distributions of Aβ samples in the presence of Trimer-OH (FIG. 6A, FIG. 6B, FIG. 6C) vs. Trim-TEG-OEt (FIG. 6D, FIG. 6E, FIG. 6F). FIG. 6A, FIG. 6D: Van-Holde-Weischet distribution plots, G(s), for aggregation mixtures of Aβ(1-42)/Aβ42-OG (17.5 nM/3.5 μM) in 10 mM NaP$_i$, pH 7.4, 4% DMSO with 0 μM (control, circles), 66 μM (triangles), 133 μM (squares), and 200 μM Trimer derivative (diamonds). Samples were incubated slightly agitated at RT for 5 d prior centrifugation at 20,000 rpm, 20° C. FIG. 6B, FIG. 6E: s-value distributions of the control experiments as determined by 2D-SA and Monte Carlo analysis. FIG. 6C, FIG. 6F: s-value distributions of experiments with 200 μM Trimer derivative after 5 d of incubation as determined by 2D-SA and Monte Carlo analysis.

Small charged extensions at the trimer's C-terminus are too short for specific interactions with other amino acid residues in the neighborhood/vicinity and hardly change the trimer's effect (Trimer-ethylenediamine, Trimer-GABA-OH, Trimer-GABA-OMe). The strong solvation of the tethered ionic group close to the aminopyrazole's hydrogen bonding unit may even hinder its approach to the Aβ peptide backbone. Consequently, all ThT values for inhibition as well as disaggregation lie above the trimer standard. (Both GABA derivatives, however, produce a significant viability increase of up to 30% in the lesion assay; it may be related to the biological response of GABA receptors.)

FIG. 7 shows TEM pictures. A: Aβ(1-42) fibrils. B-F: Aβ(1-42) mixtures (20 μM) with aminopyrazole trimer derivatives (100 μM). B: Trim-OMe; C: Trim-OH, D: Trim-Che; E: Trim-Lys-OMe; F: Trim-TEG-Lys-OMe; G: Trim-TEG-OEt; H: Trim-TEG-OH.

Figure 8:
FIG. 8 displays MD simulations (5 ns) of the complex between Aβ and an aminopyrazole trimer with attached nonpolar binding site; left Trim-Chg-Che; center Trim-Lys-Che; right Trim-TEG-Dodecyl.

By contrast, extended or cyclic unpolar groups align with nonpolar side chains and undergo hydrophobic as well as dispersive interactions (Trimer-CHG-CHE, Trimer Lys-CHE, Trimer-TEG-CHE, Trimer-TEG-DD). Likewise nonpolar peptide fragments derived from Aβ itself and attached to the trimer, may display their well-known self-complementarity and recognize their counterparts in the fibril (Trimer-LPFFD, Trimer-KLVFF). This is especially pronounced if the unpolar appendix is placed at a distance of more than one amino acid from the trimer-C-terminus, pushing the ThT rest fluorescence to values below 30%. According to a conformational search, unpolar binding sites on the ligand prefer the cluster of hydrophobic residues from Ile-31 to Ile-36. A TEG spacer in Trim-TEG-DD allows the attached dodecyl tail to explore the entire Met-35 ladder during MD simulations for extended van-der Waals interactions on the back of the pentameric Lührs fibril. CD spectra of Trim-Lys-Che, Trim-KLVFF and Trim-TEG-DD all feature/display an almost doubled β-sheet band intensity and the total loss of the aromatic signal at 280 nm. A straightforward interpretation suggests a remarkable stabilization of the cross-β-sheet with concomitant withdrawal of the aminopyrazole from its Phe-Phe cleft, resulting in a tight nonpolar lid covering the solvent-exposed unpolar aggregate face (FIG. 8). The related Trim-CHE, which forms thin filaments by itself, displays a remarkable fibril morphology in its complex with Aβ(1-42): very thick screwed fibrils (up to 70 nm) are produced, with a length of at least 600 nm. It thus seems, that fibrillogenesis is not prevented but rather shifted to a much more compact form, which does not accommodate well-ordered fluorescent ThT molecules. Remarkably, three of the eight best candidates in the cell lesion assays contain extended unpolar appendices, either as LPFFD or cyclohexylglycine peptide fragments.

FIG. 8 displays MD simulations (5 ns) of the complex between Aβ and an aminopyrazole trimer with attached nonpolar binding site; left Trim-Chg-Che; center Trim-Lys-Che; right Trim-TEG-Dodecyl.

Figure 9:
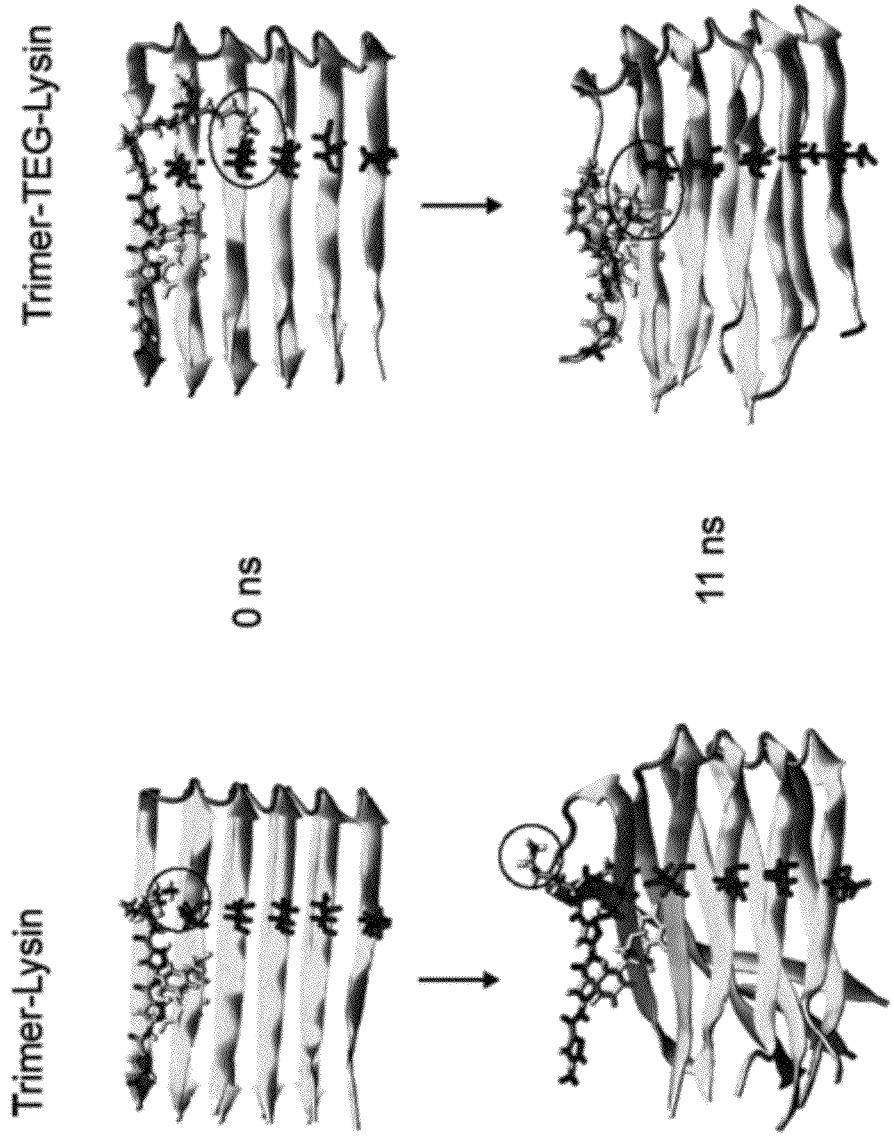
FIG. 9 displays MD simulations of the complexes between Aβ and Trimer-Lys vs. Trim-TEG-Lys.

A single C-terminal lysine on the trimer seems to be an exception. After aminopyrazole docking to the KLVFF site, lysine's ε-ammonium ion remains freely solvated during an entire 10 ns MD simulation run (FIG. 9 left). In this state it could easily form a saltbridge to Glu-22/Asp-23 of an opposing strand, which would according to Tycko support the connection two U strands via their polar interfaces to a fibril (Trimer-Lys-OMe). Contrary to almost all other trimer derivatives, this aminopyrazole accelerates Aβ aggregation (cf. kinetics). The corresponding CD spectrum is also exceptional, because it exhibits the typical additional Cotton effect at the wavelength of aromatic amino acids, but retains the β-sheet. Applicant concludes that docking of the aminopyrazole onto the Phe-Phe motif leads to formation of an intra- or intermolecular salt bridge, which brings two protofibrils in close proximity The exceptionally high aggregation propensity is also well documented in sedimentations, featuring the total loss of amyloid β-peptide during rotor acceleration. TEM pictures of mixtures with Aβ show very thin fibrils (5-10 nm) of 800 nm length, whereas this soluble aminopyrazole does not aggregate by itself.

In sharp contrast to Trim-Lys, a single lysine separated from the trimeric aminopyrazole core unit by the TEG spacer, leads to the most efficient suppression of Aβ fibril formation of all tested derivatives (20% ThT fluorescence). This structurally closely related pair of aminopyrazole trimers is a striking example for the fact, how strongly the exact placement of binding sites influences the degree and path of Aβ aggregation. Modeling studies reveal a preference for internal ion pair formation with Glu-22, confirmed by extended MD simulations (FIG. 9 right).

Ultracentrifugation and TEM experiments indicate a moderate tendency of the pure compounds to self-assemble into thin filaments, whereas the aggregation process of Aβ is redirected to unstructured material and thin bent filaments— completely different from Aβ fibrils (TEM pictures). In the cell culture experiments, Trim-TEG-Lys provides the most efficient rescue of PC-12 cells from Aβ toxicity (>40%).

FIG. 9 displays MD simulations of the complexes between Aβ and Trimer-Lys vs. Trim-TEG-Lys.

Figure 10B:
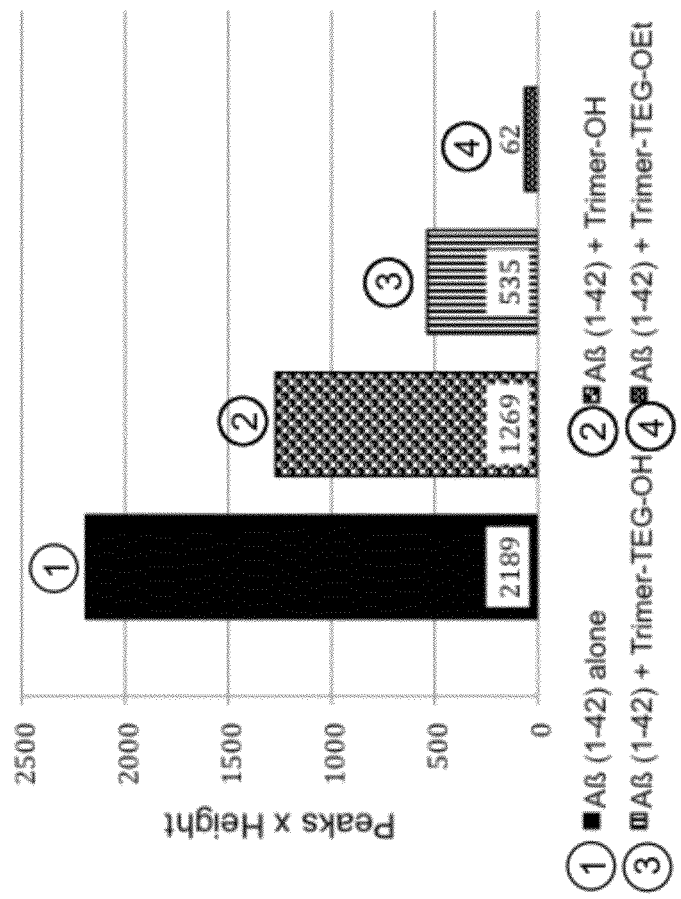
FIG. 10B shows FCS (Fluorescence Correlation Spectroscopy) measurements at 5 nm Aβ with Trimer-OH in comparison to Trim-TEG-OH/OEt (each at 10 μM).
Figure 10A:
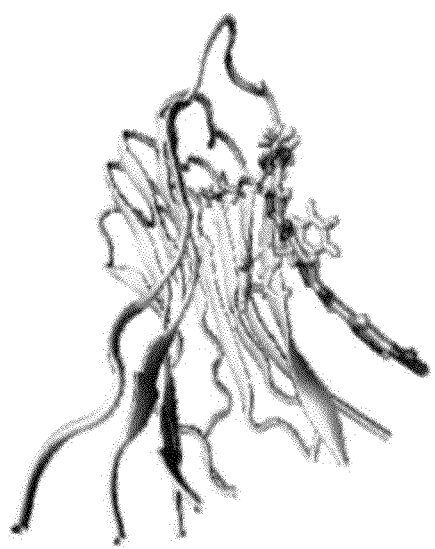
FIG. 10A shows a MD simulation of the complex between Aβ and Trimer-TEG-OEt.

The polar triethyleneglycol spacer smoothly intercalates between both peptide strands of the top U and similarly undergoes weak dispersive interactions with amino acids in the vicinity of the β-turn (Trimer-TEG-OEt, Trimer-TEG-OH). In extended MD simulations, the neutral methyl ester (replaced by the related methyl amide) could be observed to intrude into the water-filled canal formed by the stacked β-turns in the solid state structure (FIG. 10A). It serves as a linker to remote additional binding sites such as lipophilic or charged peptide fragments. For a better understanding of its influence on the pathologic Aβ self-assembly process, it was independently examined. Compared to the pure trimer prototype, the TEG-elongated aminopyrazole trimer (which is unremarkable/inconspicuous in ThT experiments), does not significantly change the medium aggregate size of aggregated Aβ, but instead produces a moderate amount of very small oligomers (monomers-pentamers), as evidenced by sedimentation analysis (FIGS. 6A-6F). For the Trimer standard as well as for both TEG-extensions sedimentation assays prove direct complex formation between the natural and the artificial peptide molecules. At nanomolar Aβ concentrations (as in the human brain) FCS even witnesses the uniform transition to very small oligomers within all Aβ aggregates (FIG. 10B). No filaments are formed from pure Trim-TEG-OH or —OMe solutions; in the presence of Aβ, very thin, delicate structures evolve, which show no helical twist. PC-12 cell protection is only very modest, comparable to the Trimer standard. Thus, the TEG spacer could serve a dual purpose: it brings recognition units close to the U-turn auf the fibril and simultaneously protrudes itself into the interior of the two parallel Aβ strands, facilitating further destabilization of the fibrillar structure.

FIG. 10A shows a MD simulation of the complex between Aβ and Trimer-TEG-OEt; FIG. 10B shows FCS (Fluorescence Correlation Spectroscopy) measurements at 5 nm Aβ with Trimer-OH in comparison to Trim-TEG-OH/OEt (each at 10 μM).

Remarkably, multiple lysines attached directly or by way of the TEG spacer to the aminopyrazole trimer, in principle allow the formation of multiple chelate complexes with the Glu-ladder beneath the fibril in molecular mechanics calculations (Trimer-KKKKKG, Trimer-TEG-KKKKKG). The modeling picture displays beautiful mutual chelate structures between the multiple glutamate carboxylates and bridging lysine ammonium functionalities. This complexation mode may lead to a significant destabilization of the U-turn structure and eventually dissolve the β-sheet. Together with Trimer-TEG-Lys the above-mentioned are indeed the most potent of all synthesized aminopyrazole derivatives and deplete the ThT fluorescence level down to 20% in inhibition and disaggregation experiments (FIG. 4). The corresponding CD spectrum features the additional CD band at ~280 nm, typical for aromatic amino acids; however, in this case, the β-sheet band almost completely disappears with time, indicating dissolution of the secondary peptide structure (FIG. 11A to 11C).

TABLE 2

Figure 11A:
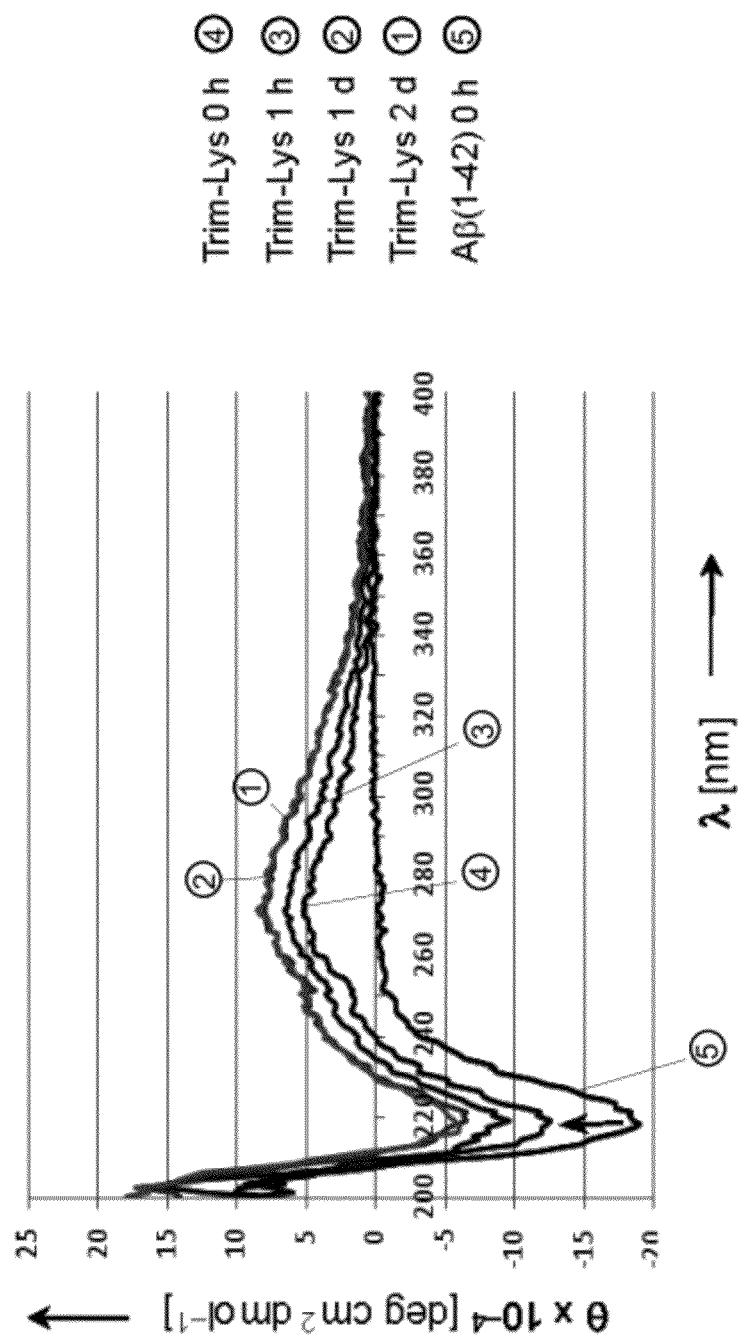
FIG. 11A to 11C show typical CD spectra recorded for aggregated Aβ(1-42) alone (curve 5 in FIGS. 11A-11C) and after addition of aminopyrazole ligand (Type A: Trimer-Lys.
Figure 11B:
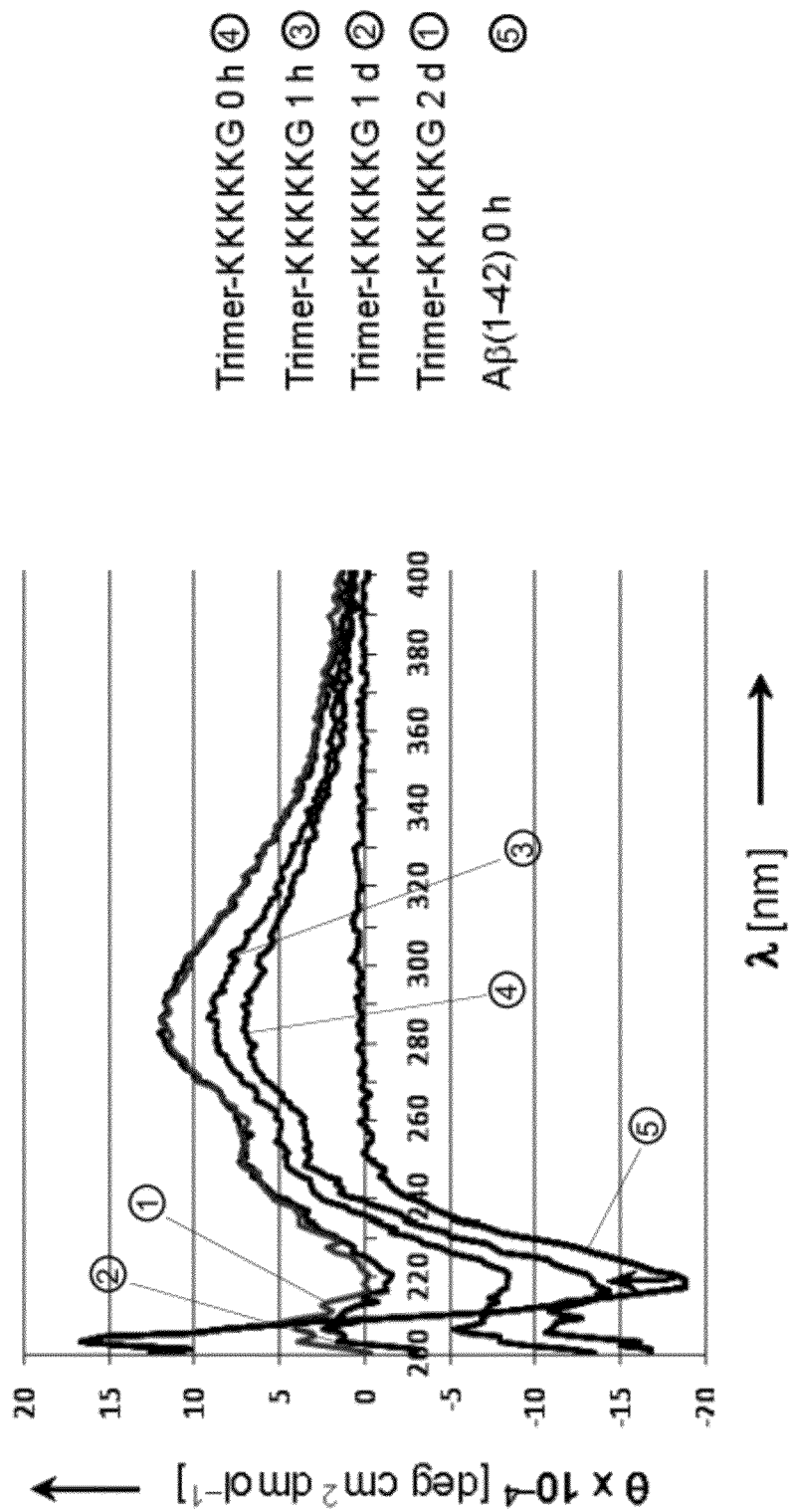
Figure 11C:
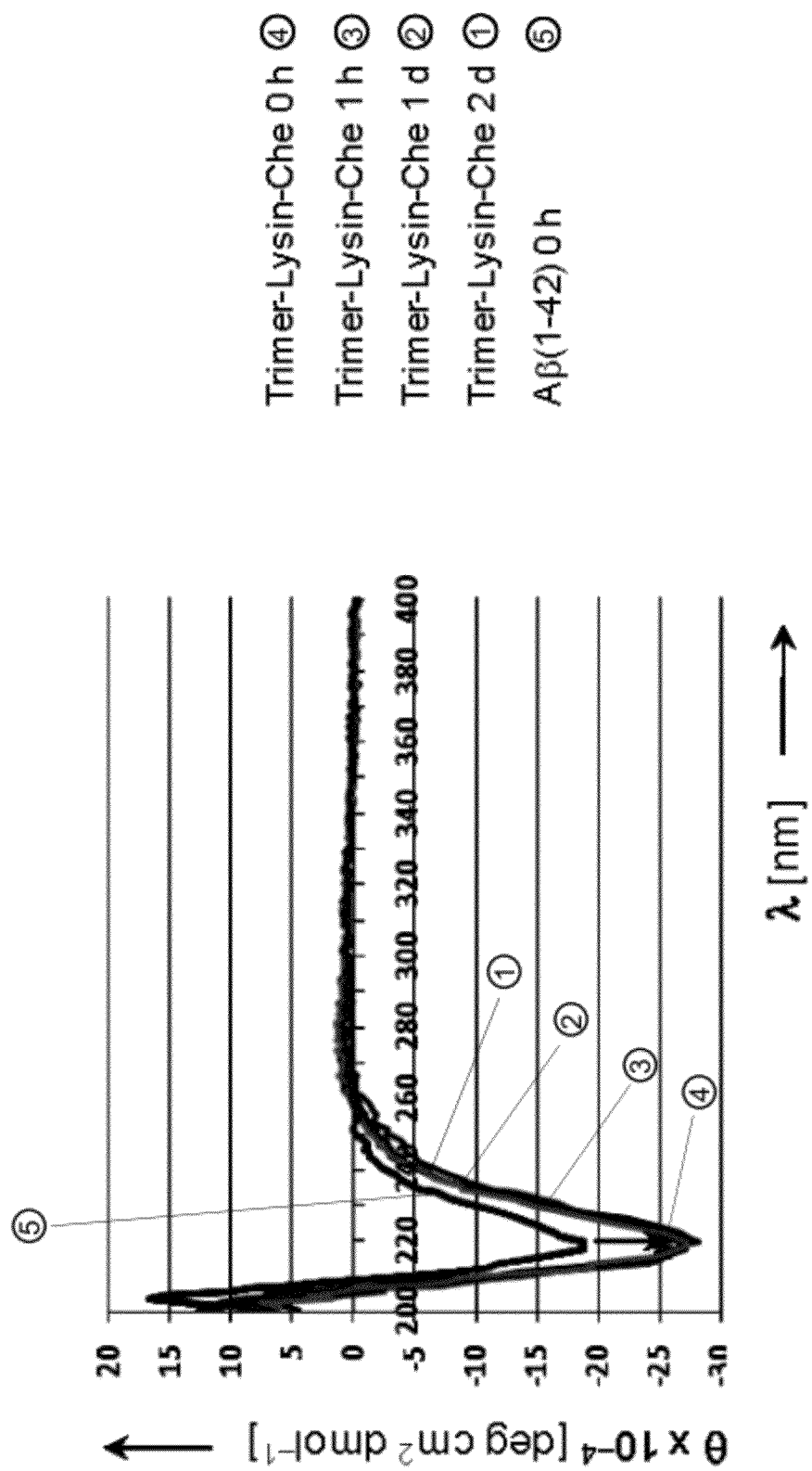

Classification of CD spectra to three main types (see also FIG. 11A to 11C).

| Type A | Type B | Type C |
|---|---|---|
| Trim-Lys-OMe | Trim-KKKKKG | Trim-Lys-Che |
| Trim-TEG-Lys-OMe | Trim-TEG-KKKKKG | Trim-TEG-KLVFF |
| Trim-TEG-OH | Trim-Lys-TEGDA-Lys-Trim | Trim-TEG-DD |

FIG. 11A to 11C show typical CD spectra recorded for aggregated Aβ(1-42) alone (curve 5 in FIGS. 11A-11C) and after addition of aminopyrazole ligand (Type A: Trimer-Lys: FIG. 11A; Type B: Trimer-KKKKKG: FIG. 11B; Type C: Trimer-Lys-Che: FIG. 11C). Time progresses in the direction of the embedded arrows, indicated by lighter colors (0 h, 1 h, 1 d, 2 d). Test solutions contained 10 μM Aβ(1-42), 5 μM potassium phosphate buffer (pH=7.3), 2% HFIP and 10 μM of the respective aminopyrazole trimer derivative.

Figure 12:
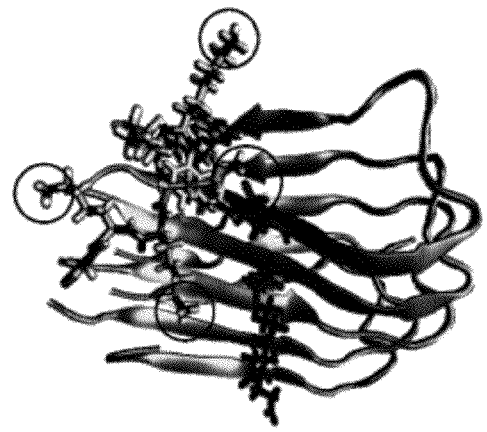
FIG. 12 displays a MD simulation of the complex between Aβ and Trimer-KKKKG.

Subsequent MD simulations, however, resulted in successive detachment of the pentalysine tail from the glutamate ladder, until finally all alkylammonium groups pointed into the free solvent and towards the opposite side of the peptide strand. Such an arrangement may also result in far-reaching conformational effects, indicated already be widening of the upper U-turn; these are now proposed to destroy the existing β-sheet (FIG. 12). The high positive charge of all five lysine residues requires the use of PBS with its high ionic strength for sedimentation experiments. Here the positively charged aminopyrazoles alone displayed a considerable self-association, reaching s-values of up to 40 in the absence of a TEG spacer. Admittedly, their structures are somewhat reminiscent of the amphiphilic hybrid peptides (e.g., KLVFF-EEEEE) presented in the nineties for aggregation prevention by surface tension increase. In fact, a similar mechanism could also be functioning in the case of applicant's amphiphilic aminopyrazole-pentalysines.

FIG. 12 displays a MD simulation of the complex between Aβ and Trimer-KKKKG.

Inhibition of Aβ-Induced Toxicity.

Initially, all compounds were screened for any toxic effect they might have by adding each compound at 100 μM and measuring the effect on cell viability using the 3-(4,5-dimethylthiazol-2-yl)-2,5-diphenyltetrazolium bromide (MTT) reduction assay (Datki, Z.; Juhasz, A.; Galli, M.; Soos, K.; Papp, R.; Zadori, D.; Penke, B. *Brain Res. Bull.* 2003, 62, 223-229) in differentiated rat pheochromocytoma (PC-12) cells (Shearman, M. S. *Methods Enzymol.* 1999, 309, 716-723). Encouragingly, none of the compounds was toxic to the cells at this concentration. Next, to examine whether the aminopyrazole trimers could protect cell from Aβ42-induced neurotoxicity, cells were treated for 24 h with 10 μM Aβ(1-42), a concentration that produces 30 to 40% decrease in cell viability, in the absence or presence of 100 μM of each compound. The viability of the cells then was assessed using the MTT assay. In both series (with and without TEG spacers) several candidates were found to rescue cell viability significantly.

Intriguingly, the most efficient inhibition of Aβ toxicity was achieved with 3 lipophilic extensions and Trimer-TEG-Lys-OMe, which were also superior in ThT and related assays. The two GABA derivatives are a surprise—they might potentially interact with GABA receptors and not with the Aβ peptide itself. The above-delineated findings demonstrate that trimeric aminopyrazoles are indeed active against Aβ-induced toxicity in living cells; they also provide experimental evidence for their low toxicity at relatively high doses of 0.1 mM, in spite of, e.g., the presence of an N-terminal nitro group.

Figure 13B:
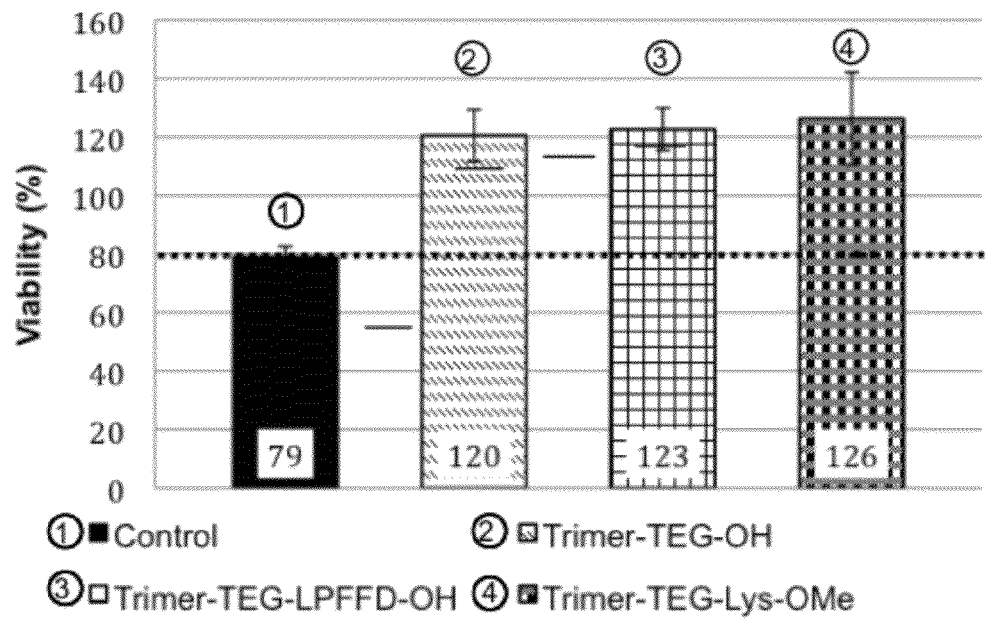
FIGS. 13A and 13B display viability assays of PC-12 cells with trimeric aminopyrazoles (100 μM).
Figure 13A:
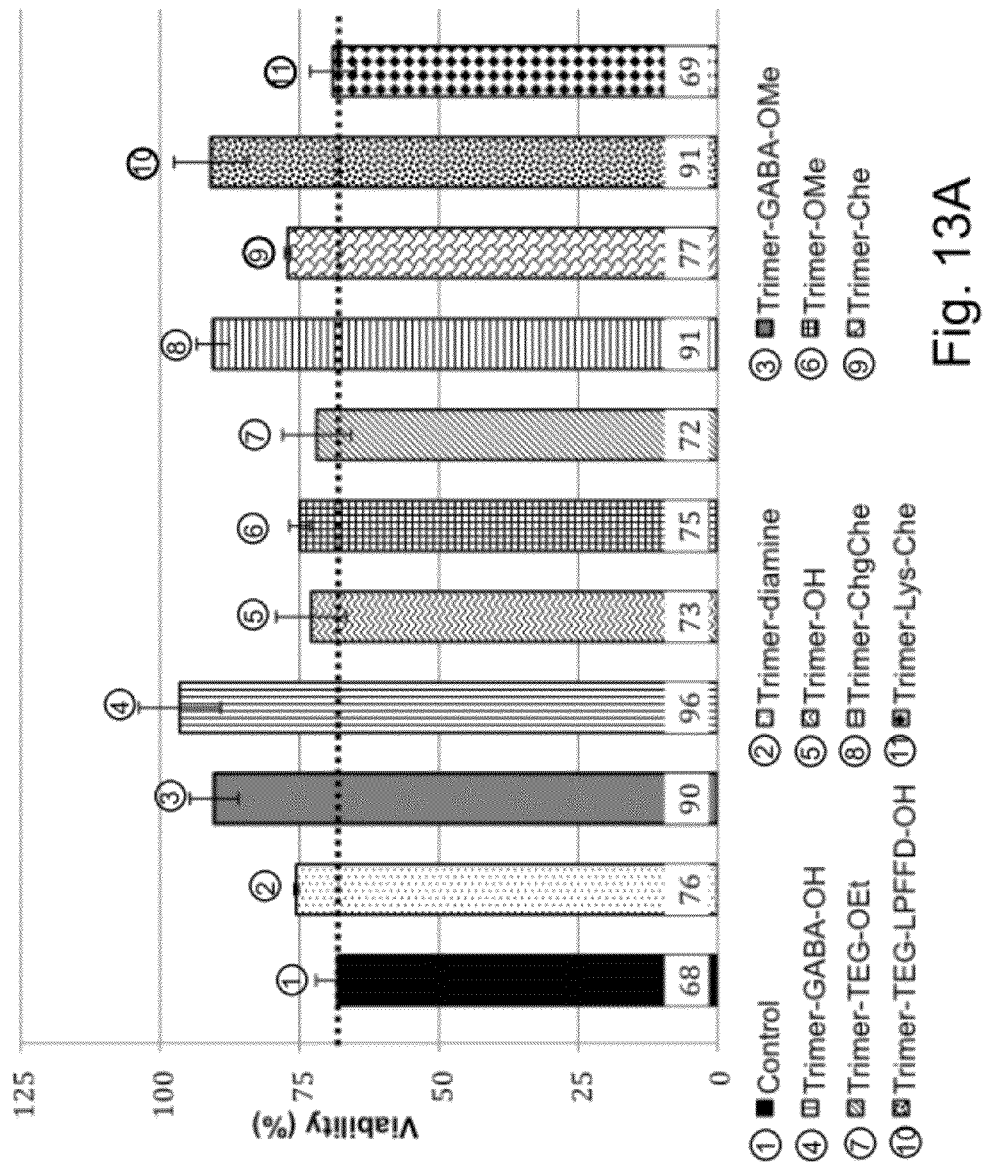

FIGS. 13A and 13B display viability assays of PC-12 cells with trimeric aminopyrazoles (100 μM). FIG. 13A shows Aβ lesion control at ~70%, FIG. 13B at ~80% viability.

Based on this initial screen, applicant evaluated the $IC_{50}$ value of compounds that increased the viability of PC-12 cells to ≧90%. The data are summarized in Table 3. To determine the $IC_{50}$ value of each of the compounds, dose-dependence MTT experiments were conducted with the aminopyrazole trimers, at a fixed Aβ42 concentration of 10 mM and increasing concentrations of β-sheet ligand (0.3, 1, 3, 10, 30 and 100 μM). $IC_{50}$ in this respect is defined as the concentration of the β-sheet ligand (aminopyrazole trimer derivative), at which the inhibition of Aβ toxicity just reaches 50% (FIG. 14).

Figure 14:
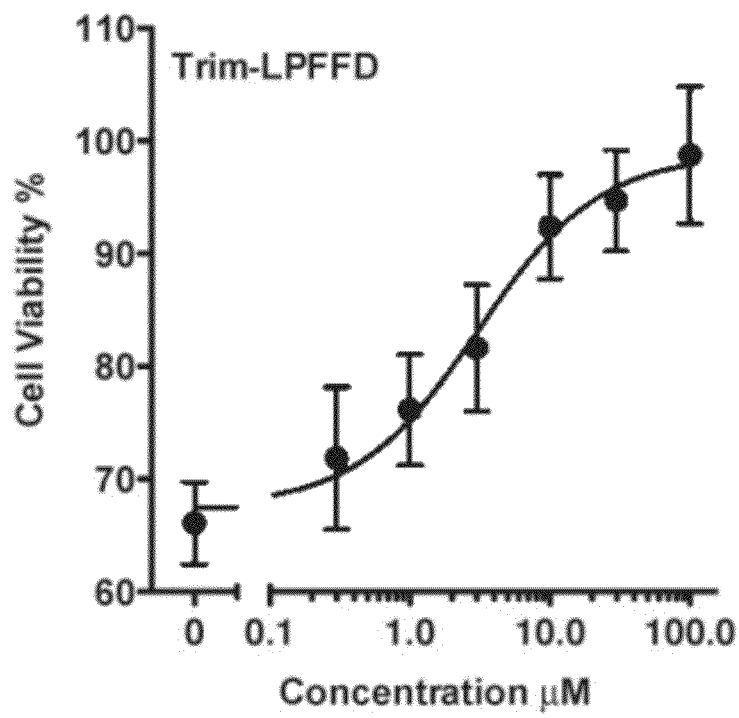
FIG. 14 shows a dose-response curve for the inhibition of Aβ-induced toxicity in PC-12 cells by Trimer-LPFFD (IC$_{50}$=3.1 mM).

FIG. 14 shows a dose-response curve for the inhibition of Aβ-induced toxicity in PC-12 cells by Trimer-LPFFD ($IC_{50}$=3.1 mM).

Table 3 shows the $IC_{50}$ values of the most potent inhibitors of Aβ-induced toxicity.

TABLE 3

$IC_{50}$ values of the most potent inhibitors of Aβ-induced toxicity.

| Inhibitor | $IC_{50}$ [μM] |
| --- | --- |
| Trim-LPFFD-OH | 3.1 |
| Trim-TEG-LPFFD-OH | 10.1 |
| Trim-GABA-OH | 18.5 |
| Trim-GABA-OMe | 20.3 |
| Trim-Lys-TEGDA-Lys-TEGDA | 21.5 |
| Trim-TEG-OH | 35.3 |
| Trim-TEG-Lys-OMe | 52.7 |
| Trim-Chg-Che | 81.0 |
| Trim-TEG-KLVFF | >100 |
| Trim-TEG-DD | >100 |

With respect to $IC_{50}$ values, the two non-polar LPFFD-derivatives were found to be the most effective. Since the Aβ42 concentration was always kept constant at 10 μM, it should be emphasized, that substoichiometric $IC_{50}$ values such as that of Trim-LPFFD-OH indicate very high affinity towards the target peptide, even if a 1:1 complex is assumed. It should be kept in mind that, in the brain, Aβ concentrations are in the low nanomolar range, similar to the situation in enzyme assays. Only in such a scenario, $IC_{50}$ values can be expected to drop to nanomolar concentrations.

Conclusions and Outlook.

Applicant's investigation provided experimental evidence for the fact that small structural changes in β-sheet ligands have a profound influence on the aggregation behavior of misfolding proteins. Moreover, a common anchor point has been identified for the inventive aminopyrazole trimer derivatives, allowing to perform docking experiments and subsequent MD simulations. Intriguingly, various different types of suitably arranged binding sites correlate well with various kinds of modulated Aβaggregation behavior. CD measurements, on the one hand, as well as ThT aggregation assays, on the other hand, display pronounced continuous changes within more than two hours, which may involve conformational changes which are not yet visible even during extended modeling experiments. A structure activity relation can therefore be suggested, evolving from a synopsis of different biophysical and biochemical and "in silico"-experiments. Two major binding motifs could thus be discovered, which greatly improve the β-sheet breaker ability of the aminopyrazole trimer: remote lipophilic moieties for dispersive interactions with the unpolar cluster of amino acids between Ile-31 to Ile-36, and distant cationic peptide fragments which destabilize Aβ's U-turn. Only the latter, however, effectively destroys the cross-β-sheet. Applicant has confirmed these structure motifs postulated from modeling and aggregation experiments. Direct evidence has been gained from cocrystals of these complexes as well as from 2D solid state NMR experiments.

Contents:
1. General Synthetic Procedures
2. Detailed experimental procedures
3. Manual Solid Phase Peptide
4. Thioflavine T-Assays
5. Kinetics of Aβ aggregation and disaggregation
6. Equilibrium of Aβ aggregation and disaggregation
7. CD spectroscopic measurements
8. Fluorescence Correlation Spectroscopy (FCS)
9. Sedimentation analysis (SA)
10. Transmission Electron Microscopy (TEM)
11. Cell Culture/MTT Viability Assays 1. General Synthetic Procedures General Procedure A (C-Terminal Basic Ester Hydrolysis)

The N-(p-methoxybenzyl)-pyrazolecarboxylic acid methyl ester derivative was dissolved in a mixture of MeOH (50 ml) and THF (50 ml). Then, aq. lithium hydroxide (2.50 equiv. in 10 ml) was added to the solution and the mixture was stirred at room temperature until the starting material disappeared on the TLC plate. The solvent was removed under reduced pressure. The residue was dissolved in water and acidified with aq 1 M HCl. The precipitate was filtered, washed with aq 1 M HCl and dried in vacuo.

General Procedure B (Trimer-OH Coupling to C-Terminal Amine Extension with Mukaiyama's Reagent)

In an argon atmosphere, the N-terminal and PMB-protected pyrazole carboxylic acid compound (1.10 equiv) was suspended in DCM. To this suspension diisopropylethylamine (3.50 equiv) and 2-chloro-1-methylpyridinium iodide (Mukaiyama's reagent, 1.50 equiv) were added. Then the C-terminally and/or side chain-protected amino acid (1.00 equiv) or another coupling partner (1.00 equiv) was added to the reaction mixture. If the C-terminal protected compound was applied as an ammonium salt, another equivalent of diisopropylethylamine (1.00 equiv) was added before for neutralization. The resulting mixture was stirred overnight at room temperature. Subsequently, the organic layer was washed twice with aq 1 M HCl, sat. aq NaHCO₃ and sat. aq NaCl. After drying over MgSO₄, the solvent was evaporated in vacuo. The crude product was purified by chromatography on silica gel (the eluent is described for each compound in the following detailed procedures).

General Procedure C (Trimer-OH Coupling to C-Terminal Amine Extension with HCTU)

Under an inert atmosphere, the N-terminal and PMB-protected pyrazole carboxylic acid compound (1.10 equiv) was dissolved in DCM/DMF (3:1). Cl—HOBt (2.50 equiv), HCTU (1.10 equiv) and 2,6-lutidine (3.00 equiv) were added and stirred for 10 min at 0° C. The C-terminally and/or side chain-protected amino acid (1.00 equiv) or another coupling partner (1.00 equiv) was dissolved in DCM/DMF (3:1) and added to the reaction mixture. If the C-terminal protected compound was applied as an ammonium salt, 2,6-lutidine (1.00 equiv) was added to this solution before for neutralization. The reaction mixture was stirred overnight at room temperature. The mixture was extracted twice with aq 1 M HCl, sat. aq NaHCO$_3$ and sat. aq NaCl and dried over MgSO$_4$. After filtration, the solvent was evaporated until it was dry and the residue was purified by chromatography on a silica column.

General Procedure D (Trimer-OH Coupling to C-Terminal Amine Extension with EDC)

In an argon atmosphere, the N-terminal and PMB-protected pyrazole carboxylic acid compound (1.00 equiv) was suspended in DCM and cooled to 0° C. To this suspension HOBt (3.00 equiv) and after ten minutes EDC-HCl (3.00 equiv) were added. The reaction mixture was stirred for another ten minutes and then, the C-terminally protected amine coupling partner was added to the suspension. The mixture was gradually warmed to room temperature and stirred for two more days. Then, the organic layer was washed twice with 1M aq. HCl, sat. aq NaHCO$_3$ and sat. aq NaCl and dried over MgSO$_4$. The solvent was evaporated in vacuo and the crude product was purified by chromatography on silica.

General Procedure E (PMB-Deprotection)

In an argon atmosphere the PMB-protected pyrazole compound was heated in anhydrous TFA (2.50 mL/50 μmol) to 70° C. for 5 h. Subsequently, the solution was cooled to 0° C. and treated with ice-cold diethyl ether. The precipitating solid was centrifuged off and washed five times with diethyl ether. Afterwards, the residue was dissolved in DCM and the solvent was removed quickly in vacuo. This procedure was repeated five times and the product was dried in vacuo.

2. Detailed Experimental Procedures 3-(3-(3-Amino-1-(4-methoxybenzyl)-1H-pyrazole-5-carboxamido)-1-(4-methoxybenzyl)-1H-pyrazole-5-carboxamido)-1-(4-methoxybenzyl)-1H-pyrazole-5-carboxylic acid methyl ester To a solution of the respective nitro precursor (273 mg, 364 μmol) in THF (15 mL) was added methanol (5 mL) and Pd/C (10 mol %). The flask was evacuated and filled with H$_2$ (general procedure A). The reaction mixture was stirred for 16 h and the catalyst was removed by filtration over celite. The solution was concentrated in vacuo and the product was crystallized over night at 8° C. Yield: 215 mg (299 μmol, 82%); colorless solid.

$^1$H NMR (500 MHz, DMSO-d$_6$): δ [ppm]=3.70-3.72 (3s, 9H, CH$_3$-PMB), 3.85 (s, 3H, OOCH$_3$), 4.85 (s, 2H, NH$_2$), 5.44 (s, 2H, CH$_2$-PMB), 5.58 (s, 2H, CH$_2$-PMB), 5.63 (s, 2H, CH$_2$-PMB), 6.36 (s, 1H, CH-pyrazole), 6.83-6.90 (m, 6H, CH-arom.), 7.11-7.22 (m, 7H, CH-arom., CH-pyrazole), 7.65 (s, 1H, CH-pyrazole), 10.90 (s, 1H, NH-amide), 11.40 (s, 1H, NH-amide). $^{13}$C NMR (125 MHz, DMSO-d$_6$): δ [ppm]=52.1, 52.2, 53.0, 53.2, 54.9, 55.0, 94.8, 101.0, 102.9, 113.5, 113.7, 113.8, 128.5, 128.7, 129.0, 129.6, 130.6, 131.1, 133.8, 134.0, 145.4, 154.1, 157.4, 158.3, 158.6, 158.7, 159.3. Mp.: 182.3-183.1° C. R$_f$: 0.07 n-pentane/ethyl acetate (1:1). HRMS (ESI): calcd for C$_{37}$H$_{37}$N$_9$O$_7$H: 720.2889. found: 720.2901; calcd for C$_{37}$H$_{37}$N$_9$O$_7$Na: 742.2708. found: 742.2727.

3-(3-(3-Amino-1H-pyrazole-5-carboxamido)-1H-pyrazole-5-carboxamido)-1H-pyrazole-5-carboxylic acid methyl ester trifluoroacetate (Aminotrimer-OMe)

A portion of 61 mg (85 μmol, 1.00 equiv) of PMB-protected aminopyrazole trimer synthesized above was treated with hot TFA according to general procedure E to yield the Aminotrimer-OMe as a colorless solid. Yield: 24 mg (51 μmol, 60%).

$^1$H NMR (500 MHz, DMSO-d$_6$): δ [ppm]=3.85 (s, 3H, OOCH$_3$), 7.11 (s, 1H, CH-pyrazole), 7.55 (brs, 2H), 11.20 (brs, 1H), 11.25 (brs, 1H), 12.18 (brs, 1H), 13.45 (brs, 1H, NH-pyrazole), 13.67 (brs, 1H, NH-pyrazole), 13.76 (brs, 1H, NH-pyrazole). $^{13}$C NMR (125 MHz, DMSO-d$_6$): δ [ppm]= 51.9, 98.4, 100.2, 114.5, 116.8, 132.8, 136.6, 145.0, 147.2, 153.9, 154.2, 156.2, 159.2. Mp: decomposition at 272° C. HRMS (ESI): calcd for C$_{13}$H$_{13}$N$_9$O$_4$H: 360.1163. found: 360.1160; calcd for C$_{13}$H$_{13}$N$_9$O$_4$Na: 382.0983. found: 382.0988.

1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxylic acid A 1.00 g (1.33 mmol, 1.00 equiv) amount of 1-(4-methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxylic acid methyl ester [O$_2$N-Pz(PMB)-Pz(PMB)-Pz(PMB)-OMe] and 81 mg of lithium hydroxide (3.38 mmol, 2.54 equiv) were stirred in a mixture of methanol/THF/water (5:5:1) for 18 h. The crude product is prepared according to general procedure A to yield the compound as a colorless solid. Yield: 0.92 g (1.25 mmol, 94%).

$^1$H NMR (500 MHz, DMSO-d$_6$): δ [ppm]=3.70-3.71 (3s, 9H, CH$_3$-PMB), 5.60 (s, 2H, CH$_2$-PMB), 5.66 (s, 2H, CH$_2$-PMB), 5.81 (s, 2H, CH$_2$-PMB), 6.86-6.91 (m, 6H, CH-arom.), 7.14-7.20 (m, 5H, CH-arom., CH-pyrazole), 7.25-7.30 (m, 2H, CH-arom.), 7.71 (s, 1H, CH-pyrazole), 7.99 (s, 1H, CH-pyrazole), 11.39 (brs, 1H, NH-amide), 11.53 (brs, 1H, NH-amide). $^{13}$C-NMR (125 MHz, DMSO-d$_6$): δ [ppm]=55.0, 98.9, 103.0, 105.0, 113.8, 114.0, 127.9, 128.7, 128.8, 129.3, 129.5, 134.2, 136.7, 143.6, 144.8, 145.4, 153.5, 155.4, 157.0, 158.7, 159.0, 160.3. Mp: 258.1-260.2° C. HRMS (ESI): calcd for C$_{36}$H$_{32}$N$_9$O$_9$: 734.2328; found: 734.2323.

3-(3-(3-Nitro-1H-pyrazole-5-carboxamido)-1H-pyrazole-5-carboxamido)-1H-pyrazole-5-carboxylic acid (Trimer-OH)

51 mg of compound PMB-protected Trimer precursor (69 μmol, 1.00 equiv) was dissolved in 3 mL trifluoroacetic acid according to general procedure D to yield Trimer-OH as a colorless solid. Yield: 23 mg (64 μmol, 93%).

$^1$H NMR (500 MHz, DMSO-d$_6$): δ [ppm]=7.02 (brs, 1H, CH-pyrazole), 7.56 (s, 1H, CH-pyrazole), 7.94 (s, 1H, CH-pyrazole), 11.17 (brs, 1H, NH-amide), 11.42 (s, 1H, NH-amide), 13.51 (brs, 2H, NH-pyrazole), 14.97 (s, 1H, NHpyrazole). $^{13}$C NMR (125 MHz, DMSO-d$_6$): δ [ppm]=98.1, 98.3, 99.9, 102.2, 138.6, 155.0, 155.8, 156.6, 160.4. Mp: decomposition at 313.4° C. HRMS (ESI): calcd for C$_{12}$H$_8$N$_9$O$_6$: 374.0592; found: 374.0611.

2-(1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamido-6-(tert-butoxycarbonyl)-lysine methyl ester A portion of 200 mg (0.27 mmol, 1.10 eq) of PMB-protected Trimer-OH and 73 mg (0.24 μmol, 1.00 equiv) of N-Amino-N$^ε$-(tert-butyloxycarbonyl)-(S)-lysine-carboxylic acid methyl ester hydrochloride were reacted with 95 mg (0.37 mmol, 1.50 equiv) of Mukaiyama's reagent and 0.19 mL (1.11 mmol, 4.50 equiv) of diisopropylethylamine according to general procedure B. The residue was purified by column chromatography on silica gel using n-pentane/ethyl acetate (2:1) to yield the coupling product as a colorless solid. Yield: 153 mg (0.16 μmol, 63%).
$^1$H NMR (500 MHz, CDCl$_3$): δ [ppm]=1.37-1.54 (m, 13H, CH$_2$-Lys, (CH$_3$)$_3$), 1.71-1.83 (m, 1H, CH$_2$-Lys), 1.88-1.99 (m, 1H, CH$_2$-Lys), 3.05-3.14 (m, 2H, CH$_2$-Lys), 3.75-3.76 (2s, 9H, CH$_3$-PMB), 3.80 (s, 3H, OOCH$_3$), 4.55 (brs, 1H, NH-amide), 4.67-4.75 (m, 1H, α-CH-Lys), 5.54 (d, 2H, $^3$J=4.3 Hz, CH$_2$-PMB), 5.61 (d, 1H, $^3$J=7.5 Hz, CH$_2$-PMB), 5.75 (d, 1H, $^3$J=7.5 Hz, CH$_2$-PMB), 5.81 (s, 2H, CH$_2$-PMB), 6.80-6.85 (m, 7H, CH-arom., NH-amide), 7.10 (s, 1H, CH-arom., CH-pyrazole), 7.20-7.26 (m, 5H, CH-pyrazole), 7.33 (brs, 1H, CH-pyrazole), 7.37-7.41 (m, 2H, CH-arom.), 8.40 (brs, 1H, NH-amide), 8.75 (brs, 1H, NH-amide). $^{13}$C NMR (125 MHz, CDCl$_3$): δ [ppm]=13.7, 14.2, 19.1, 21.0, 22.7, 28.4, 29.6, 30.6, 32.0, 40.1, 52.2, 52.8, 53.8, 54.1, 55.2, 56.0, 64.4, 98.2, 98.8, 103.6, 113.9, 114.1, 127.1, 130.1, 134.6, 135.0, 136.0, 144.7, 154.1, 156.1, 159.2, 159.3, 159.4, 159.8, 172.8. Mp: 94.4° C. R$_f$: 0.10 n-pentane/ethyl acetate (2:1). HRMS (ESI): calcd for C$_{48}$H$_{55}$N$_{11}$O$_{12}$H: 978.4104. found: 978.4144; calcd for C$_{48}$H$_{55}$N$_{11}$O$_{12}$Na: 1000.3924. found: 1000.3942.

6-Amino-2-(-3-(3-(3-nitro-1H-pyrazole-5-carboxamido)-1H-pyrazole-5-carboxamido)-1H-pyrazole-5-carboxamido-lysinyl-carboxylic acid methyl ester trifluoroacetate (Trimer-Lys-OMe)

A portion of 50 mg (51 μmol, 1.00 equiv) of the PMB-protected Trimer-Lys-OMe was treated with hot TFA according to general procedure E to yield the free Trimer-Lys-OMe as a colorless solid. Yield: 37 mg (49 μmol, 96%).
$^1$H NMR (500 MHz, DMSO-d$_6$): δ [ppm]=1.38-1.42 (m, 2H, CH$_2$-Lys), 1.53-1.59 (m, 2H, CH$_2$-Lys), 1.81-1.84 (m, 2H, CH$_2$-Lys), 2.78-2.82 (m, 2H, CH$_2$-Lys), 3.67 (s, 3H, OOCH$_3$), 4.42-4.45 (m, 1H, α-CH-Lys), 7.41 (s, 1H, CH-pyrazole), 7.61 (s, 1H, CH-pyrazole), 7.65 (bs, 3H, H-8), 7.95 (s, 1H, CH-pyrazole), 8.89 (d, $^3$J=6.9 Hz, 1H, NH-amide), 11.16 (s, 1H, NH-amide), 11.42 (s, 1H, NH-amide), 13.28 (s, 1H, NH-pyrazole), 13.45 (s, 1H, NH-pyrazole), 14.97 (s, 1H, NH-pyrazole). $^{13}$C NMR (125 MHz, DMSO-d$_6$): β [ppm]= 22.3, 26.3, 29.6, 51.8, 97.5, 98.1, 102.0, 102.5, 154.8, 172.2. Mp: decomposition at 198° C. HRMS (ESI): calcd for C$_{19}$H$_{23}$N$_{11}$O$_2$H: 518.1855. found: 518.1860.

2-(1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamido-6-(tert-butoxycarbonyl)-lysine A 143 mg (146 μmol, 1.00 equiv) amount of 2-(1-(4-methoxybenzyl)-3-(1-(4-methoxybenzyl)-3-(1-(4-methoxyben-zyl)-3-nitro-1H-pyrazole-5-carboxamido)-1H-pyrazole-5-carboxamido)-1H-pyrazole-5-carboxamido-6-(tert-butoxycarbonyl)-lysine methyl ester and 9 mg lithium hydroxide (376 μmol, 2.57 equiv) were stirred in a mixture of methanol/THF/water (5:5:1) for 16 h at 65° C. Workup and purification were conducted according to general procedure A to yield the free carboxylic acid as a colorless solid. Yield: 111 mg (115 μmol, 79%).
$^1$H NMR (500 MHz, DMSO-d$_6$): δ [ppm]=1.21-1.41 (m, 13H, CH$_2$-Lys, (CH$_3$)$_3$), 1.67-1.86 (m, 2H, CH$_2$-Lys), 2.87-2.91 (m, 2H, CH$_2$-Lys), 3.70-3.71 (3s, 9H, CH$_3$-PMB), 4.25 (brs, 1H, α-CH-Lys), 5.59 (s, 2H, CH$_2$-PMB), 5.68 (s, 2H, CH$_2$-PMB), 5.81 (s, 2H, CH$_2$-PMB), 6.77 (t, $^3$J=5.3 Hz, 1H, NH), 6.85-6.92 (m, 6H, CH-arom.), 7.17-7.21 (m, 4H, CH-arom.), 7.26-7.29 (m, 2H, CH-arom.), 7.38 (s, 1H, CH-pyrazole), 7.71 (s, 1H, CH-pyrazole), 7.98 (s, 1H, CH-pyrazole), 8.78 (d, $^3$J=6.0 Hz, 1H, NH-amide), 11.34 (s, 1H, NH-amide), 11.50 (brs, 1H, NH-amide). $^{13}$C NMR (125 MHz, DMSO-d$_6$): δ [ppm]=28.1, 52.6, 54.9, 55.0, 77.2, 100.9, 105.0, 105.1, 105.3, 113.7, 113.8, 113.9, 127.9, 128.7, 129.0, 129.3, 129.5, 129.6, 134.3, 136.7, 144.8, 145.2, 153.5, 158.6, 159.0. Mp: 177.6-180.0° C. HRMS (ESI): calcd for C$_{47}$H$_{53}$N$_{11}$O$_{12}$Na: 986.3767. found: 986.3760; calcd for C$_{47}$H$_{52}$N$_{11}$O$_{12}$: 962.3802; found: 962.3839.

tert-Butyl-6-(1-cyclohexylethylamino)-5-(1-(4-methoxybenzyl)-3-(1-(4-methoxy-benzyl)-3-(1-(4-methoxybenzyl)-3-nitro-1H-pyrazole-5-carboxamido)-1H-pyrazole-5-carboxamido)-1H-pyrazole-5-carboxamido-6-oxo-hexylcarbamate A 85 mg (0.88 mmol, 1.10 equiv) amount of PMB-protected Trimer-Lys-OH and 11.76 μL (0.80 mmol, 1.00 equiv) of cyclohexylethylamine were reacted with 34 mg (0.20 mmol, 2.51 equiv) of Cl—HOBt, 36.41 mg (0.88 mmol, 1.10 equiv) of HCTU and 28 μL (1.20 mmol, 3.00 equiv) 2,6-lutidine according to general procedure C. The crude product was purified by column chromatography on silica gel using dichloromethane/ethyl acetate (3:1) to yield compound x as a colorless solid. Yield: 76 mg (71 μmol, 88%).
$^1$H NMR (500 MHz, DMSO-d$_6$): δ [ppm]=0.87-0.92 (m, 2H, CH$_2$-cyclohexyl), 1.00-1.02 (d, 3H, $^3$J=6.8 Hz, CH$_3$), 1.05-1.17 (m, 3H, CH-cyclohexyl, CH$_2$-cyclohexyl), 1.24-1.39 (m, 14H, CH$_2$-Lys, (CH$_3$)$_3$), 1.52-1.69 (m, 7H, CH$_2$-cyclohexyl, CH$_2$-Lys), 2.87-2.91 (m, 2H, CH$_2$-Lys), 3.59-3.64 (m, 1H, CH), 4.33-4.39 (m, 1H, α-CH-Lys), 5.53-5.63 (m, 2H, CH$_2$-PMB), 5.68 (s, 2H, CH$_2$-PMB), 5.81 (s, 2H, CH$_2$-PMB), 6.75 (t, 1H, $^3$J=5.5 Hz, NH), 6.83-6.92 (m, 6H, CH-arom.), 7.17-7.20 (m, 4H, CH-arom.), 7.26-7.29 (m, 2H, CH-arom.), 7.44 (s, 1H, CH-pyrazole), 7.68 (d, 1H, $^3$J=8.7 Hz, NH), 7.71 (s, 1H, CH-pyrazole), 7.98 (s, 1H, CH-pyrazole), 8.58 (d, 1H, $^3$J=8.1 Hz, NH-amide), 11.33 (s, 1H, NH-amide), 11.50 (s, 1H, NH-amide). $^{13}$C NMR (125 MHz, DMSO-d$_6$): δ [ppm]=13.5, 17.6, 18.5, 23.0, 25.6, 25.9, 28.2, 28.6, 28.7, 29.1, 30.1, 33.6, 42.3, 48.5, 55.0, 63.4, 77.2, 99.9, 100.8, 105.0, 113.6, 113.8, 114.0, 127.9, 128.7, 129.0, 129.3, 129.5, 129.7, 134.3, 134.7, 136.7, 144.8, 145.1, 153.5, 155.4, 155.5, 156.8, 158.6, 159.0, 170.5. Mp: 154.2-155.7° C. R$_f$: 0.45 dichlormethane/ethyl acetate (3:1). HRMS (ESI): calcd for C$_{55}$H$_{68}$N$_{12}$O$_{11}$H: 1073.5203. found: 1073.5226; calcd for C$_{55}$H$_{68}$N$_{12}$O$_{11}$Na: 1095.5023. found: 1095.5008.

N-(6-Amino-1-(1-cyclohexylethylamino)-1-oxo-hexan-2-yl)-3-(3-(3-nitro-1H-pyrazole-5-carboxamido)-1H-pyrazole-5-carboxamido)-1H-pyrazole-5-carboxamide-trifluoro-acetate (Trimer-Lys-Che)

A portion of 54 mg (50 μmol, 1.00 equiv) of the PMB-protected Trimer-Lys-Che was treated with hot TFA according to the general procedure E to yield the free pyrazole trimer as a light-yellow solid. Yield: 24 mg (33 µmol, 66%).

$^1$H NMR (500 MHz, DMSO-d$_6$): δ [ppm]=0.85-1.02 (m, 5H, CH$_3$ (d, $^3$J=6.8 Hz), CH$_2$), 1.06-1.17 (m, 3H, CH, CH$_2$), 1.23-1.40 (m, 3H, CH, CH$_2$), 1.53-1.73 (m, 9H, CH$_2$, CH), 2.73-2.81 (m, 2H, CH$_2$-Lys), 3.58-3.65 (m, 1H, CH), 4.38-4.45 (m, 1H, α-CH-Lys), 7.38 (bs, 1H, NH-amide), 7.59 (bs, 1H, CH-pyrazole), 7.66 (bs, 3H, NH$_2$), 7.79 (bs, 1H, NH-amide), 7.95 (bs, 1H, CH-pyrazole), 8.54 (bs, 1H, CH-pyrazole), 11.14 (s, 1H, NH-amide), 11.45 (s, 1H, NH-amide), 13.24 (bs, 1H, NH-pyrazole), 13.49 (bs, 1H, NH-pyrazole), 14.98 (bs, 1H, NH-pyrazole). $^{13}$C NMR (125 MHz, DMSO-d$_6$): δ [ppm]=17.6, 17.7, 22.5, 25.6, 25.9, 26.6, 28.6, 28.7, 42.3, 48.5, 52.5, 98.1, 102.2, 138.6, 146.4, 155.0, 155.8, 157.7, 157.9, 170.5. Mp: decomposition at 211° C. HRMS (ESI): calcd for C$_{26}$H$_{36}$N$_{12}$O$_6$H: 613.2954. found: 613.2971; calcd for C$_{26}$H$_{35}$N$_{12}$O$_6$: 611.2808; found: 611.2804.

N-(1-Cyclohexylethyl)-1-(4-methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamide A portion of 150 mg (204 µmol, 1.09 equiv) of PMB-protected Trimer-OH and 27.70 µL (186 µmol, 1.00 equiv) of cyclohexylethylamine were reacted with 57 mg (223 µmol, 1.20 equiv) of Mukaiyama's reagent and 0.10 mL (574 µmol, 3.08 equiv) of diisopropylethylamine according to general procedure B. The crude product was purified by column chromatography on silica gel using n-pentane/ethyl acetate (2:1) to yield the PMB-protected Trimer-Che as a colorless solid. Yield: 131 mg (155 µmol, 83%).

$^1$H NMR (500 MHz, DMSO-d$_6$): δ [ppm]=0.85-0.97 (m, 2H, CH$_2$-cyclohexyl), 1.09 (d, $^3$J=6.8 Hz, 3H, CH$_3$), 1.13-1.19 (m, 2H, CH$_2$-cyclohexyl), 1.34-1.41 (m, 1H, CH), 1.59-1.74 (m, 4H, CH$_2$-cyclohexyl), 3.70-3.71 (3s, 9H, CH$_3$-PMB), 3.76-3.84 (m, 1H, CH), 5.55-5.63 (dd, $^3$J=9.0 Hz, $^3$J=14.5 Hz, 2H, CH$_2$-PMB), 5.68 (s, 2H, CH$_2$-PMB), 5.81 (s, 2H, CH$_2$-PMB), 6.85-6.91 (m, 6H, CH-arom.), 7.15-7.19 (m, 4H, CH-arom.), 7.25-7.28 (m, 2H, CH-arom.), 7.31 (s, 1H, CH-pyrazole), 7.71 (s, 1H, CH-pyrazole), 7.98 (s, 1H, CH-pyrazole), 8.35 (d, $^3$J=8.8 Hz, 1H, NH-amide), 11.33 (s, 1H, NH-amide), 11.50 (s, 1H, NH-amide). $^{13}$C NMR (125 MHz, CDCl$_3$): δ [ppm]=17.5, 25.6, 25.9, 28.9, 29.1, 42.2, 48.8, 52.7, 53.0, 54.9, 55.0, 99.4, 100.9, 105.0, 113.6, 113.8, 114.0, 127.9, 128.6, 128.9, 129.3, 129.5, 129.8, 134.4, 135.4, 136.7, 144.8, 145.0, 153.5, 155.4, 156.8, 158.4, 158.6, 159.0. Mp: 178° C. R$_f$: 0.42 n-pentane/ethyl acetate (2:1). HRMS (ESI): calcd for C$_{44}$H$_{49}$N$_{10}$O$_8$H: 845.3729. found: 845.3723; calcd for C$_{44}$H$_{49}$N$_{10}$O$_8$Na: 867.3549. found: 867.3552.

N-(1-Cyclohexylethyl)-3-(3-(3-nitro-1H-pyrazole-5-carboxamido)-1H-pyrazole-5-carboxamido)-1H-pyrazole-5-carboxamide (Trimer-Che)

A portion of 49 mg (58 µmol, 1.00 equiv) of PMB-protected Trimer-Che was treated with hot TFA according to the general procedure E to yield the free pyrazole trimer as a colorless solid. Yield: 23 mg (47 µmol, 82%).

$^1$H NMR (500 MHz, DMSO-d$_6$): δ [ppm]=0.90-1.22 (m, 8H, CH$_3$, CH$_2$-cyclohexyl), 1.37-1.42 (m, 1H, CH), 1.59-1.75 (m, 5H, CH$_2$-cyclohexyl), 3.78-3.84 (m, 1H, CH), 7.33 (s, 1H, CH-pyrazole), 7.60 (s, 1H, CH-pyrazole), 7.95 (s, 1H, CH-pyrazole), 8.26 (bs, 1H, NH-amide), 11.12 (s, 1H, NH-amide), 11.43 (s, 1H, NH-amide), 13.15 (s, 1H, NH-pyrazole), 13.46 (s, 1H, NH-pyrazole). $^{13}$C NMR (125 MHz, DMSO-d$_6$): δ [ppm]=15.1, 17.6, 25.6, 25.9, 28.9, 29.1, 42.3, 48.7, 64.8, 96.8, 98.1, 102.2, 138.6, 155.0, 155.8, 156.4, 158.1. Mp: decomposition at 265.6° C. HRMS (ESI): calcd for C$_{20}$H$_{25}$N$_{10}$O$_5$H: 485.2004. found: 485.1966.

4-(1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamido)butanoic acid methyl ester A portion of 300 mg (0.41 mmol, 1.00 equiv) of PMB-protected Trimer-OH and 63 mg (0.41 µmol, 1.00 equiv) of γ-aminobutanoic acid methyl ester hydrochloride were reacted with 156 mg (0.61 mmol, 1.50 equiv) of Mukaiyama's reagent and 0.32 mL (1.83 mmol, 4.50 equiv) of diisopropylethylamine according to general procedure B. The residue was purified by column chromatography on silica gel using n-pentane/ethyl acetate (2:1) to yield PMB-protected Trimer-GABA-OMe as a colorless solid. Yield: 193 mg (0.23 mmol, 57%).

$^1$H NMR (500 MHz, DMSO-d$_6$): δ [ppm]=1.74-1.79 (quin, $^3$J=7.1 Hz, 2H, CH$_2$), 2.34 (t, $^3$J=7.4 Hz, 2H, CH$_2$), 3.22-3.26 (q, $^3$J=6.0 Hz, $^3$J=6.6 Hz, 2H, CH$_2$), 3.59 (s, 3H, OOCH$_3$), 3.70-3.71 (3s, 9H, CH$_3$-PMB), 5.61 (s, 2H, CH$_2$-PMB), 5.67 (s, 2H, CH$_2$-PMB), 5.81 (s, 2H, CH$_2$-PMB), 6.86-6.91 (m, 6H, CH-arom.), 7.16-7.19 (m, 4H, CH-arom.), 7.25-7.28 (m, 2H, CH-arom.), 7.31 (s, 1H, CH-pyrazole), 7.71 (s, 1H, CH-pyrazole), 7.98 (s, 1H, CH-pyrazole), 8.66 (t, $^3$J=5.5 Hz, 1H, NH-amide), 11.34 (s, 1H, NH-amide), 11.50 (s, 1H, NH-amide). $^{13}$C NMR (125 MHz, DMSO-d$_6$): δ [ppm]=24.1, 30.6, 37.9, 51.2, 52.6, 53.1, 54.9, 55.0, 59.6, 99.4, 100.8, 105.0, 113.7, 113.8, 113.9, 127.9, 128.6, 128.9, 129.3, 129.5, 129.7, 134.3, 134.9, 136.7, 144.8, 145.1, 153.5, 155.4, 156.8, 158.6, 159.0, 173.0. Mp: 198.8-201.7° C. R$_f$: 0.08 n-pentane/ethyl acetate (2:1). HRMS (ESI): calcd for C$_{41}$H$_{42}$N$_{10}$O$_{10}$H: 835.3158. found: 835.3187; calcd for C$_{41}$H$_{42}$N$_{10}$O$_{10}$Na: 857.2978. found: 857.3001; calcd for C$_{41}$H$_{42}$N$_{10}$O$_{10}$K: 873.2717. found: 873.2751; calcd for C$_{41}$H$_{41}$N$_{10}$O$_{10}$: 833.3013; found: 833.2999.

4-(3-(3-(3-Nitro-1H-pyrazole-5-carboxamido)-1H-pyrazole-5-carboxamido)-1H-pyrazole-5-carboxamido)butanoic acid methyl ester (Trimer-GABA-OMe)

A portion of 60 mg (72 µmol, 1.00 equiv) of PMB-protected Trimer-GABA-OMe was treated with hot TFA according to the general procedure E to yield the free aminopyrazole as a colorless solid. Yield: 26 mg (55 µmol, 76%).

$^1$H NMR (500 MHz, DMSO-d$_6$): δ [ppm]=1.72-1.83 (quin, $^3$J=7.1 Hz, 2H, CH$_2$), 2.37 (t, $^3$J=7.4 Hz, 2H, CH$_2$), 3.23-3.29 (q, $^3$J=6.0 Hz, $^3$J=6.9 Hz, 2H, CH$_2$), 3.59 (s, 3H, CH$_3$), 7.16 (bs, 1H, CH-pyrazole), 7.53 (bs, 1H, CH-pyrazole), 7.94 (s, 1H, CH-pyrazole), 8.53 (t, $^3$J=5.4 Hz, 1H, NH), 11.08 (bs, 1H, NH-amide), 11.44 (s, 1H, NH-amide). $^{13}$C NMR (125 MHz, DMSO-d$_6$): δ [ppm]=24.3, 24.4, 30.6, 31.0, 37.8, 51.2, 87.4, 96.6, 102.2, 155.0, 155.8, 173.0, 174.1. Mp: decomposition at 242° C. HRMS (ESI): calcd for C$_{17}$H$_{17}$N$_{10}$O$_7$: 473.1287; found: 473.1317.

4-(1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamido)butanoic acid A 70 mg (84 µmol, 1.00 equiv) amount of PMB-protected Trimer-GABA-OMe and 10 mg lithium hydroxide (418 µmol, 4.98 equiv) were stirred in a mixture of methanol/THF/ water (5:5:1) for two days at room temperature. The pure product was prepared according to general procedure A as a colorless solid. Yield: 57 mg (69 µmol, 83%).

$^1$H NMR (500 MHz, DMSO-d$_6$): δ [ppm]=1.71-1.77 (quin, $^3$J=7.1 Hz, 2H, CH$_2$), 2.34 (t, $^3$J=7.4 Hz, 2H, CH$_2$), 3.22-3.26 (q, $^3$J=5.8 Hz, $^3$J=6.5 Hz, 2H, CH$_2$), 3.70-3.71 (3s, 9H, CH$_3$-PMB), 5.61 (s, 2H, CH$_2$-PMB), 5.67 (s, 2H, CH$_2$-PMB), 5.81 (s, 2H, CH$_2$-PMB), 6.86-6.91 (m, 6H, CH-arom.), 7.16-7.20 (m, 4H, CH-arom.), 7.25-7.28 (m, 2H, CH-arom.), 7.32 (s, 1H, CH-pyrazole), 7.71 (s, 1H, CH-pyrazole), 7.98 (s, 1H, CH-pyrazole), 8.66 (t, $^3$J=5.7 Hz, 1H, NH-amide), 11.33 (s, 1H, NH-amide), 11.50 (s, 1H, NH-amide). $^{13}$C NMR (125 MHz, DMSO-d$_6$): δ [ppm]=24.2, 30.9, 38.1, 52.6, 53.1, 54.9, 55.0, 60.1, 72.2, 99.4, 100.8, 105.0, 113.7, 113.8, 114.0, 127.9, 128.7, 128.9, 129.3, 129.5, 129.7, 134.3, 135.0, 136.7, 144.8, 145.1, 153.5, 155.4, 156.8, 158.6, 159.0, 174.1. Mp: 209.3-211° C. HRMS (ESI): calcd for C$_{40}$H$_{41}$N$_{10}$O$_{10}$Na: 843.2821. found: 843.2849.

4-(3-(3-(3-Nitro-1H-pyrazole-5-carboxamido)-1H-pyrazole-5-carboxamido)-1H-pyrazole-5-carboxamido)butanoic acid (Trimer-GABA-OH)

A portion of 50 mg (61 µmol, 1.00 equiv) of PMB-protected Trimer-GABA-OH was treated with hot TFA according to general procedure E to yield the free aminopyrazole trimer as a beige solid. Yield: 22 mg (48 µmol, 78%).

$^1$H NMR (500 MHz, DMSO-d$_6$): δ [ppm]=1.72-1.78 (quin, $^3$J=7.1 Hz, 2H, CH$_2$), 2.28 (t, $^3$J=7.4 Hz, 2H, CH$_2$), 3.24-3.28 (q, $^3$J=6.0 Hz, $^3$J=6.9 Hz, 2H, CH$_2$), 7.20 (bs, 1H, CH-pyrazole), 7.58 (bs, 1H, CH-pyrazole), 7.94 (s, 1H, CH-pyrazole), 8.53 (bs, 1H, H-6), 11.11 (brs, 1H, NH-amide), 11.43 (s, 1H, NH-amide), 13.20 (brs, 1H, NH-pyrazole), 13.49 (brs, 1H, NH-pyrazole), 14.98 (s, 1H, NH-pyrazole). $^{13}$C NMR (125 MHz, DMSO-d$_6$): δ [ppm]=24.4, 31.0, 37.9, 96.7, 98.1, 102.2, 138.6, 155.0, 155.8, 174.1. Mp: decomposition at 231° C. HRMS (ESI): calcd for C$_{16}$H$_{15}$N$_{10}$O$_7$: 459.1120; found: 459.1143.

tert-Butyl-2-(1-(4-methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamido)ethylcarbamate A 146 mg (198 µmol, 1.00 equiv) amount of PMB-protected Trimer-OH was dissolved in 20 mL dichlormethane and cooled to 0° C. To this suspension 80 mg HOBt (592 µmol, 2.98 equiv), 114 mg EDC-HCl (595 µmol, 3.00 equiv) and 64 mg (399 µmol, 2.01 equiv) tert-butyl-2-aminoethylcarbamate were added according to general procedure D. After workup, the crude product was purified by column chromatography on silica gel using n-pentane/ethyl acetate (2:1) to yield the coupled product as a light yellow solid. Yield: 142 mg (162 µmol, 82%).

$^1$H NMR (500 MHz, DMSO-d$_6$): δ [ppm]=1.37 (s, 9H, (CH$_3$)$_3$), 3.06-3.12 (m, 2H, CH$_2$), 3.23-3.28 (m, 2H, CH$_2$), 3.70-3.71 (2s, 9H, CH$_3$-PMB), 5.61 (s, 2H, CH$_2$-PMB), 5.67 (s, 2H, CH$_2$-PMB), 5.81 (s, 2H, CH$_2$-PMB), 6.86-6.91 (m, 7H, H-4, CH-arom.), 7.16-7.21 (m, 4H, CH-arom.), 7.26-7.29 (m, 2H, CH-arom.), 7.32 (s, 1H, CH-pyrazole), 7.71 (s, 1H, CH-pyrazole), 7.98 (s, 1H, CH-pyrazole), 8.63 (t, $^3$J=5.7 Hz, 1H, NH-amide), 11.34 (s, 1H, NH-amide), 11.51 (s, 1H, NH-amide). $^{13}$C NMR (125 MHz, DMSO-d$_6$): δ [ppm]=18.5, 20.6, 28.1, 30.1, 52.6, 53.1, 54.9, 55.0, 63.4, 77.6, 99.5, 100.9, 105.0, 113.7, 113.8, 114.0, 127.9, 128.7, 129.3, 129.5, 129.7, 134.3, 134.9, 136.7, 144.8, 145.2, 153.5, 155.4, 155.6, 156.8, 158.6, 159.0, 159.1, 170.3, 171.9. Mp: 117.8° C. R$_f$: 0.06 n-pentane/ethyl acetate (2:1). HRMS (ESI): calcd for C$_{43}$H$_{47}$N$_{11}$O$_{10}$H: 878.3580. found: 878.3596; calcd for C$_{43}$H$_{47}$N$_{11}$O$_{10}$Na: 900.3400. found: 900.3420.

N-(2-Aminoethyl)-3-(3-(3-nitro-1H-pyrazole-5-carboxamido)-1H-pyrazole-5-carboxamido)-1H-pyrazole-5-carboxamide (Trimer-diamine)

A portion of 52 mg (59 µmol, 1.00 equiv) of PMB-protected Trimer-diamine was treated with hot TFA according to general procedure E to yield the free aminopyrazole trimer as a colorless solid. Yield: 16 mg (30 µmol, 51%).

$^1$H NMR (500 MHz, DMSO-d$_6$): δ [ppm]=2.99 (bs, 2H, CH$_2$), 3.48 (bs, 2H, CH$_2$), 7.28 (bs, 1H, CH-pyrazole), 7.61 (brs, 1H, CH-pyrazole), 7.78 (bs, 1H, NH$_2$), 7.95 (bs, 1H, CH-pyrazole), 8.68 (bs, 1H, NH-amide), 11.18 (bs, 1H, NH-amide), 11.42 (bs, 1H, NH-amide), 13.31 (bs, 1H, NH-pyrazole), 13.47 (bs, 1H, NH-pyrazole). $^{13}$C NMR (125 MHz, DMSO-d$_6$): δ [ppm]=36.5, 102.3, 136.4, 136.5, 138.6, 155.0, 156.3, 159.2. Mp: decomposition at 256° C. HRMS (ESI): calcd for C$_{14}$H$_{15}$N$_{11}$O$_5$Na: 440.1150. found: 440.1188.

Ethyl 2-(2-(2-(2-aminoethoxy)ethoxy)ethoxy)acetate

To a solution of {2-[2-(2-Azido-ethoxy)-ethoxy]-ethoxy}-acetic acid ethyl ester (0.30 g, 1.15 mmol, 1 eq) in ethanol (7 mL) was added 1M HCl (2.30 mL, 2.30 mmol, 2 eq) and 30.0 mg of Pd/C (10%). The flask was then evacuated and filled with H$_2$. The mixture was stirred under H$_2$ atmosphere at room temperature until the starting material disappeared on the TLC plate and in mass spectra. The solution was filtered through celite and concentrated in vacuo to give a pale yellow syrup. The obtained 2-[2-(2-ethoxycarbonylmethoxy-ethoxy)-ethoxy]-ethyl-ammonium chloride can be stored at –18° C. for several months. Work-up to get the free amine should only be performed immediately before the next step. To obtain the free amine 350 mg (1.29 mmol) of the respective hydrochloride were dissolved in chloroform. The organic layer was washed with sat. aq K$_2$CO$_3$ and H$_2$O, and the solvent was evaporated in vacuo at room temperature to give a colorless oil. Yield: 210 mg (0.89 mmol, 69%).

$^1$H-NMR (500 MHz, CDCl$_3$): δ [ppm]=1.28 (t, 3H, CH$_3$), 1.85 (brs, 2H, NH$_2$), 2.88 (t, 2H, CH$_2$), 3.53 (t, 2H, CH$_2$), 3.61-3.76 (m, 8H, CH$_2$), 4.15 (s, 2H, CH$_2$), 4.21 (q, 2H, CH$_2$). $^{13}$C-NMR (125.7 MHz, CDCl$_3$): δ [ppm]=14.3, 41.8, 60.9, 68.8, 70.4, 70.6, 70.7, 71.0, 73.2, 170.6. HRMS (ESI): m/z calcd for C$_{10}$H$_{22}$NO$_5$: 236.1492; found: 236.1511, calcd for C$_{10}$H$_{21}$NNaO$_5$: 258.1312; found: 258.1325.

1-(1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-yl)-1-oxo-5,8,11-trioxa-2-azatridecan-13-oic acid ethyl ester A 200 mg (272 µmol, 1.00 equiv) amount of compound PMB-protected Trimer-OH was dissolved in 20 mL dichlormethane and cooled to 0° C. To this suspension 97 mg HOBt (828 µmol, 3.05 equiv), 156 mg EDC-HCl (816 µmol, 3.00 equiv) and 128 mg (544 µmol, 2.00 equiv) ethyl-2-{2-[2-(aminoethoxy)ethoxy]-ethoxy}acetate were added according to the general procedure D. After workup, the crude product was purified by column chromatography on silica gel using dichlormethane/methanol (70:1) to yield the pure coupling product as a colorless solid. Yield: 207 mg (218 µmol, 80%).

$^1$H NMR (500 MHz, CDCl$_3$): δ [ppm]=1.24 (t, $^3$J=7.1 Hz, 3H, CH$_3$), 3.58-3.74 (m, 12H, CH$_2$), 3.76-3.77 (2s, 9H, CH$_3$-

PMB), 4.11 (s, 2H, CH$_2$), 4.13-4.21 (q, $^3J$=7.1 Hz, 2H, CH$_2$), 5.63 (s, 4H CH$_2$-PMB), 5.80 (s, 2H, CH$_2$-PMB), 6.79-6.89 (m, 7H, H-11, CH-arom.), 7.11 (s, 1H, CH-pyrazole), 7.24-7.30 (m, 6H, CH-pyrazole, CH-arom.), 7.37-7.41 (m, 2H, CH-arom.), 8.40 (s, 1H, NH-amide), 8.43 (s, 1H, NH-amide). $^{13}$C NMR (125 MHz, CDCl$_3$): δ [ppm]=14.1, 39.5, 53.7, 53.9, 55.2, 55.9, 60.9, 68.6, 69.5, 70.3, 70.4, 70.5, 70.8, 98.1, 98.9, 103.7, 113.9, 114.1, 127.1, 128.7, 129.2, 130.0, 134.7, 135.7, 136.1, 144.7, 154.1, 155.1, 156.2, 159.2, 159.3, 159.5, 159.7, 170.5. Mp: 78.6° C. R$_f$: 0.18 dichlormethane/methanol (70:1). HRMS (ESI): calcd for C$_{46}$H$_{52}$N$_{10}$O$_{13}$H: 953.3788. found: 953.3766; calcd for C$_{43}$H$_{47}$N$_{11}$O$_{10}$Na: 975.3608. found: 975.3591.

1-(3-(3-(3-Nitro-1H-pyrazole-5-carboxamido)-1H-pyrazole-5-carboxamido)-1H-pyrazole-5-yl)-1-oxo-5,8,11-trioxa-2-azatridecan-13-oic acid ethyl ester (Trimer-TEG-OEt)

A portion of 49 mg (52 μmol, 1.00 equiv) of PMB-protected Trimer-TEG-OEt was treated with hot TFA according to general procedure E to yield the pure aminopyrazole trimer as a colorless solid. Yield: 30 mg (51 μmol, 98%).

$^1$H NMR (500 MHz, DMSO-d$_6$): δ [ppm]=1.18 (t, $^3J$=7.1 Hz, 3H, CH$_3$), 3.38-3.42 (m, 2H, CH$_2$), 3.53-3.59 (m, 10H, CH$_2$), 4.08-4.12 (m, 4H, CH$_2$), 7.27 (bs, 1H, CH-pyrazole), 7.59 (s, 1H, CH-pyrazole), 7.95 (s, 1H, CH-pyrazole), 8.40 (s, 1H, NH-amide), 11.12 (bs, 1H, NH-amide), 11.43 (bs, 1H, NH-amide), 13.22 (bs, 1H, NH-pyrazole), 13.48 (bs, 1H, NH-pyrazole), 14.98 (bs, 1H, NH-pyrazole). $^{13}$C NMR (125 MHz, DMSO-d$_6$): δ [ppm]=14.0, 60.0, 67.6, 68.7, 69.5, 69.6, 69.9, 98.2, 102.2, 138.6, 146.4, 146.5, 155.0, 155.8, 156.3, 170.0. Mp: decomposition at 264.3° C. HRMS (ESI): calcd for C$_{22}$H$_{28}$N$_{10}$O$_{10}$H: 593.2063. found: 593.2071; calcd for C$_{22}$H$_{28}$N$_{10}$O$_{10}$Na: 615.1882. found: 615.1899.

1-(1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-yl)-1-oxo-5,8,11-trioxa-2-azatridecan-13-oic acid A 153 mg (161 μmol, 1.00 equiv) amount of PMB-protected Trimer-TEG-OEt and 14 mg lithium hydroxide (585 μmol, 3.64 equiv) were stirred in a mixture of methanol/THF/water (5:5:1) for two days at room temperature. The pure product was prepared according to general procedure A to yield the free carboxylic acid as a colorless solid. Yield: 137 mg (148 μmol, 92%).

$^1$H NMR (500 MHz, CDCl$_3$): δ [ppm]=3.36-3.40 (m, 2H, CH$_2$), 3.51-3.58 (m, 10H, CH$_2$), 3.70-3.71 (2s, 9H, CH$_3$-PMB), 4.00 (s, 2H, CH$_2$), 5.61 (s, 2H, CH$_2$-PMB), 5.67 (s, 2H, CH$_2$-PMB), 5.81 (s, 2H, CH$_2$-PMB), 6.86-6.91 (m, 6H, CH-arom.), 7.16-7.19 (m, 4H, CH-arom.), 7.26-7.28 (m, 6H, CH-arom.), 7.33 (s, 1H, CH-pyrazole), 7.71 (s, 1H, CH-pyrazole), 7.98 (s, 1H, CH-pyrazole), 8.71 (t, $^3J$=5.5 Hz, 1H, NH), 11.33 (s, 1H, NH-amide), 11.50 (s, 1H, NH-amide), 12.55 (bs, 1H, H-1). $^{13}$C NMR (125 MHz, DMSO-d$_6$): δ [ppm]=52.7, 53.1, 55.0, 67.5, 68.5, 69.4, 69.6, 69.7, 99.5, 100.8, 105.0, 113.7, 113.8, 113.9, 127.9, 128.7, 128.9, 129.3, 129.5, 129.7, 134.3, 134.8, 136.7, 144.8, 145.1, 153.5, 155.4, 156.8, 158.5, 158.6, 159.0, 159.1, 171.5. Mp: 88° C. HRMS (ESI): calcd for C$_{44}$H$_{48}$N$_{10}$O$_{13}$H: 925.3475. found: 925.3445; calcd for C$_{44}$H$_{48}$N$_{10}$O$_{13}$Na: 947.3295. found: 947.3251.

{2-[2-(2-{[5-({5-[(5-Nitro-2H-pyrazole-3-carbonyl)-amino]-2H-pyrazole-3-carbonyl}-amino)-2H-pyrazole-3-carbonyl]-amino}-ethoxy)-ethoxy]-ethoxy}-acetic acid (Trimer-TEG-OH)

A portion of 53.0 mg (57.4 μmol) of Trimer(PMB)-TEG-OH OMe was treated with hot TFA according to general procedure E to yield Trimer-TEG-OH as a colorless solid. Yield: 30 mg (53.2 μmol, 94%).

$^1$H-NMR (500 MHz, DMSO): δ [ppm]=3.39-3.40 (m, 2H, CH$_2$), 3.52-3.57 (m, 10H, CH$_2$), 4.01 (s, 2H, CH$_2$), 7.16 (brs, 1H, NH-amide), 7.57 (s, 1H, CH-pyrazole), 7.94 (s, 1H, CH-pyrazole), 8.55 (s, 1H, CH-pyrazole), 11.09 (s, 1H, NH-amide), 11.43 (brs, 1H, NH-amide), 12.75 (s, 1H, NH-pyrazole), 13.09 (s, 1H, NH-pyrazole), 13.51 (brs, 1H, CO$_2$H), 14.98 (s, 1H, NH-pyrazole). $^{13}$C-NMR (500 MHz, DMSO): δ [ppm]=39.5, 68.4, 69.7, 70.5, 70.56, 70.6, 70.7, 103.2, 139.6, 155.9, 156.8, 172.5. Mp: decomposition at 349° C. HRMS (ESI): m/z calcd for C$_{20}$H$_{24}$N$_{10}$NaO$_{10}$: 587.1569; found: 587.1553; for C$_{20}$H$_{23}$N$_{10}$Na$_2$O$_{10}$: 609.1389, found: 609.1388.

N-(13-Cyclohexyl-11-oxo-3,6,9-trioxa-12-azatetradecyl)-1-(4-methoxy-benzyl)-3-(1-(4-methoxybenzyl)-3-(1-(4-methoxybenzyl)-3-nitro-1H-pyrazole-5-carbox-amido)-1H-pyrazole-5-carboxamido)-1H-pyrazole-5-carboxamide A portion of 110 mg (119 μmol, 1.09 equiv) of compound PMB-protected Trimer-TEG-OH and 16 μL (109 μmol, 1.00 equiv) of cyclohexylethylamine were reacted with 41 mg (161 μmol, 1.47 equiv) of Mukaiyama's reagent and 56.50 μL (324 μmol, 2.98 equiv) of diisopropylethylamine according to general procedure B. The residue was purified by column chromatography on silica gel using dichlormethane/methanol (70:1) to yield the coupled product as a colorless solid. Yield: 84 mg (81 μmol, 75%).

$^1$H NMR (500 MHz, DMSO-d$_6$): δ [ppm]=0.81-0.92 (m, 2H, CH$_2$), 1.00 (d, $^3J$=6.7 Hz, 3H, CH$_3$), 1.04-1.07 (m, 3H, CH, CH$_2$), 1.23-1.28 (m, 1H, CH), 1.55-1.66 (m, 5H, CH, CH$_2$), 3.55-3.71 (m, 21H, CH$_2$, CH$_3$-PMB), 4.85 (s, 2H, CH$_2$), 5.61 (s, 2H, CH$_2$-PMB), 5.66 (s, 2H, CH$_2$-PMB), 5.81 (s, 2H, CH$_2$-PMB), 6.86-6.91 (m, 6H, CH-arom.), 7.16-7.19 (m, 4H, CH-arom.), 7.24-7.33 (m, 4H, H-7, CH-pyrazole, CH-arom.), 7.70 (s, 1H, CH-pyrazole), 7.97 (s, 1H, CH-pyrazole), 8.70 (t, $^3J$=5.2 Hz, 1H, NH), 11.33 (s, 1H, NH-amide), 11.50 (s, 1H, NH-amide). $^{13}$C NMR (125 MHz, DMSO-d$_6$): δ [ppm]=17.6, 25.6, 25.9, 28.8, 38.6, 42.2, 48.1, 52.7, 53.1, 55.0, 55.1, 68.6, 69.5, 69.7, 70.2, 99.6, 100.9, 105.0, 113.7, 113.8, 114.0, 127.9, 128.7, 128.9, 129.3, 129.5, 129.7, 134.3, 134.9, 136.7, 144.8, 145.2, 153.5, 155.4, 158.6, 159.0, 159.1, 168.3. Mp: 189.9-191.2° C. R$_f$: 0.35 dichlormethane/methanol (70:1). HRMS (ESI): calcd for C$_{52}$H$_{63}$N$_{11}$O$_{12}$H: 1034.4730. found: 1034.4757; calcd for C$_{52}$H$_{63}$N$_{11}$O$_{12}$Na: 1056.4550. found: 1056.4588.

N-(13-Cyclohexyl-11-oxo-3,6,9-trioxa-12-azatetradecyl)-3-(3-(3-nitro-1H-pyrazole-5-carboxamido)-1H-pyrazole-5-carboxamido)-1H-pyrazole-5-carboxamide (Trimer-TEG-Che)

A portion of 42 mg (41 μmol, 1.00 equiv) of PMB-protected Trimer-TEG-Che was treated according to general procedure E to yield the free aminopyrazole as a colorless solid. Yield: 20 mg (30 μmol, 72%).

$^1$H NMR (500 MHz, DMDO-d$_6$): δ [ppm]=0.83-1.33 (m, 9H, CH$_3$, CH$_2$-cyclohexyl), 1.56-1.67 (m, 5H, CH-cyclohexyl, CH$_2$-cyclohexyl), 3.39-3.39 (m, 13H, CH, CH$_2$), 3.86 (s, 2H, CH$_2$), 7.26-7.29 (bs, 2H, CH-pyrazole, NH-amide), 7.59 (bs, 1H, CH-pyrazole), 7.95 (s, 1H, CH-pyrazole), 8.64 (bs, 1H, NH-amide), 11.14 (bs, 1H, NH-amide), 11.44 (bs, 1H, NH-amide), 13.22 (bs, 1H, NH-pyrazole), 13.48 (bs, 1H, NH-pyrazole). $^{13}$C NMR (125 MHz, DMSO-d$_6$): δ [ppm]= 17.6, 25.6, 25.9, 28.7, 28.8, 38.4, 42.1, 48.1, 51.0, 59.9, 60.1, 68.7, 69.5, 69.7, 70.2, 80.5, 102.2, 138.6, 155.0, 155.8, 168.2. Mp: decomposition at 153° C. HRMS (ESI): calcd for C$_{28}$H$_{39}$N$_{11}$O$_9$Na: 696.2824. found: 696.2808; calcd for C$_{28}$H$_{38}$N$_{11}$O$_9$Na: 672.2859. found: 672.2874.

N-(1-Cyclohexyl-2-(1-cyclohexylethylamino)-2-oxoethyl)-1-(4-methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamide A portion of 200 mg (0.27 mmol, 1.00 equiv) of PMB-protected Trimer-OH and 103 mg (0.27 mmol, 1.00 equiv) of 2-Amino-2-cyclohexyl-N-(1-cyclohexylethyl)acetamide-trifluoroacetate were reacted with 104 mg (0.41 mmol, 1.50 equiv) of Mukaiyama's reagent and 0.21 mL (1.21 mmol, 4.45 equiv) of diisopropylethylamine according to general procedure B. The crude product was purified by column chromatography on silica gel using dichlormethane/ethyl acetate (7:1) to yield the coupled product as a colorless solid. Yield: 128 mg (0.13 mmol, 48%).
$^1$H NMR (500 MHz, DMSO-d$_6$): δ [ppm]=0.89-1.18 (m, 13H, CH$_3$, CH$_2$), 1.26-1.32 (m, 1H, CH), 1.56-1.80 (m, 11H, CH, CH$_2$), 3.59-3.63 (m, 1H, CH), 3.70-3.71 (2s, 9H, CH$_3$-PMB), 4.28 (t, $^3$J=8.6 Hz, 1H, CH), 5.53-5.60 (dd, $^3$J=14.5 Hz, $^3$J=5.7 Hz, 2H, CH$_2$-PMB), 5.67 (s, 2H, CH$_2$-PMB), 5.81 (s, 2H, CH$_2$-PMB), 6.82-6.80 (m, 6H, CH-arom.), 7.16-7.18 (m, 4H, CH-arom.), 7.26-7.28 (m, 2H, CH-arom.), 7.40 (s, 1H, CH-pyrazole), 7.71 (s, 1H, CH-pyrazole), 7.79 (d, $^3$J=8.5 Hz, 1H, NH-amide), 7.97 (s, 1H, CH-pyrazole), 8.46 (d, $^3$J=8.8 Hz, 1H, NH-amide), 11.32 (s, 1H, NH-amide), 11.50 (s, 1H, NH-amide). $^{13}$C NMR (125 MHz, DMSO-d$_6$): δ [ppm]=17.3, 25.6, 25.7, 28.5, 28.6, 28.7, 42.0, 55.0, 68.2, 100.8, 113.6, 113.8, 114.0, 127.9, 128.7, 128.9, 129.3, 129.5, 129.6, 134.8, 136.7, 156.8, 158.6, 158.9, 159.0, 169.2, 169.5. Mp: 216° C. R$_f$: 0.40 dichlormethane/ethyl acetate (7:1). HRMS (ESI): calcd for C$_{52}$H$_{61}$N$_{11}$O$_9$H: 984.4726. found: 984.4737; calcd for C$_{52}$H$_{61}$N$_{11}$O$_9$Na: 1006.4546. found: 1006.4492.

N-(1-Cyclohexyl-2-(1-cyclohexylethylamino)-2-oxoethyl)-3-(3-(3-nitro-1H-pyrazol-5-carboxamido)-1H-pyrazol-5-carboxamido)-1H-pyrazol-5-carboxamide (Trimer-Chg-Che)

A portion of 30 mg (30 µmol, 1.00 equiv) of PMB-protected Trimer-Chg-Che was treated according to general procedure E to yield the free aminopyrazole trimer as a colorless solid. Yield: 17 mg (27 µmol, 89%).
$^1$H NMR (500 MHz, DMSO-d$_6$): δ [ppm]=0.89-1.21 (m, 13H, OOCH$_3$, CH$_2$-cyclohexyl), 1.27-1.33 (m, 1H, CH-cyclohexyl), 1.59-1.79 (m, 11H, CH-cyclohexyl, CH$_2$-cyclohexyl), 3.60-3.66 (m, 1H, CH), 4.33 (bs, 1H, CH), 7.39 (bs, 1H, CH-pyrazole), 7.60 (bs, 1H, CH-pyrazole), 7.86 (bs, 1H, H-7), 7.96 (s, 1H, CH-pyrazole), 8.35 (bs, 1H, NH), 11.11 (bs, 1H, NH-amide), 11.42 (bs, 1H, NH-amide), 13.23 (bs, 1H, NH-pyrazole), 13.47 (bs, 1H, NH-pyrazole). $^{13}$C NMR (125 MHz, DMSO-d$_6$): δ [ppm]=17.2, 25.3, 25.4, 25.6, 25.9, 28.4, 28.5, 28.7, 29.1, 30.3, 42.0, 48.6, 57.6, 98.0, 98.2, 102.2, 136.4, 136.5, 138.6, 146.5, 146.4, 146.6, 155.0, 155.2, 155.8, 169.6. Mp: decomposition at 248.6° C. HRMS (ESI): calcd for C$_{28}$H$_{36}$N$_{11}$O$_6$: 622.2856; found: 622.2878.

Methyl 15-(4-(tert-butoxycarbonylamino)butyl)-1-(1-(4-methoxybenzyl)-3-(1-(4-methoxybenzyl)-3-(1-(4-methoxybenzyl)-3-nitro-1H-pyrazole-5-carboxamido)-1H-pyra-zole-5-carboxamido)-1H-pyrazol-5-yl)-1,13-dioxo-5,8,11-trioxa-2,14-diazahexa-decan-16-oate [Trimer(PMB)-TEG-Lys(Boc)-OMe]

In an argon atmosphere 105 mg (0.11 mmol, 1 eq) of PMB-protected Trimer-TEG-OH, 39 µL (35 mg, 0.34 mmol, 3 eq) of PYBOP, 39 µL (35 mg, 0.34 mmol, 3 eq) of N-methylmorpholine (NMM) and 60 mg (0.20 mmol, 1.8 eq) N-ε-tert.-butyloxycarbonyl-(S)-lysine methyl ester were dissolved in dry dichloromethane (30 mL) and the solution was heated to 40° C. for 4 days. Dichloromethane was evaporated and the remaining residue was purified over a silica gel column, eluting with dichloromethane/methanol (50:1) to yield the product as a colorless solid. Yield 108 mg (82%, 0.11 mmol).
$^1$H-NMR (500 MHz, CDCl$_3$): δ [ppm]=1.25-1.41 (m, 13H, CH$_2$, CH$_3$-boc), 1.58-1.83 (m, 2H, CH$_2$), 3.00 (brs, 2H, CH$_2$), 3.56-3.58 (m, 2H, CH$_2$), 3.61-3.67 (m, 13H, CH$_2$, CH$_3$), 3.72-3.76 (3s, 9H, CH$_3$-PMB), 4.02 (s, 2H, CH$_2$), 4.61-4.65 (m, 1H, CH), 5.60-5.79 (2s, 6H, CH$_2$-PMB), 6.76-6.81 (m, 6H, CH-arom), 7.09-7.40 (m, 11H, CH-arom, CH-pyrazole, NH-amide), 8.68 (s, 1H, NH-amide), 9.25 (s, 1H, NH-amide). $^{13}$C-NMR (125.7 MHz, CDCl$_3$): δ [ppm]=22.8, 28.6, 29.6, 32.2, 39.6, 40.3, 51.5, 52.5, 53.9, 54.0, 55.4, 56.1, 69.7, 70.3, 70.4, 70.5, 70.6, 71.0, 98.4, 99.3, 104.0, 114.0, 114.1, 114.2, 127.4, 129.0, 129.3, 129.4, 129.5, 130.2, 134.9, 135.8, 136.4, 114.9, 154.3, 155.4, 156.2, 156.5, 159.3, 159.4, 159.7, 159.9, 170.3, 172.9. Rf: 0.16 in dichlormethane/methanol (50:1). Mp: 79° C. HRMS (ESI): m/z calcd for C$_{56}$H$_{71}$N$_{12}$NaO$_{16}$: 1167.5106; found: 1167.5169; calcd for C$_{56}$H$_{20}$N$_{12}$NaO$_{16}$: 1189.4925, found: 1189.4979.

Trifluoro-acetate5-methoxycarbonyl-5-(2-{2-[2-(2-{[5-({5-[(5-nitro-2H-pyrazole-3-carbonyl)-amino]-2H-pyrazole-3-carbonyl}-amino)-2H-pyrazole-3-carbonyl]-amino}-ethoxy)-ethoxy]ethoxy}-acety-lamino)-pentyl-ammonium (Trimer-TEG-Lys-OMe)

In an argon atmosphere 50.0 mg (42.9 µmol) of Trimer (PMB)TEG-Lys(Boc)-OMe were heated in anhydrous TFA (3 mL) to 70° C. for 5 h. After adding cold Et$_2$O, the product precipitated. The precipitate was filtered, washed with Et$_2$O and dried in vacuo; Yield: 32.0 mg (39.0 µmol, 91%), colorless solid.
$^1$H-NMR (500 MHz, DMSO-d$_6$): δ [ppm]=1.30-1.36 (m, 2H, CH$_2$), 1.50-1.57 (m, 2H, CH$_2$), 1.62-1.80 (m, 2H, CH$_2$), 2.77 (brs, 2H, CH$_2$), 3.40-3.44 (m, 2H, CH$_2$), 3.54-3.60 (m, 10H, CH$_2$), 3.64 (s, 3H, CH$_3$), 3.95 (s, 2H, CH$_2$), 4.31-4.34 (m, 1H, CH), 7.28 (s, 1H, H—CH-pyrazole), 7.60-7.63 (m, 4H, H-33, CH-pyrazole), 7.95-7.98 (m, 2H, H-27, CH-pyrazole), 8.64 (brs, 1H, NH-amide), 11.13 (s, 1H, N—NH-amide), 11.41 (s, 1H, NH-amide), 13.24 (s, 1H, NHpyrazole), 13.47 (s, 1H, NHpyrazole), 14.97 (s, 1H, NHpyrazole). $^{13}$C-NMR (125.7 MHz, DMSO-d$_6$): δ [ppm]=22.3, 26.5, 30.2, 38.6, 51.1, 52.0, 68.8, 69.5, 69.7, 70.2, 97.2, 98.4, 102.2, 146.7, 158.6, 169.6, 172.2. Mp: decomposition at 360° C. HRMS (ESI): calcd for C$_{27}$H$_{39}$N$_{12}$H$_{11}$: 707.2856; found: 707.2851; calcd for C$_{27}$H$_{38}$N$_{12}$NaO$_{11}$: 729.2675; found: 729.2670.

1-(4-Methoxybenzyl)-3-(1-(4-methoxybenzyl)-3-(1-(4-methoxybenzyl)-3-nitro-1H-pyrazole-5-carboxamido)-1H-pyrazole-5-carboxamido)-N-(11-oxo-3,6,9-trioxa-12-azatetracosyl)-1H-pyrazole-5-carboxamide (Trimer(PMB)-TEG-dodecyl)

A 50.0 mg (54.1 µmol, 1.00 equiv) amount of Tri(PMB)-TEG-OH and 20.0 mg (0.11 mmol, 2.00 equiv) of dodecylamine were reacted with 19.0 mg (0.16 mmol, 3.00 equiv) of HOBt and 31.0 mg (0.16 mmol, 3.00 equiv) of EDC*HCl according to general procedure D. The residue was purified by column chromatography on silica gel using dichloromethane/methanol (50:1). Yield: 44.3 mg (40.6 µmol, 75%), pale yellow solid.

$^1$H-NMR (500 MHz, CDCl$_3$): δ [ppm]=0.86 (t, 3H, CH$_3$), 1.22 (brs, 18H, CH$_2$), 1.42-1.50 (m, 2H, CH$_2$), 3.20-3.26 (m, 2H, CH$_2$), 3.56-3.64 (m, 10H, CH$_2$), 3.72-3.75 (3s, 9H, CH$_3$-PMB), 4.00 (s, 2H, CH$_2$), 5.59-5.78 (2s, 6H, CH$_2$-PMB), 6.75-6.81 (m, 6H, CH-arom), 6.88 (t, 1H, NH-amide), 6.97 (t, 1H, NH-amide), 7.11 (s, 1H, CH-pyrazole), 7.17-7.26 (m, 5H, CH-arom, CH-pyrazole), 7.34-7.38 (m, 3H, CH-arom, CH-pyrazole), 8.62 (s, 1H, NH-amide), 9.13 (s, 1H, NH-amide). $^{13}$C-NMR (125.7 MHz, CDCl$_3$): δ [ppm]=14.2, 22.8, 27.9, 29.4, 29.5, 29.6, 29.7, 29.8, 29.9, 32.0, 39.1, 39.6, 53.9, 54.0, 55.4, 56.1, 69.8, 70.4, 70.5, 70.6, 70.7, 70.8, 98.2, 99.1, 103.9, 114.0, 114.1, 114.2, 127.3, 128.9, 129.3, 129.4, 129.5, 130.2, 134.8, 135.8, 136.4, 144.9, 154.2, 155.3, 156.5, 159.3, 159.5, 159.6, 159.9, 170.1. Mp: 105° C. R$_f$: 0.27 in dichloromethane/methanol (50:1). HRMS (ESI): m/z calcd for C$_{56}$H$_{74}$N$_{11}$O$_{12}$: 1092.5513; found: 1092.5521; calcd for C$_{56}$H$_{73}$N$_{11}$NaO$_{12}$: 1114.5332; found: 1114.5345.

3-Nitro-N-(5-(5-(11-oxo-3,6,9-trioxa-12-azatetracosylcarbamoyl)-1H-pyrazol-3-ylcarbamoyl)-1H-pyrazol-3-yl)-1H-pyrazole-5-carboxamide (Trimer-TEG-dodecyl)

In an argon atmosphere 20.0 mg (18.3 µmol) of Tri(PMB)-TEG-dodecyl were heated in anhydrous TFA (2 mL) to 70° C. for 5 h. After adding cold Et$_2$O, the product precipitated. The precipitate was filtered, washed with Et$_2$O and dried in vacuo; Yield: 9.50 mg (12.7 µmol, 70%), colorless solid.

$^1$H-NMR (500 MHz, DMSO-d$_6$): δ [ppm]=0.83 (t, 3H, CH$_3$), 1.21 (brs, 18H, CH$_2$), 1.39 (m, 2H, CH$_2$), 3.05-3.09 (m, 2H, CH$_2$), 3.31-3.43 (brs, 2H, CH$_2$), 3.56 (brs, 10H, CH$_2$), 3.85 (s, 2H, CH$_2$), 7.26 (brs, 1H, CH-pyrazole, NH-amide), 7.59-7.63 (m, 2H, CH-pyrazole, NH-amide), 7.95 (s, 1H, CH-pyrazole), 8.62 (brs, 1H, CH-Pyrazol, NH-amide), 11.12 (brs, 1H, NH-amide), 11.43 (brs, 1H, NH-amide), 13.22 (brs, 1H, NH-pyrazole), 13.47 (brs, 1H, NH-pyrazole). $^{13}$C-NMR (125.7 MHz, DMSO-d$_6$): δ [ppm]=13.9, 22.1, 26.4, 28.7, 29.0, 29.1, 31.3, 38.1, 68.8, 69.5, 69.6, 69.7, 69.9, 70.2, 98.2, 102.3, 155.1, 156.0, 169.1. Mp: decomposition at 348° C. HRMS (ESI): m/z calcd for C$_{32}$H$_{49}$N$_{11}$NaO$_9$: 754.3607; found: 754.3646; calcd for C$_{32}$H$_{48}$N$_{11}$Na$_2$O$_9$: 776.3426; found: 776.3449.

Bis(N-benzyloxycarbonyl-N$^\varepsilon$-tert-butyloxycarbonyl-(S)-lysinyl)-4,7,10-trioxa-1,13-tri-decanediamine In an argon atmosphere 0.50 g (1.31 mol, 1.00 eq) of Z-Lys(Boc)-OH, 32.0 mg (0.26 mmol, 0.20 eq) of 4-dimethylaminopyridine (DMAP), 250 mg (307 µL, 1.97 mmol, 1.5 eq) of diisopropylcarbodiimide (DIC) and 72 mg (72 µL, 0.33 mmol, 0.25 eq) of 4,7,10-trioxa-1,13-tridecandiamine were dissolved in dry dichloromethane (15 mL) and the solution was stirred at room temperature for 24 h. After filtration of the precipitated urea, dichloromethane was evaporated and the remaining residue was purified over silica gel column, eluting with dichloromethane/methanol (30:1) to yield the product as a colorless oil. Yield 250 mg (0.26 mmol, 79%).

$^1$H-NMR (300 MHz, CDCl$_3$): δ [ppm]=1.31-1.49 (m, 13H, CH$_3$, CH$_2$), 1.59-1.85 (m, 4H, CH$_2$), 3.07 (brs, 2H, CH$_2$), 3.26-3.40 (m, 2H, CH$_2$), 3.52-3.61 (m, 6H, CH$_2$), 4.11-4.16 (m, 1H, CH), 4.74 (brs, 1H, NH), 5.08 (s, 2H, CH$_2$), 5.77 (brs, 1H, NH), 6.89 (brs, 1H, NH), 7.28-7.34 (m, 5H, CH-arom). R$_f$: 0.07 in dichlorometan/methanol 30:1. HRMS (ESI): m/z calcd for C$_{48}$H$_{77}$N$_6$O$_{13}$: 945.5612; found: 945.5612; calcd for C$_{48}$H$_{76}$N$_6$NaO$_{13}$: 967.5363; found: 967.5431.

Bis(amino-N$^\varepsilon$-tert-butyloxycarbonyl-(S)-lysinyl)-4,7,10-trioxa-1,13-tri-decandiamine To a solution of bis(N-benzyloxycarbonyl-N$^\varepsilon$-tert-butyloxycarbonyl-(S)-lysinyl)-4,7,10-trioxa-1,13-tridecandiamine (250 mg, 0.26 mmol) in THF (50 mL) was added 30 mg of Pd—C (10%). The resulting solution was stirred vigorously under H$_2$ atmosphere at room temperature until the starting material disappeared on the TLC plate and in mass spectra. The solution was filtered through celite and concentrated in vacuo to give a pale yellow oil. Yield: 166 mg (0.25 mmol, 96%).

$^1$H-NMR (500 MHz, CDCl$_3$): δ [ppm]=1.33-1.55 (m, 13H, CH$_2$, CH$_3$), 1.77-1.80 (m, 6H, NH$_2$, CH$_2$), 3.09-2.12 (m, 2H, CH$_2$), 3.29-3.38 (m, 3H, CH, CH$_2$), 3.52-3.64 (m, 6H, CH$_2$), 4.71 (brs, 1H, NH), 7.54 (brs, 1H, NH). $^{13}$C-NMR (125.7 MHz, CDCl$_3$): δ [ppm]=23.1, 28.6, 29.4, 30.0, 30.5, 34.5, 34.9, 37.3, 40.3, 55.3, 62.6, 69.9, 70.4, 70.7, 79.2, 156.3, 175.3. HRMS (ESI): m/z calcd for C$_{32}$H$_{65}$N$_6$O$_9$: 677.4808; found: 677.4797; calcd for C$_{32}$H$_{64}$N$_6$NaO$_9$: 699.4627; found: 699.4616.

t-Butyl(10S,28S)-10,28-bis(1-(4-methoxybenzyl)-3-(1-(4-methoxybenzyl)-3-(1-(4-methoxybenzyl)-3-nitro-1H-pyrazole-5-carboxamido)-1H-pyrazole-5-carboxamido)-1H-pyrazole-5-carboxamido)-2,2-dimethyl-4,11,27-trioxo-16,19,22-trioxa-5,12,26-triazadotriacontan-32-ylcarbamate (Trimer-lys(boc))$_2$-TEGDA In an inert atmosphere 26.0 mg (85.2 µmol, 2.50 eq) of PMB-protected Trimer-OH, 59.0 mg (114 µmol, 3.00 eq) of PYBOP, 46.0 mg, 50.0 µL (0.46 mmol, 12.0 eq) of N-methylmorpholine, and 26.0 mg (38.1 µmol, 1.00 eq) of bis(amino-N$^\varepsilon$-tert-butyloxycarbonyl-(S)-lysinyl)-4,7,10-trioxa-1,13-tridecanediamine were dissolved in dry dichloromethane (20 mL) and the solution was heated to 40° C. for 4 days. Dichloromethane was evaporated and the remaining residue was purified over silica gel column, eluting with dichloromethane/methanol (30:1) to yield the product as a colorless solid. Yield: 42.0 mg (19.9 µmol, 52%).

$^1$H-NMR (500 MHz, CDCl$_3$, 333 K): δ [ppm]=1.33-1.42 (m, 13H, CH$_3$, CH$_2$), 1.75-1.93 (m, 4H, CH$_2$), 3.00-3.05 (m, 2H, CH$_2$), 3.32-3.49 (m, 2H, CH$_2$), 3.54-3.65 (m, 6H, CH$_2$), 3.68-3.71 (3s, 9H, CH$_3$-PMB), 4.47-4.51 (m, 1H, CH), 4.67 (brs, 1H, NH), 5.39-5.87 (m, 6H, CH2-PMB), 6.71-6.80 (m, 6H, CH-arom), 6.90 (brs, 2H, NH, CH-pyrazole), 7.10-7.17 (m, 4H, CH-arom), 7.25 (s, 1H, CH-pyrazole), 7.33-7.53 (m, 2H, CH-arom), 7.49-7.53 (brs, 2H, NH, CH-pyrazole), 8.48 (s, 1H, NH), 9.73 (s, 1H, NH). $^{13}$C-NMR (125.7 MHz, CDCl$_3$): δ [ppm]=23.4, 28.8, 29.4, 30.1, 32.7, 38.7, 42.7, 54.0, 54.6, 55.6, 56.4, 70.1, 70.6, 70.8, 98.9, 99.9, 104.7, 114.4, 114.5, 114.6, 127.9, 129.4, 129.5, 129.6, 130.3, 135.3, 135.8, 136.8, 145.2, 145.7, 154.6, 156.2, 156.5, 159.7, 159.8, 160.1, 160.2, 172.2. Rf: 0.20 in dichloromethan/methanol (30:1). Mp: 157.3° C. HRMS (ESI): m/z calcd for $C_{104}H_{126}N_{24}NaO_{25}$: 2134.9248; found: 2134.9258.

N,N'-((5S,23S)-1,27-diamino-6,22-dioxo-11,14,17-trioxa-7,21-diazaheptacosane-5,23-diyl)bis(3-(3-(3-nitro-1H-pyrazole-5-carboxamido)-1H-pyrazole-5-carboxamido)-1H-pyrazole-5-carboxamide) (Trimer-Lys)$_2$-TEGDA A portion of 40.0 mg (18.9 μmol, 1.00 eq) of PMB-protected (Trimer-lys(Boc))$_2$-TEGDA OMe was treated with hot TFA according to general procedure E to yield (Trimer-Lys)$_2$-TEGDA as a colorless solid. Yield: 26.0 mg (18.3 μmol, 97%).

$^1$H-NMR (500 MHz, DMSO-d$_6$): δ [ppm]=1.41-1.48 (m, 2H, CH$_2$), 1.62-1.88 (m, 6H, CH$_2$), 2.84 (t, 2H, CH$_2$), 3.18.3.22 (m, 2H, CH$_2$), 3.46-3.59 (m, 6H, CH$_2$), 4.44-4.48 (m, 1H, CH), 6.96 (brs, 1H, CH-pyrazole), 7.21 (brs, 1H, CH-pyrazole), 7.54-7.56 (brs, 1H, H-21), 7.77 (s, 1H, CH-pyrazole), 7.88 (brs, 1H, NH), 10.45 (brs, 1H, NH), 10.98 (brs, 1H, NH). $^{13}$C-NMR (125.7 MHz, DMSO-d$_6$): δ [ppm]= 22.6, 26.7, 27.1, 29.3, 31.2, 35.9, 36.8, 38.7, 52.6, 67.3, 68.0, 69.4, 69.5, 69.6, 69.7, 102.3, 138.6, 155.1, 155.9, 157.8, 158.1, 171.3. Mp: 200° C. HRMS (ESI): m/z calcd for $C_{46}H_{63}N_{24}O_{15}$: 1191.4899; found: 1191.4879; calcd for $C_{46}H_{62}N_{24}NaO_{15}$: 1213.4719; found: 1213.4693.

3. Manual Solid Phase Peptide Synthesis 3-(3-(3-nitro-1H-pyrazole-5-carboxamido)-1H-pyrazole-5-carboxamido)-1H-pyrazole-5-carboxamido-(S)-lysinyl-(S)-lysinyl-(S)-lysinyl-(S)-lysinyl-(S)-lysinyl-(S)-glycine (Trimer-KKKKKG-OH)

A Wang-resin, preloaded with Fmoc-glycine and an average loading of 0.78 mmol/g, was used as a polymeric carrier. Prior to the first coupling step, the resin was swollen in DMF for 80 min. The coupling of Fmoc-protected amino acids was accomplished by using HBTU and diisopropylethylamine according to the following method: For each coupling step, Fmoc-Lys(Boc)-OH (8.00 equiv), HBTU (7.62 equiv) and diisopropyletylamine (16.00 equiv) were used in a DMF solution. Removal of the Fmoc-protecting group was carried out with 20% piperidine in DMF (1×3 min, 1×7 min) Each coupling and deprotecting step was followed by washing the resin with DMF. The completeness of each coupling step was checked with NF31- and Kaiser-test.[x] The fourth coupling was repeated. After five cycles, the resin was coupled with the PMB-protected Trimer-OH (3.00 equiv), HBTU (3.30 equiv) and diisopropyletylamine (6.00 equiv) in DMF solution for 6 h.

The pyrazole-peptide compound was cleaved off the resin concomitant with deprotection of lysine's ε-amino-Boc groups by means of an acidic cleavage cocktail (93% TFA, 5% TIS and 2% water) during 3 h. The solution was then cooled to 0° C. and the PMB-protected pyrazole-peptide was precipitated and washed with cold diethyl ether. The colorless solid was dried in vacuo.

To cleave the PMB-protecting groups on the pyrazole nucleus, the colorless solid was heated under argon in dry TFA for 5 h to 70° C. The solution was again cooled to 0° C. and treated according to general procedure E to yield the pure Trimer-peptide.

$^1$H NMR (500 MHz, DMSO-d$_6$): δ [ppm]=1.23-1.33 (m, 12H), 1.51-1.56 (m, 14H), 1.63-1.74 (m, 6H), 2.75 (bs, 11H), 4.20-4.31 (m, 4H), 4.41-4.45 (m, 1H), 7.76 (bs, 16H), 7.94-7.99 (m, 2H), 8.02-8.18 (m, 3H), 8.26-8.28 (m, 1H), 11.47 (bs, 1H), 14.97 (bs, 1H). $^{13}$C NMR (125 MHz, CD$_3$OD): δ [ppm]=22.0, 22.2, 26.4, 30.6, 39.2, 53.6, 53.7, 115.3, 117.7, 120.0, 162.6, 163.1, 163.4, 173.3, 173.5, 174.0. Mp: decomposition at 138° C. HRMS (ESI): calcd for $C_{44}H_{72}N_{20}O_{12}$: 1073.5711; found: 1073.5747, calcd for (½ M)$^{2+}$: 537.2913; found: 537.2910, calcd for (⅓ M)$^{3+}$: 358.5302; found: 358.5303.

1-(3-(3-(3-nitro-1H-pyrazole-5-carboxamido)-1H-pyrazole-5-carbox-amido)-1H-pyrazol-5-yl)-1-oxo-5,8,11-trioxa-2-azatridecan-13-carboxamido-(S)-lysinyl-(S)-lysinyl-(S)-lysinyl-(S)-lysinyl-(S)-lysinyl-(S)-glycine (Trimer-TEG-KKKKKG-OH)

Trimer-TEG-KKKKKG-OH was synthesized using the same procedure as the previous (Trimer-LPFFD-OH). Trimer-TEG-OH (3.00 equiv) was used instead of Trimer-OH in this case.

$^1$H-NMR (500 MHz, CDCl$_3$): δ [ppm]=1.31 (brs, 10H, CH$_2$), 1.49-1.65 (m, 20H, CH$_2$), 2.76 (brs, 10H, H-29), 3.39-3.42 (m, 2H, CH$_2$), 3.52-3.61 (m, 10H, CH$_2$), 3.69-3.84 (m, 2H, CH$_2$), 3.93 (s, 2H, CH$_2$), 4.20-4.33 (m, 5H, CH), 7.58 (brs, 15H), 7.93-8.01 (m, 4H), 8.11 (d, 1H, $^3J$=7.26 Hz), 8.26 (t, 1H, $^3J$=7.26 Hz), 8.68 (brs, 1H), 11.14 (s, 1H), 11.44 (s, 1H), 12.77 (brs, 1H), 13.19 (brs, 1H), 13.50 (brs, 1H), 14.96 (brs, 1H). $^{13}$C-NMR (125.7 MHz, CDCl$_3$): δ [ppm]=22.0, 22.1, 22.2, 22.3, 26.5, 26.6, 26.7, 31.3, 31.4, 31.5, 38.6, 38.7, 51.8, 52.1, 52.2, 52.3, 68.8, 69.5, 69.6, 69.7, 70.2, 102.4, 116.0, 118.4, 157.8, 158.1, 158.3, 158.6, 169.4, 171.1, 171.2, 171.3, 171.4, 171.5, 171.7. HRMS (ESI): [M+2H]$^{2+}$=m/z calcd for $C_{52}H_{89}N_{21}O_{16}$: 631.8393; found: 631.8493, [M+3H]$^{3+}$=m/z calcd for $C_{52}H_{90}N_{21}O_{16}$: 421.5619; found: 421.5656.

3-(3-(3-nitro-1H-pyrazole-5-carboxamido)-1H-pyrazole-5-carboxamido)-1H-pyrazole-5-carboxamido-(S)-leucinyl-(S)-prolinyl-(S)-phenylalaninyl-(S)-phenylalaninyl-(S)-aspartic acid (Trimer-LPFFD-OH)

A Wang-resin was used as a polymer support, preloaded with Fmoc-Asp(O$^t$Bu) and an average loading of 0.65 mmol/g. Prior to the first coupling step, the resin was swollen in DMF for 80 min. The coupling of Fmoc-protected amino acids was accomplished by using HBTU and diisopropyletylamine according to the following method: For each coupling step, 9-Fluorenyl-methoxycarbonylamino acid (8.00 equiv), HBTU (7.62 equiv) and diisopropyletylamine (16.00 equiv) were used in a DMF solution. Removal of the Fmoc-protecting group was carried out with 20% piperidine in DMF (1×3 min, 1×7 min). Each coupling and deprotecting step was followed by washing the resin with DMF. The completeness of each coupling step was checked with NF31- and Kaiser-test and the Fmoc-protected amino acid proline with the chloranil-test.[x] After four cycles, the resin was coupled with PMB-protected Trimer-OH (6.00 equiv), HBTU (6.60 equiv) and diisopropyletylamine (12.00 equiv) in DMF solution for 16 h.

The pyrazole-peptide compound was cleaved off the resin concomitant with deprotection of the tert-butyl group by means of an acidic cleavage cocktail (93% TFA, 5% TIS and 2% water) for 3 h. The solution was then cooled to 0° C. and the PMB-protected pyrazole-peptide was precipitated and washed with cold diethyl ether. The colorless solid was dried in vacuo.

To cleave the PMB-protecting groups on the pyrazole nucleus, the colorless solid was heated under argon in dry TFA for 5 h to 70° C. The solution was cooled to 0° C. and treated according to general procedure E to yield the pure Trimer-peptide.

$^1$H NMR (500 MHz, DMSO-d$_6$): δ [ppm]=0.83-0.92 (m, 7H), 1.23 (s, 1H), 1.40-1.45 (m, 1H), 1.65-1.95 (m, 6H), 2.56-2.61 (m, 1H), 2.68-2.84 (m, 3H), 2.93-3.06 (m, 2H), 3.48-3.52 (m, 1H), 3.68-3.72 (m, 1H), 4.32-4.43 (m, 2H), 4.53-4.58 (m, 2H), 4.68-4.73 (m, 1H), 7.15-7.29 (m, 12H), 7.54 (bs, 1H), 7.78 (d, 1H), 7.94 (s, 1H), 8.03 (d, 1H), 8.36 (d, 1H), 8.64 (bs, 1H), 11.07 (bs, 1H), 11.43 (s, 1H), 14.98 (s, 1H). $^{13}$C NMR (125 MHz, DMSO-d$_6$): δ [ppm]=21.2, 23.1, 24.1, 24.3, 28.6, 35.9, 37.2, 37.5, 46.6, 48.5, 48.8, 56.4, 53.6, 59.2, 102.2, 126.0, 126.1, 127.9, 129.1, 129.2, 137.5, 138.6, 155.0, 170.4, 170.5, 107.6, 171.0, 171.5, 172.1. Mp: decomposition at 198° C. HRMS (ESI, neg.): calcd for C$_{45}$H$_{49}$N$_{14}$O$_{13}$: 993.3609; found: 993.3588, (½ M)$^{2-}$: calcd for C$_{45}$H$_{49}$N$_{14}$O$_{13}$: 496.1762; found: 496.1767, (⅓ M)$^{3-}$: calcd for C$_{45}$H$_{49}$N$_{14}$O$_{13}$: 330.4482; found: 330.4488.

1-(3-(3-(3-nitro-1H-pyrazole-5-carboxamido)-1H-pyrazole-5-carbox-amido)-1H-pyrazol-5-yl)-1-oxo-5,8,11-trioxa-2-azatridecan-13-carboxamido-(S)-leucinyl-(S)-prolinyl-(S)-phenylalaninyl-(S)-phenylalaninyl-(S)-aspartic acid (Trimer-TEG-LPFFD-OH)

Trimer-TEG-LPFFD-OH was synthesized using the same procedure as the previous (Trimer-LPFFD-OH). Trimer-TEG-OH (3.00 equiv) was used instead of Trimer-OH in this case.

$^1$H-NMR (500 MHz, CDCl$_3$): δ [ppm]=0.85-0.88 (m, 6H), 1.34-1.93 (m, 7H), 2.54-3.07 (m, 6H), 3.37-3.42 (m, 4H), 3.51-3.59 (m, 10H), 3.90 (s, 2H), 4.30-4.32 (m, 1H), 4.37-4.42 (m, 1H), 4.52-4.62 (m, 2H), 7.16-7.24, 7.53 (brs, 1H), 7.65 (d, 1H), 7.77 (d, 1H), 7.93 (s, 1H), 8.00 (d, 1H), 8.35 (d, 1H), 8.52 (brs, 1H), 11.07 (s, 1H), 11.43 (s, 1H), 12.81 (brs, 2H), 13.48 (brs, 1H), 14.98 (s, 1H). $^{13}$C-NMR (125.7 MHz, CDCl$_3$): δ [ppm]=21.3, 23.2, 23.3, 24.0, 24.2, 28.7, 36.0, 37.2, 37.6, 38.5, 40.3, 46.6, 48.0, 48.6, 53.4, 53.8, 59.2, 68.7, 69.5, 69.7, 70.2, 94.6, 96.7, 98.1, 102.3, 126.1, 126.2, 127.8, 127.9, 129.1, 129.2, 137.4, 137.5, 138.6, 155.0, 155.8, 168.9, 170.2, 170.5, 170.7, 171.1, 171.6, 172.1. HRMS (ESI): [M-H]$^-$=m/z calcd for C$_{53}$H$_{63}$N$_{15}$O$_{17}$: 590.7269; found: 590.7397.

1-(3-(3-(3-Nitro-1H-pyrazole-5-carboxamido)-1H-pyrazole-5-carbox-amido)-1H-pyrazol-5-yl)-1-oxo-5,8,11-trioxa-2-azatridecan-13-carboxamido-(S)-lysinyl-(S)-leucinyl-(S)-valinyl-(S)-phenylalaninyl-(S)-phenylalanine (Tri-TEG-KLVFF)

A Wang-resin was used as a polymer support, preloaded with Fmoc-Phe and an average loading of 0.65 mmol/g. Prior to the first coupling step, the resin was swollen in DMF for 80 min. The coupling of Fmoc-protected amino acids was accomplished by using HBTU and diisopropyletylamine according to the following method: For each coupling step, 9-Fluorenyl-methoxycarbonylamino acid (8.00 equiv), HBTU (7.62 equiv) and diisopropyletylamine (16.00 equiv) were used in a DMF solution. Removal of the Fmoc-protecting group was carried out with 20% piperidine in DMF (1×3 min, 1×7 min). Each coupling and deprotecting step was followed by washing the resin with DMF. The completeness of each coupling step was checked with NF31- and Kaiser-test. After four cycles, the resin was coupled with PMB-protected Trimer-TEG-OH (3.00 equiv), HBTU (3.30 equiv) and diisopropyletylamine (6.00 equiv) in DMF solution for 16 h.

The pyrazole-TEG-peptide compound was cleaved off the resin concomitant with deprotection of the tert-butyl group by means of an acidic cleavage cocktail (93% TFA, 5% TIS and 2% water) for 3 h. The solution was then cooled to 0° C. and the PMB-protected pyrazole-peptide was precipitated and washed with cold diethyl ether. The colorless solid was dried in vacuo.

To cleave the PMB-protecting groups on the pyrazole nucleus, the colorless solid was heated under argon in dry TFA for 5 h to 70° C. The solution was cooled to 0° C. and treated according to general procedure E to yield the pure Trimer-TEG-peptide.

$^1$H-NMR (500 MHz, CDCl$_3$): δ [ppm]=0.69-0.70 (m, 6H), 0.79-0.85 (m, 6H), 1.23-1.68 (m, 9H), 1.82-1.89 (m, 1H), 2.68-3.09 (m, 6H), 3.51-3.59 (m, 12H), 3.91 (s, 2H), 4.07-4.10 (m, 1H), 4.29-4.38 (m, 2H), 4.42-4.47 (m, 1H), 4.54-4.58 (m, 1H), 7.14-7.27 (m, 10H), 7.62-7.63 (m, 4H), 7.69-7.70 (d, 1H), 7.92-7.93 (brs, 2H), 8.1-8.12 (d, 1H), 8.23-8.8.24 (d, 1H), 8.55 (brs, 1H), 11.10 (brs, 1H), 11.34 (s, 1H), 13.21 (brs, 1H), 13.49 ((brs, 1H), 14.98 (brs, 1H). $^{13}$C-NMR (125.7 MHz, CDCl$_3$): δ [ppm]=18.0, 19.2, 21.6, 22.0, 23.1, 24.2, 26.7, 30.8, 31.9, 36.7, 37.6, 38.6, 38.8, 51.0, 51.4, 53.3, 53.4, 57.5, 68.8, 69.6, 69.8, 70.3, 102.3, 126.2, 126.5, 128.0, 128.2, 129.1, 137.3, 137.5, 155.1, 155.9, 169.0, 170.4, 170.9, 171.0, 171.6, 172.6.

4. Thioflavin T Fluorescence Assay

The Aβ(1-40) peptide (Bachem, Bubendorf, Germany) was dissolved in DMSO and stored as (4 μL)-aliquots at −20° C. until use. Aβ(1-42)-peptide (Bachem, Bubendorf, Germany) was prepared in HFIP (hexafluoroisopropanol), lyophilized, redissolved in DMSO and stored as (4 μL)-aliquots at −20° C. The ligands were dissolved in 100% DMSO as 4.95 mM stock solutions and were stored at −20° C.

Thioflavin T (ThT) measurements were carried out in a 384-well plate (Nunc GmbH, Wiesbaden, Germany) in an InfiniTe 200 plate reader (Tecan GmbH, Crailsheim, Germany). Fluorescence intensity was measured at 37° C., 446 nm excitation wavelength (bandwidth 9 nm) and 490 nm emission wavelength with a bandwidth of 20 nm. Each data point was averaged over 40 lamp flashes. Each measurement cycle was started by shaking the sample carrier orbitally for 30 s at medium intensity to avoid settling of larger aggregates. The 384-well plate was covered with a transparent and DMSO-stable film (Nunc GmbH, Wiesbaden, Germany). Each single sample was composed of 33 μM Aβ(1-40) or rather Aβ(1-42) in 10 mM PBS (phosphate buffered saline), 10.7% DMSO, 10 μM ThT and 198 μM of the test compound. For graph representation emission values of fourfold samples were averaged. Each test compound was measured separately, both in 10 mM PBS and 10 mM PBS with ThT to exclude any potential interactions between ligand and ThT.

5. Kinetics of Aβ Aggregation and Disaggregation

ThT Aggregation Assay

To an aliquot of 4 μL Aβ(1-42)-peptide (495 μM stock solution) was first added 2.4 μL of the test compound (4.95 mM stock solution). Then, a mixture of 9.5 μL ThT (62.7 μM stock solution), 6 μL PBS and 38.1 μL water (bidest.) was pipetted. Afterwards the mixture was vortexed and briefly centrifugated. Sixty μL of aggregation mixtures were pipetted in a 384-well plate and the fluorescence intensity (exc. at 446 nm, em. at 490 nm) was measured every hour at 37° C. The 384-well sample carrier was agitated 30 s before each measurement. Each point is the average of quadruplication.

ThT Disaggregation Assay

A mixture of 4 µL Aβ(1-42)-peptide (495 µM stock solution), 9.5 µL ThT (62.7 µM stock solution), 6 µL PBS and 38.1 µL water (bidest.) was incubated for 24 h in a 384-well plate at 37° C. The fluorescence intensity was measured every hour and the 384-well sample carrier was agitated 30 s before each measurement. After 24 h, 2.4 µL of the test compound (4.95 mM stock solution) was added to the solution. The fluorescence measurements were observed/monitored every hour within 5 days and each measurement cycle was started by shaking the sample carrier orbitally for 30 s. For graph representation emission values of fourfold samples were averaged.

6. Equilibrium of Aβ Aggregation and Disaggregation Inhibition Assay

A mixture of 4 µL Aβ(1-42)-peptide (495 µM stock solution), 2.4 µL of the test compound (4.95 mM stock solution), 9.5 µL ThT (62.7 µM stock solution), 6 µL PBS and 38.1 µL water (bidest.) was incubated in a thermo mixer (600 rpm) at 37° C. for 72 h. The ThT assay solution was briefly centrifugated and it was pipetted in a 384-well plate. The ThT fluorescence was measured at $\lambda_{Ex}$=446 nm and $\lambda_{Em}$=490 nm. Each point is the average of quadruplication.

Disaggregation Assay

To obtain preformed fibrils, a mixture of 4 µL Aβ(1-42)-peptide (495 µM stock solution), 6 µL PBS and 38.1 µL water (bidest.) was incubated in a thermo mixer (600 rpm) at 37° C. for 72 h. Then, the test compound (2.4 µL of a 4.95 mM stock solution) was added and the solution was incubated for further five days. After that, 9.5 µL ThT (62.7 µM stock solution) was pipetted and the assay solution was briefly centrifugated. The ThT fluorescence was measured at $\lambda_{Ex}$=446 nm and $\lambda_{Em}$=490 nm. For graph representation emission values of fourfold samples were averaged.

7. Circular-Dichroism-Spectroscopy

Aβ(1-42)-peptide (Bachem, Bubendorf, Germany) was prepared in HFIP (hexafluoroisopropanol), lyophilized, dissolved in DMSO and stored at −20° C. Aβ(1-42) was dissolved in HFIP to a concentration of 500 µM. This solution was diluted with 5 µM potassium phosphate buffer (pH 7.3) to a final peptide concentration of 10 µM. The single sample was composed of 10 µM Aβ(1-42), 5 µM potassium phosphate buffer (pH 7.3), 2% HFIP and 10 µM of the test compound. The samples were transferred to a 10 mm pathlength cuvette immediately after mixing and circular dichroism spectra were recorded on a J-810 spectropolarimeter (Jasco). Measurement range: 190 nm-400 nm. Data pitch: 1 nm. Response: 1 s. Sensitivity: standard. Scanning speed: 100 nm/min. Accumulation: 1. Temperature: 22° C.

8. Fluorescence Correlation Spectroscopy (FCS)

A Confocor I instrument (Zeiss, Evotec) was equipped with an Argon ion laser. A 24 well sample carrier was covered with tesafilm to avoid evaporation. Experiments were carried out at ambient temperature. Rhodamine 6G calibration was ensured before each measurement. Measurement time was 30 s, in a 20 µl total volume. Data evaluation involved determination of the number and height of peaks measured above a threshold given by 5 times the standard deviation of the fluorescence fluctuation. All solutions were sterile filtered before use through 0.22 µm filters.

Measurements were performed with the ConfoCor I instrument (Zeiss, Jena, Evotec, Hamburg, Germany) equipped with an argon laser. The pinhole diameter was 45 µm, and the focus was set 200 µm above the cover glass. Adjustment of diffusion times was achieved by comparing with rhodamine 6G. Measurements were made on Lab-Tek chambered borosilicate cover glasses (Nalge Nunc Int. Corp., Naperville, Ill.) used as sample carriers. The fluorescent probe Aβ(1-42) was synthesized in solid phase using Fmoc chemistry and labeled directly at the N-terminus with OregonGreen™ (Molecular Probes, Leiden, The Netherlands). The peptide was purified by reverse-phase HPLC. Purity was >95% as estimated by reversed phase HPLC and mass spectrometric analysis (Dr. P. Henklein, Institute of Biochemistry, Charité Berlin, Germany). The stock solution contained 500 nM labeled peptide in 5% water-free DMSO, 10 mM sodium phosphate, pH 7.2, and was filtered through 0.45 µm pore nylon filters. Although originally chosen for combination with unlabeled Aβ(1-42) it proved to be more advantageous to use this probe with the less aggressively aggregating Aβ(1-40). The unlabeled Aβ(1-40) (Sigma) was dissolved at 500 µM in 100% water-free DMSO. Comparative measurements with different ligands were performed with trifluoroacetate salts of the ligands, which rendered the sample preparation more convenient because of their higher solubility. The ligands were dissolved at a concentration of 5.4 mM in 100% DMSO. The final incubation assay contained 20 µM Aβ(1-40), 10 nM OregonGreen™-labeled Aβ(1-42), with or without 100 µM ligand in 10 mM sodium phosphate and 6% DMSO in a 50 µl final volume. All solutions were sterile filtered except the Aβ(1-40) stock solution. For each sample the fluorescence intensities were recorded 10 times for 60 s directly after mixing and again after 1 day of incubation at room temperature. It should be noted that the sample holder of the instrument is not thermostated, so experiments were performed at ambient temperature.

The concentration dependence was analyzed by repeated measurement cycles beginning after 2 h of incubation at room temperature and lasting for 8 h. In each cycle fluorescence fluctuations for each sample position were measured 20 times for 30 s with a resolution of 16.7 data points/s. All samples contained 10 mM sodium phosphate, pH 7.2, 50 mM NaCl, 33 µM Aβ(1-40) (Bachem Biochemica, Heidelberg, Germany), 8% DMSO, and 5.6 nM OregonGreen™-labeled Aβ(1-42). The concentration of the ligand varied from 1.35 to 108 µM.

9. Sedimentation Analysis (SA)

Sedimentation velocity centrifugation was performed in an XLA (BeckmanCoulter, Palo Alto, USA) equipped with absorption optics and a four hole titanium rotor. Prior to the centrifugation the solutions were incubated slightly agitated at room temperature for different incubation times. Sample volumes ranging from 300 to 400 µl were filled into standard double sector aluminum center pieces and spun at 20,000 rpm, 20° C. after thermal calibration. Radial scans were recorded at a resolution of 0.002 cm. Detection wavelength was chosen at 493 nm to observe endlabeled FITC or Oregon Green™ and to avoid background absorbance from the test compound.

Data Analysis:

Sedimentation data were analyzed with UltraScan 9.4 (http://www.ultrascan.uthscsa.edu). After timeinvariant noise subtraction, s-value distributions were determined model independently using the enhanced van HoldeWeischet method in the UltraScan software (Demeler and van Holde 2004, van Holde and Weischet 1978). Molecular weight and frictional ratios were determined with two-dimensional spectrum analysis (Brookes et al. 2006) and the genetic algorithm optimization method (Brookes and Demeler 2006, 2007). Hydrodynamic corrections for buffer conditions were made according to data published by Laue et al. (1992) as implemented in UltraScan. The partial specific volume of the Aβ42, v=0.7377 cm³/g was calculated on the basis of its amino acid content by a routine implemented in UltraScan. Experimental intensity data were timeinvariant noise corrected using the 2DSA analysis. The van HoldeWeischet analysis was used to initialize the svalue range in the 2DSA from 1150 S. The frictional ratio range was initialized between 110. 2DSA analyses were performed with 24 grid movings with a 10 point resolution in both dimensions, resulting in a final svalue resolution of 0.625 S and 0.042 f/f$_0$ units. The 2DSA results were used to initialize the GA analysis, and parsimoniously regularized GA distributions were used to initialize the GA Monte Carlo analysis. Data were analyzed on the Bioinformatics Core Facility cluster (University of Texas, Health Science Center, San Antonio, Tex., USA) and on the Lonestar cluster at the Texas Advanced Computing Center (Austin, Tex., USA). The hydrodynamic behavior of a molecule sedimenting in a sector shaped cell is fully described by the Lamm equation (Lamm 1929). In the case of polydisperse samples the shape of the sedimentation boundary and its evolution over time contains information about size, shape and partial concentration of the sedimenting species. To extract the information a linear combination of solutions of the Lamm equation is fitted to the experimental data. The simulated solutes represented in the linear combination of Lamm equations covers both the sedimentation coefficient range as well as the frictional ratio range of solutes present in the experimental data.

10. Transmission Electron Microscopy (TEM)

Transmission Electron Microscopy (TEM):

TEM experiments were performed with a Phillips CM 200 FEG instrument. After absorbing 5 µl of a tenfold diluted sample of the solution used for analytical ultracentrifugation to the holey carbon film coated copper grids (Plano, Wetzlar, Germany) the samples were washed twice with 0.1 and 0.01 mM ammonium acetate and then negatively stained with 2% (w/v) ammonium molybdate solution for 90 s.

11. Cell Culture

MTT viability assays. Cell viability assays were performed as described in Fradinger et al. (Fradinger et al., PNAS, 2008). Rat pheochromocytoma (PC-12) cells were maintained in F-12 nutrient mixture with Kaighn's modification (F-12K) (Gibco BRL, Carlsbad, Calif.) with 15% heat-inactivated horse serum and 2.5% FBS at 37° C. in an atmosphere of 5% $CO_2$. For cell viability assays, cells were plated in 96-well plates at a density of 25,000 cells per well in differentiation media (F-12K, 0.5% FBS, 100 mM nerve growth factor) and maintained for 48 h. Aβ42 was solubilized in a minimal amount of DMSO (Sigma) and then diluted in the F-12K media in the absence or presence of the compounds and then added to cells and incubated for 48 h at 37° C. The final Aβ42 concentration was always kept constant at 10 µM. The stock solutions of the compounds were prepared at 10 mM in DMSO and diluted in the F-12K media at the required concentration. Negative controls included DMSO at the same concentration as in the peptide solutions and media alone. A positive control was 1 mM staurosporine as lethal dose which represented 100% reduction in cell viability, based on which the percentage viability of all of the experimental conditions was calculated. Cell viability was assessed quantitatively by the CellTiter 96 Non-Radioactive Cell Proliferation Assay (Promega). Briefly, 15 µl of 3-(4,5-dimethylthiazol-2-yl)-2, 5-diphenyltetra-zolium bromide (MTT) dye solution was incubated with the cells for 3 h. Then 100 µl of solubilization/stop solution was added and the plates were incubated overnight in the dark to ensure complete solubilization. Plates were read by using a Synergy HT microplate reader (BioTek), and the absorbance at 570 nm (formazan product) minus the absorbance at 630 nm (background) was recorded. Corrected absorbance was used to calculate the percent cell viability from the experimental change (Amedia-Aexperimental) over the dynamic range (Amedia-Astaurosporine). At least three independent experiments with six replicates (n≧18) were carried out, and the results were averaged.

To determine the $IC_{50}$ value of each of the compounds, dose-dependence MTT experiments with the compounds were conducted. Aβ42 was used at 10 µM and the compounds were used at 100, 30, 10, 3, 1 and 0.3 µM. Three independent experiments with six replicates (n≧18) were carried out, and results were averaged. The data for each compound was fitted to the following equation to get the IC50 values.

$$y=\text{Bottom}+((\text{Top}-\text{Bottom})/(1+10^{(x-\log(IC_{50}))}))$$

Top: the y value at which the top of the sigmoidal curve becomes parallel to the X-axis; Bottom: the y value at which the bottom of the sigmoidal curve becomes parallel to the X-axis. $IC_{50}$ in this respect is defined as the concentration of the β-sheet ligand (aminopyrazole trimer derivative), at which the inhibition of Aβ toxicity just reaches 50%.

Figure 15:
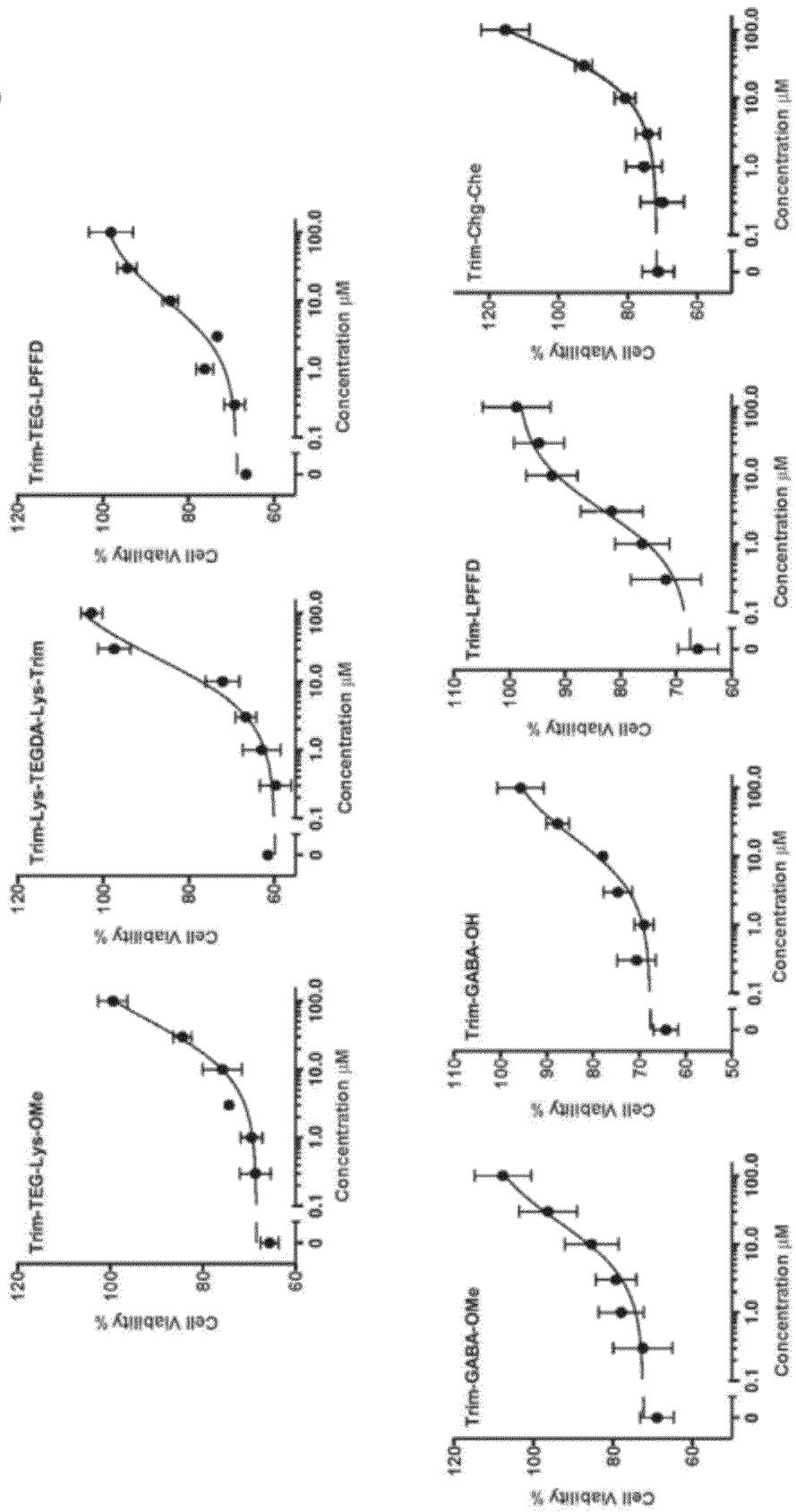
FIG. 15 shows dose-response curves for the inhibition of Aβ-induced toxicity in PC-12 cells by aminopyrazole trimer derivatives.

FIG. 15 shows dose-response curves for the inhibition of Aβ-induced toxicity in PC-12 cells by aminopyrazole trimer derivatives.

Also, MTT viability assays were run with differentiated PC-12 cells. Healthy cells (viability 100%) were lesioned on day 1 with 10 µM Aβ(1-42) and simultaneously protected by 100 µM solutions of aminopyrazoles. After 8 days, the living cells were counted and compared to the untreated control (70%/80%). In both series (with and without TEG spacers) several candidates rescued cell viability significantly, the most impressive results stemming from the TEG-spaced derivatives (FIGS. 13A and 13B). Intriguingly, the most efficient inhibition of Aβ toxicity was achieved with 3 lipophilic extensions and Trimer-TEG-Lys, which were also superior in ThT and related assays. The two GABA derivatives are a surprise—they might potentially interact with GABA receptors and not with the Aβ peptide itself. The above-delineated findings demonstrate, that trimeric aminopyrazoles are indeed active against Aβ-induced toxicity in living cells; they also provide experimental evidence for their low toxicity at relatively high doses of 0.1 mM, in spite of, e.g., the presence of an N-terminal nitro group.

The invention claimed is:

1. A trimeric pyrazole compound of the general formula (I)

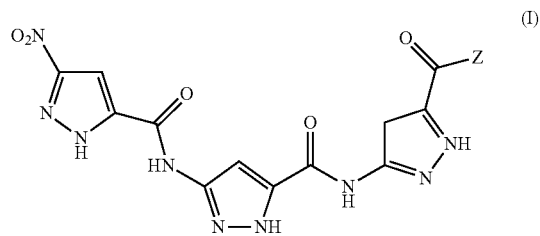

wherein in the general formula (I) the group Z denotes a group X—Y,
wherein X denotes:
(i) a single bond or
(ii) a group of the general formula (II)

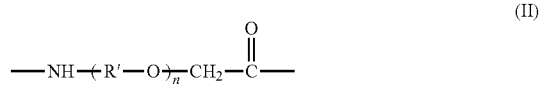

wherein in the general formula (II) the group R' denotes a divalent rest selected from $C_2$-$C_{10}$-alkylene and n is an integer selected in the range of from 1 to 20;

wherein Y denotes:
(i) a group —O⁻ or a group —OH;
(ii) a carboxylic acid radical or a (poly)amino acid radical or its pharmacologically acceptable salts; its esters; or its amides;
(iii) an amine or diamine radical which is optionally protonated.

2. The trimeric pyrazole compound according to claim 1, wherein X denotes:
(i) a single bond or
(ii) a group of the general formula (II)

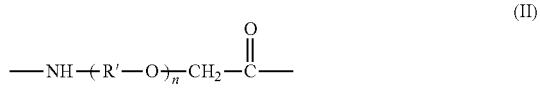
(II)

wherein in the general formula (II) the group R' denotes a divalent rest selected from $C_2$-$C_{10}$-alkylene and n is an integer selected in the range of from 1 to 20;
wherein Y denotes:
(i) a group —O⁻ or a group —OH;
(ii) a (poly)amino acid radical or its pharmacologically acceptable salts; its esters; or its amides;
(iii) an amine or diamine radical which is optionally protonated.

3. The trimeric pyrazole compound according to claim 1, wherein X denotes a single bond if Y denotes a group —O⁻ or a group —OH; or
wherein X denotes a single bond or a group of the general formula (II) as defined in claim 1 if Y denotes (ii) a (poly)amino acid radical or its pharmacologically acceptable salts; its esters; or its amides or (iii) an amine or diamine radical which is optionally protonated.

4. The trimeric pyrazole compound according to claim 1, wherein X denotes a single bond or a group of the general formula (II) as defined in claim 1 and Y denotes (ii) a (poly) amino acid radical or its pharmacologically acceptable salts; its esters; or its amides or (iii) an amine or diamine radical which is optionally protonated.

5. The trimeric pyrazole compound according to claim 1, wherein
X denotes a group of the general formula (III)

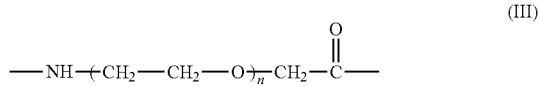
(III)

wherein in the general formula (III) n is an integer selected in the range of from 1 to 20.

6. The trimeric pyrazole compound according to claim 1, wherein
X denotes a group of the general formula (IV)

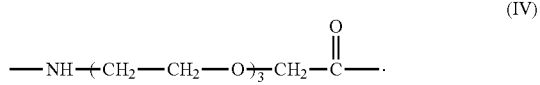
(IV)

7. The trimeric pyrazole compound according to claim 1, wherein the (poly)amino acid radical is derived from α- to ω-amino acids.

8. The trimeric pyrazole compound according to claim 1, wherein the (poly)amino acid radical is derived from proteinogenic or non-proteinogenic amino acids.

9. The trimeric pyrazole compound according to claim 1, wherein the (poly)amino acid radical is derived from naturally occurring amino acids.

10. The trimeric pyrazole compound according to claim 1, wherein the (poly)amino acid radical is derived from the group consisting of lysine, glycine, cyclohexylglycine, leucine, isoleucine, proline, phenylalanine, aspartic acid, amino butyric acids, valine and combinations thereof.

11. The trimeric pyrazole compound according to claim 1, wherein the (poly)amino acid radical is attached or linked via an amide and/or peptide bond.

12. The trimeric pyrazole compound according to claim 1, wherein the polyamino acid radical comprises or is composed of at least two or more amino acids attached or linked to each other via an amide and/or peptide bond each.

13. The trimeric pyrazole compound according to claim 1, wherein the polyamino acid radical comprises or is composed of from 2 to 20 amino acids, wherein the amino acids are attached or linked to each other via an amide and/or peptide bond each.

14. The trimeric pyrazole compound according to claim 1, wherein the polyamino acid radical comprises or is composed of polylysine units optionally combined with at least one amino acid different from lysine.

15. The trimeric pyrazole compound according to claim 1, wherein the amine or diamine radical is selected from the group consisting of the following radicals:
(i) —NH—$(CH_2)_p$—X' with p=1 to 20 and X'=H, $NH_2$, $NH_3^+$;
(ii) —NH—CH(cyclohexyl)-$CH_3$ or —NH—$CH_2$—$CH_2$(cyclohexyl).

16. A medicament or a pharmaceutical composition for the therapeutic treatment of a protein misfolding disease, wherein the protein misfolding disease is Alzheimer's disease (AD), Parkinson's disease, Creutzfeldt-Jakob disease, or Huntington's disease, wherein the medicament or pharmaceutical composition comprises at least one trimeric pyrazole compound as defined in claim 1, wherein the medicament or pharmaceutical composition further comprises at least one pharmaceutically acceptable excipient.

17. A kit, wherein the kit comprises at least one trimeric pyrazole compound as defined in claim 1.

18. A method of treating a human or an animal suffering from a protein misfolding disease, wherein the protein misfolding disease is Alzheimer's disease (AD), Parkinson's disease, Creutzfeldt-Jakob disease, or Huntington's disease, the method comprising administering an efficient amount of at least one trimeric pyrazole compound as defined in claim 1.

* * * * *